(12) United States Patent
Chavan et al.

(10) Patent No.: US 8,715,654 B2
(45) Date of Patent: May 6, 2014

(54) METHODS OF MODULATING THE NEGATIVE CHEMOTAXIS OF IMMUNE CELLS

(75) Inventors: Surendra Chavan, Atlanta, GA (US); Jonathan L. Moon, Decatur, GA (US); Lopa Bhatt, Roswell, GA (US)

(73) Assignee: Celtaxsys, Inc., Atlanta, GA (US)

( * ) Notice: Subject to any disclaimer, the term of this patent is extended or adjusted under 35 U.S.C. 154(b) by 790 days.

(21) Appl. No.: 12/572,445

(22) Filed: Oct. 2, 2009

(65) Prior Publication Data

US 2010/0104587 A1   Apr. 29, 2010

Related U.S. Application Data

(60) Provisional application No. 61/102,177, filed on Oct. 2, 2008, provisional application No. 61/222,217, filed on Jul. 1, 2009.

(51) Int. Cl.
*A61K 39/395* (2006.01)
*A61K 38/17* (2006.01)
*C12N 15/113* (2010.01)

(52) U.S. Cl.
USPC ............ 424/130.1; 424/172.1; 424/174.1; 424/278.1; 514/1.5; 514/1.6; 514/1.8; 514/12.2; 514/13.5; 514/15.3; 514/18.7; 514/21.92

(58) Field of Classification Search
None
See application file for complete search history.

(56) References Cited

U.S. PATENT DOCUMENTS

| | | | |
|---|---|---|---|
| 6,268,151 B1 * | 7/2001 | Murray et al. | 435/6.14 |
| 6,372,772 B1 * | 4/2002 | Kirkpatrick et al. | 514/396 |
| 2003/0017141 A1 | 1/2003 | Poznansky et al. | |
| 2003/0119079 A1 | 6/2003 | Hanash et al. | |
| 2004/0091919 A1 * | 5/2004 | Bennett et al. | 435/6 |
| 2004/0223971 A1 * | 11/2004 | Chang et al. | 424/155.1 |
| 2005/0181398 A1 | 8/2005 | Fung et al. | |
| 2006/0088823 A1 | 4/2006 | Haab et al. | |
| 2006/0177453 A1 | 8/2006 | Mather et al. | |
| 2006/0276389 A1 * | 12/2006 | Poznansky et al. | 514/12 |
| 2007/0054922 A1 * | 3/2007 | Sircar et al. | 514/253.07 |
| 2007/0212738 A1 | 9/2007 | Haley et al. | |
| 2008/0213319 A1 | 9/2008 | Kang et al. | |
| 2010/0203087 A1 | 8/2010 | Kang et al. | |

FOREIGN PATENT DOCUMENTS

| | | | |
|---|---|---|---|
| WO | WO03/052095 | * | 6/2003 |
| WO | 2005/009350 A2 | | 2/2005 |
| WO | WO2007/008652 | * | 9/2007 |
| WO | WO2007/111938 | * | 10/2007 |

OTHER PUBLICATIONS

Lee et al (Gynecologic Oncology, 2007, vol. 104, pp. 338-344).*
Chatterjee et al (Biochemistry, 2009, vol. 48, pp. 5994-6001).*
The abstract of Brenner et al (International Journal of Oncology, 2004, vol. 25, pp. 1157-1163).*
Djafarzadeh et al (Experimental Cell Research, 1997, vol. 236, pp. 427-435).*
The abstract of Zhang et al (International Journal of Oncology, 2005, vol. 26, pp. 1575-1580).*
Matta et al (Expert Opinion on Therapeutic Targets, 2012, vol. 16, pp. 515-523).*
Hawkinson et al (European Journal of Pharmacology, 1997, vol. 337, pp. 315-324).*
Meng et al (FEBS Letters, 2005, vol. 579, pp. 1311-1319).*
Wickstrom et al (Biochemical Pharmacology, 2007, vol. 73, pp. 25-33).*
The abstract of Marikovsky et al (Clinical and Experimental Metastasis, 2000, vol. 19, No. 9, p. 746).*
Liao et al (Life Sciences, 2005, vol. 77, pp. 325-335).*
Nicholls et al (Journal of the American College of Cardiology, 2006, vol. 47, pp. 992-997).*
Naruko et al (Circulation, 2002, vol. 106, pp. 2894-2900).*
Puranik et al (Atherosclerosis, published online Jun. 27, 2007, vol. 196, pp. 240-247).*
Vianello, F., et al., "Murine B16 Melanomas Expressing High Levels of the Chemokine Stromal-Derived Factor-1/CXCL12 Induce Tumor-Specific T Cell Chemorepulsion and Escape from Immune Control," J. Immunology, 176(5):2902-2914 (2006).
Brooks, P. C., et al., "Disruption of Angiogenesis by PEX, a Noncatalytic Metalloproteinase Fragment with Integrin Binding Activity," Cell, 92: 391-400 (1998).
Dang, D., et al., "αvβ3 integrin and cofilin modulate K1735 melanoma cell invasion," Experimental Cell Research, 312: 468-477 (2006).
Mondola, P., et al., "Evidence for Secretion of Cytosolic CuZn Superoxide Dismutase by Hep G2 Cells and Human Fibroblasts," Int. J. Biochem. Cell Biol., 28(6): 677-681 (1996).
Desmarais, V., et al., Cofilin takes the lead, Journal of Cell Science, 118: 19-26 (2005).

* cited by examiner

*Primary Examiner* — Karen Canella

(74) *Attorney, Agent, or Firm* — Elmore Patent Law Group, P.C.; Mahreen Chaudhry Hoda; Carolyn S. Elmore, Esq.

(57) ABSTRACT

The current invention is directed to methods of inducing migration of an immune cell toward a cancer cell comprising inhibiting the activity of a chemorepellant released from the cancer cell.

2 Claims, 40 Drawing Sheets

METHODS OF MODULATING THE NEGATIVE CHEMOTAXIS OF IMMUNE CELLS

RELATED APPLICATIONS

This application claims the benefit of U.S. Provisional Application No. 61/102,177, filed Oct. 2, 2008 and U.S. Provisional Application No. 61/222,217 filed Jul. 1, 2009. The entire teachings of the above applications are incorporated herein by reference.

BACKGROUND OF THE INVENTION

A long-standing dilemma in tumor immunology is the ability of solid tumor cells to escape immune surveillance despite demonstrable antitumor T-cell response. Primarily, the immune evasion mechanism of tumor has been evaluated in the context of expression of immunosuppressive bio-molecules viz., IL-10, transforming growth factor-b (TGF-b), indoleamine-2,3-deoxygenase (IDO), macrophage colony stimulating factor (M-CSF), arginase, prostaglandin E2 (PGE2), cyclooxygenase-2 (COX2) and nitric-oxide synthase 2 (NOS2), IL-6, chemokine CXCL12 and the like, that inhibit the function of dendritic cells (DC) and T cells. The increased expression of death inducing molecules (FasL & TRAIL), which induces apoptosis in tumor infiltrating T cells, has also been elucidated to explain the mechanism by which tumors evade the immune system.

The migration of immune cells to a target site is a major step in eliciting the immune response against tumor cell. Chemotaxis, or the oriented movement of a cell in response to a chemical agent, is a complex and highly integrated process. The movement can be positive (toward) or negative (away) from a chemical gradient. Movement toward an agent or stimulus is termed positive chemotaxis (i.e., the agent or stimulus is chemoattractive for the cell), while movement away from an agent or stimulus is termed negative chemotaxis (i.e., the agent or stimulus is chemorepulsive for the cell). It is believed that for both prokaryotes and eukaryotes, cells undergoing chemotaxis sense a change in agent concentration and, thereby, move in response to the concentration gradient. Chemoattraction (CA) and chemorepulsion (CR) are therefore properties of the agent or stimulus, while chemotaxis is a property of cells.

The present inventors have discovered proteins which are expressed (secreted) by tumor cells which keep anti-tumor T cells (CD4 & CD8), neutrophils, NK cells at the bay while concomitantly recruiting regulatory T cells at tumor sites and thus mediating evasion of the immune response. It would be advantageous to identify these proteins released from cancer cells that induce negative chemotaxis of immune cells and/or inhibit the activity of these proteins in order to induce positive chemotaxis of immune cells toward cancer cells.

SUMMARY OF THE INVENTION

The present invention provides methods of inducing the migration of an immune cell toward a cancer cell comprising inhibiting the activity of a chemorepellant released from the cancer cell.

In some embodiments, the activity of a chemorepellant released from a human cancer cell is inhibited. In other embodiments, the human cancer cell is selected from the group consisting of a renal adenocarcinoma cell, renal carcinoma cell, a glioblastoma cell a colon carcinoma cell, a hepatocellular carcinoma cell, an ovarian carcinoma cell and a prostate cancer cell.

In one embodiment, the activity of a chemorepellant released from the cancer cell is inhibited, wherein the chemorepellant comprises a sequence that has substantial identity to a protein isolated from ovarian cancer cystic fluid or to a biologically active fragment thereof, wherein the isolated protein or fragment thereof is capable of inducing chemorepulsion of an immune cell. In another embodiment, the chemorepellant comprises a sequence that has substantial identity to a protein isolated from a supernatant of a cell line or to a biologically active fragment thereof, wherein the cell line is selected from the group consisting of a human renal adenocarcinoma cell, a human renal carcinoma cell, a human glioblastoma cell, a human colon carcinoma cell, a human hepatocellular carcinoma cell, a human ovarian carcinoma cell and a human prostate cancer cell.

In another embodiment, the chemorepellant has substantial identity to the protein isolated from an ovarian cystic fluid, or to a biologically active fragment thereof. In another embodiment, the chemorepellant has substantial identity to of a protein isolated from a supernatant of a cell line, or a biologically active fragment thereof, wherein the cell line is selected from the group consisting of a human renal adenocarcinoma cell, a human renal carcinoma cell, a human glioblastoma cell, a human colon carcinoma cell, a human hepatocellular carcinoma cell, a human ovarian carcinoma cell and a human prostate cancer cell.

In one embodiment, the chemorepellant has substantial identity to a protein selected from a chemorepellant protein set forth in Tables 1 to 9, or a biologically active fragment of thereof. In an additional embodiment, the chemorepellant has substantial identity to a protein selected from a protein set forth in Table 10 to 11, or a biologically active fragment thereof. In another embodiment, the chemorepellant has substantial identity to a protein selected from the group selected from the group consisting of actin, 14-3-3 zeta/delta, apolipoprotein A1, hemopexin, PARK7, cofilin-1, 14-3-3 epsilon, 14-3-3-gamma, phosphoserine phosphatase, superoxide dismutase, profilin-2, beta-2 microglobulin, cytochrome c, cystatin B, macrophage migration inhibitory factor (MIF), FK506 binding protein, thioredoxin, galectin 3, human transferrin, human EF-1-gamma and human galectin 3 binding protein, or a biologically active fragment of any of thereof.

In yet another embodiment, the invention is a method of treating cancer in a patient in need thereof comprising inhibiting the activity of a chemorepellant released from a cancer cell.

In a further embodiment, the invention is a method of inducing negative chemotaxis of a human immune cell comprising administering an inventive chemorepellant. In some embodiments, the chemorepellant comprises a sequence that has substantial identity to a protein isolated from ovarian cancer cystic fluid or to a biologically active fragment thereof, wherein the isolated protein or fragment thereof is capable of inducing chemorepulsion of an immune cell. In another embodiment, the invention is a method of inducing negative chemotaxis of a human immune cell comprising administering a chemorepellant, wherein the chemorepellant comprises a sequence that has substantial identity to a protein isolated from a supernatant of a cell line selected from the group consisting of a human renal adenocarcinoma cell, a human renal carcinoma cell, a human glioblastoma cell, a human colon carcinoma cell, a human hepatocellular carcinoma cell, a human ovarian carcinoma cell and a human prostate cancer cell, or a biologically active fragment of said isolated protein, wherein said protein or fragment thereof is capable of inducing negative chemotaxis. In an additional embodiment, the administered chemorepellant comprises a sequence that has substantial identity to a protein listed in Tables 1 to 9, or to a biologically active fragment thereof. In an additional embodiment, the administered chemorepellant has substantial identity to a protein listed in Tables 10 to 11, or to a biologically active fragment thereof. In yet another embodiment, the administered chemorepellant comprises a sequence that has substantial identity to a protein selected from the group selected from the group consisting of actin, 14-3-3 zeta/delta, apolipoprotein A1, hemopexin, PARK7, cofilin-1, 14-3-3 epsilon, 14-3-3-gamma, phosphoserine phosphatase, superoxide dismutase, profilin-2, beta-2 microglobulin, cytochrome c, cystatin B, macrophage migration inhibitory factor (MIF), FK506 binding protein, thioredoxin, galectin 3, human transferrin, human EF-1-gamma and human galectin 3 binding protein, or a biologically active fragment thereof.

In yet another embodiment, the invention is a method of treating a condition mediated by migration of a human migratory cell toward a chemotactic site comprising administering to said patient a therapeutically effective amount of an inventive chemorepellant. In some embodiments, the chemorepellant comprises a sequence that has substantial identity to a protein isolated from ovarian cancer cystic fluid, or to a biologically active fragment thereof, wherein the isolated protein or fragment thereof is capable of inducing chemorepulsion of an immune cell. In a further embodiment, the invention is a method of treating a condition mediated by migration of a human migratory cell toward a chemotactic site comprising administering to said patient a therapeutically effective amount of a chemorepellant, wherein said chemorepellant comprises a sequence that has substantial identity to a protein isolated from a supernatant of a cell line selected from the group consisting of a human renal adenocarcinoma cell, a human renal carcinoma cell, a human glioblastoma cell, a human colon carcinoma cell, a human hepatocellular carcinoma cell, a human ovarian carcinoma cell and a human prostate cancer cell, or to a biologically active fragment of any of thereof, wherein the protein or fragment thereof is capable of inducing negative chemotaxis of an immune cell.

These and other aspects of the invention, as well as various advantages and utilities, will be more apparent with reference to the drawings and the detailed description of the embodiments of the invention.

DETAILED DESCRIPTION OF THE INVENTION

Figure 1:
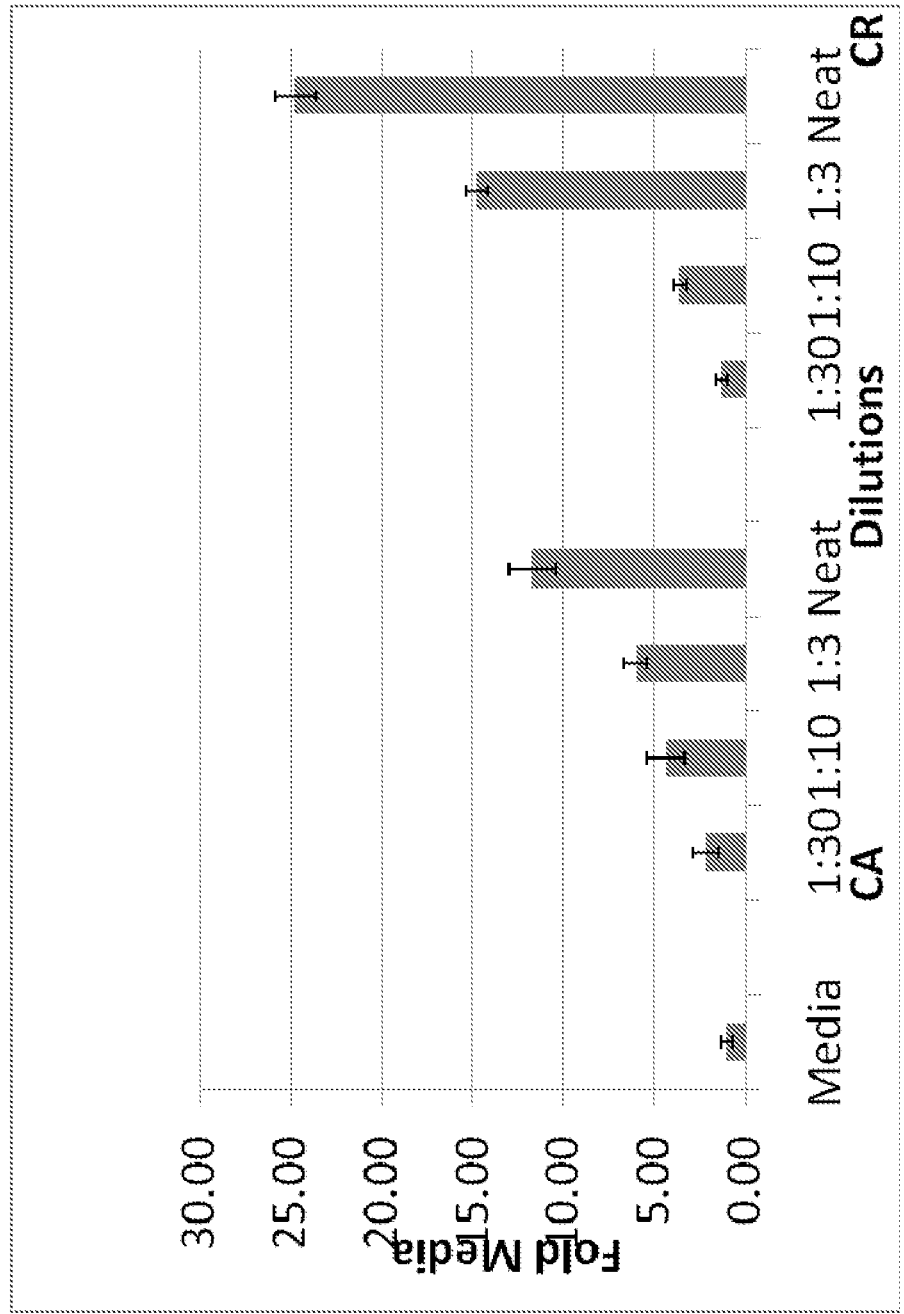
FIG. 1 is a bar graph showing fold induction (over media) of chemorepulsion (right) and chemoattraction (left) of neutrophils treated with 1:30, 1:10, 1:3 and neat dilutions of ovarian cancer cyst fluid.

A description of the embodiments of the invention follows.

As used herein, "a" or "an" are taken to mean one or more unless otherwise specified.

The present invention is based on the surprising discovery that one or more proteins isolated from ovarian cancer cystic fluid and/or from the supernatants of human cancer cell cultures induce negative chemotaxis of neutrophils. For example, as shown in Example 1, neutrophils contacted with certain chromatographic fractions of ovarian cancer cystic fluid showed greater than 9-fold induction of chemotaxis than that in response to media.

In one embodiment, the invention is a method of inducing migration of an immune cell toward a cancer cell comprising inhibiting the activity of a chemorepellant released from the cancer cell. In some embodiments, the cancer cell is selected from the group consisting of colon carcinoma cell, prostate cancer cell, breast cancer cell, lung cancer cell, skin cancer cell, liver cancer cell, bone cancer cell, pancreas cancer cell, ovarian cancer cell, testicular cancer cell, bladder cancer cell, kidney cancer cell, brain cancer cell, glioma cell, head and neck cancer cell. In another embodiment, the cancer cell is a renal adenocarcinoma cell, renal carcinoma cell, a glioblastoma cell a colon carcinoma cell, a hepatocellular carcinoma cell, an ovarian carcinoma cell and a prostate cancer cell.

According to the present method, migration of an immune cell toward a cancer cell can be induced by inhibiting the activity of a chemorepellant released from the cancer cell. The chemorepellant released from the cancer cell is a protein that induces negative chemotaxis of an immune cell. The inventive methods also encompass a method of inducing negative chemotaxis of an immune cell comprising administering a chemorepellant, wherein the chemorepellant comprises a sequence that has substantial identity to a protein release from a cancer cell, or a biologically active fragment thereof.

A "chemorepellant" is an agent or stimulus that induces, elicits or triggers negative chemotaxis of a migratory cell (movement away from an agent or stimulus). In one embodiment, the chemorepellant comprises an amino acid sequence that has substantial identity to a protein isolated from ovarian cancer cystic fluid, or to a biologically active fragment thereof, wherein the isolated protein or fragment thereof is capable of inducing chemorepulsion of an immune cell. In another embodiment, the chemorepellant has substantial identity to a protein isolated from ovarian cancer cystic fluid or to a biologically active fragment thereof. In an additional embodiment, the chemorepellant has substantial identity to a protein isolated from ovarian cancer cystic fluid.

In another embodiment, the chemorepellant comprises a sequence that has substantial identity to a protein isolated from a supernatant of a cell line selected from the group consisting of a human renal adenocarcinoma cell, a human renal carcinoma cell, a human glioblastoma cell, a human colon carcinoma cell, a human hepatocellular carcinoma cell, a human ovarian carcinoma cell and a human prostate cancer cell, or a biologically active fragment of said isolated protein, wherein said protein or fragment thereof is capable of inducing negative chemotaxis. In yet another embodiment, the chemorepellant has substantial identity to a protein isolated from a supernatant of a cell line selected from the group consisting of a human renal adenocarcinoma cell, a human renal carcinoma cell, a human glioblastoma cell, a human colon carcinoma cell, a human hepatocellular carcinoma cell, a human ovarian carcinoma cell and a human prostate cancer cell, or a biologically active fragment of said isolated protein.

In yet another embodiment, the chemorepellant comprises a sequence that has substantial identity to a protein set forth in Tables 1 through 9 (shown below in Examples 1 to 3), or to a biologically active fragment thereof. In a further embodiment, the chemorepellant has substantial identity to a protein set forth in Tables 1 through 9, or a biologically active fragment thereof. In yet another embodiment, the chemorepellant is a protein set forth in Tables 1 through 9. In another embodiment, the chemorepellant is a protein set forth in Tables 10 to 11.

In an additional embodiment, the chemorepellant protein is a protein that is released by at least two distinct cancer cells. Cancer cells are distinct when they are of different origin or different cancer cell types. For example, liver cancer cells and ovarian cancer cells are distinct cancer cells. Similarly, a cancer cell of the kidney cancer cell line, ACHN, is distinct from the kidney cancer cell line 786-O. In a further embodiment, the chemorepellant protein has substantial identity to a protein set forth in Tables 10-11, or to a biologically active fragment thereof.

In another embodiment, the chemorepellant comprises a sequence that has substantial identity to the amino acid sequence of a protein selected from the group consisting of actin, 14-3-3 zeta/delta, apolipoprotein A1, hemopexin, PARK7, cofilin-1, 14-3-3 epsilon, 14-3-3-gamma, phosphoserine phosphatase, superoxide dismutase, profilin-2, beta-2 microglobulin, cytochrome c, cystatin B, macrophage migration inhibitory factor (MIF), FK506 binding protein, thioredoxin, galectin 3, human transferrin, human EF-1-gamma and human galectin 3 binding protein, or a biologically active fragment of any of thereof. In an additional embodiment, the chemorepellant has substantial identity to a protein selected from the group consisting of actin, 14-3-3 zeta/delta, apolipoprotein A1, hemopexin, PARK7, cofilin-1, 14-3-3 epsilon, 14-3-3-gamma, phosphoserine phosphatase, superoxide dismutase, profilin-2, beta-2 microglobulin, cytochrome c, cystatin B, macrophage migration inhibitory factor (MIF), FK506 binding protein, thioredoxin, galectin 3, human transferrin, human EF-1-gamma and human galectin 3 binding protein. In a further embodiment, the chemorepellant is a protein selected from the group consisting of actin, 14-3-3 zeta/delta, apolipoprotein A1, hemopexin, PARK7, cofilin-1, 14-3-3 epsilon, 14-3-3-gamma, phosphoserine phosphatase, superoxide dismutase, profilin-2, beta-2 microglobulin, cytochrome c, cystatin B, macrophage migration inhibitory factor (MIF), FK506 binding protein, thioredoxin, galectin 3, human transferrin, human EF-1-gamma and human galectin 3 binding protein. Accession Numbers for these proteins are shown below in Tables 1 through 9.

A biologically active fragment is a peptide fragment of a naturally occurring protein or the full-length protein that retains at least some of the biological activity of the naturally occurring protein or the full-length protein. In some embodiments, the biological activity is the ability to induce chemorepulsion of a human migratory cell.

Ovarian cancer cystic fluid refers to cystic fluid from patients with ovarian carcinomas.

In some embodiments, the chemorepellant comprises a sequence that has substantial identity to a protein isolated from the supernatant of a cancer cell culture, wherein the culture is of a human cancer cell selected from the group consisting of a renal adenocarcinoma cell, renal carcinoma cell, a glioblastoma cell a colon carcinoma cell, a hepatocellular carcinoma cell, an ovarian carcinoma cell and a prostate cancer cell. In one embodiment, the human renal adenocarcinoma cell line is ACHN. In another embodiment, the human renal carcinoma cell line is 786-O. In another embodiment, the human glioblastoma cell line is SF539 or U251. In an additional embodiment, the human colon carcinoma cell line is HCC-2998. In a further embodiment, the human hepatocellular carcinoma cell line is HepG2 (ATCC No. HB-8065). In yet another embodiment, the human ovary clear cell carcinoma cell line is ATCC No. CRL-1978. In an additional embodiment, the human prostate cancer cell line is PC3 (ATCC No. CRL-1435).

In certain embodiments of the invention, the chemorepellant comprises a sequence that has substantial identity to the amino acid sequence of a protein isolated from ovarian cancer cystic fluid or the supernatant of a cancer cell line. In these embodiments, the ovarian cancer cystic fluid or supernatant is fractionated and the protein is isolated from a chemorepulsive fraction. A chemorepulsive fraction is a fraction that induces chemorepulsion of a human migratory cell. The ovarian cystic fluid or supernatant can be fractionated, for example, by size exclusion and anion exchange chromatography.

Exemplary amino acid sequences for actin, 14-3-3 zeta/delta, apolipoprotein A1, hemopexin, PARK7, cofilin-1, 14-3-3 epsilon, 14-3-3-gamma, phosphoserine phosphatase, superoxide dismutase, profilin-2, beta-2 microglobulin, cytochrome c, cystatin B, macrophage migration inhibitory factor (MIF), FK506 binding protein, thioredoxin, galectin 3, human transferrin, human EF-1-gamma and human galectin 3 binding protein are shown below:

```
Actin (IPI Acc. No. IPI100021439 (+2))
                                            (SEQ ID NO: 1)
MDDDIAALVVDNGSGMCKAGFAGDDAPRAVFPSIVGRPRHQGVMVGMGQK

DSYVGDEAQSKRGILTLKYPIEHGIVTNWDDMEKIWHHTFYNELRVAPEE

HPVLLTEAPLNPKANREKMTQIMFETFNTPAMYVAIQAVLSLYASGRTTG

IVMDSGDGVTHTVPIYEGYALPHAILRLDLAGRDLTDYLMKILTERGYSF

TTTAEREIVRDIKEKLCYVALDFEQEMATAASSSSLEKSYELPDGQVITI

GNERFRCPEALFQPSFLGMESCGIHETTFNSIMKCDVDIRKDLYANTVLS

GGTTMYPGIADRMQKEITALAPSTMKIKIIAPPERKYSVWIGGSILASLS

TFQQMWISKQEYDESGPSIVHRKCF 14-3-3 (IPI Acc. No. IPI100021263 (+1))
                                            (SEQ ID NO: 2)
MDKNELVQKAKLAEQAERYDDMAACMKSVTEQGAELSNEERNLLSVAYKN

VVGARRSSWRVVSSIEQKTEGAEKKQQMAREYREKIETELRDICNDVLSL

LEKFLIPNASQAESKVFYLKMKGDYYRYLAEVAAGDDKKGIVDQSQQAYQ

EAFEISKKEMQPTHPIRLGLALNFSVFYYEILNSPEKACSLAKTAFDEAI

AELDTLSEESYKDSTLIMQLLRDNLTLWTSDTQGDEAEAGEGGEN

GLLPVLESFK VSFLSALEEY TKKILNTQ

Apoliprotein A1 (SwissProt Acc. No. P02647)
                                            (SEQ ID NO: 3)
MKAAVLTLAV LFLTGSQARH FWQQDEPPQSPWDRVKDLATVYVDVLKD

SGRDYVSQFEGSALGKQLNLKL LDNWDSVTST FSKLREQLGP

VTQEFWDNLE KETEGLRQEM SKDLEEVKAKVQPYLDDFQK

KWQEEMELYR QKVEPLRAELQEGARQKLHE LQEKLSPLGE

EMRDRARAHVDALRTHLAPYSDELRQRLAARLEALKENGG
```

ARLAEYHAKA TEHLSTLSEK AKPALEDLRQ

Hemopexin (SwissProt Acc. No. P02790)
(SEQ ID NO: 4)
MARVLGAPVA LGLWSLCWSL AIATPLPPTS AHGNVAEGET

KPDPDVTERCSDGWSFDATTLDDNGTMLFF KGEFVWKSHK

WDRELISERW KNFPSPVDAAFRQGHNSVFL IKGDKVWVYPPEKKEKGY

P LLQDEFPGIP SPLDAAVECHRGECQAEGVL FFQGDREWFW

DLATGTMKERSWPAVGNCSS ALRWLGRYYCFQGNQFLRFD

PYRGEYPPRY PRDVRDYFMP CPGRGHGHRNGTGHGNSTHH

GPEYMRCSPH LVLSALTSDNHGATYAFSGT HYWRLDTSRD

GWHSWPIAHQWPQGPSAVDA AFSWEEKLYL VQGTQVYVFL

TKGGYTLVSGYPKRLEKEVG TPHGIILDSVDAAFICPGSS

RLHIMAGRRL WWLDLKSGAQATWTELPWPH EKVDGALCME

KSLGPNSCSANGPGLYLIHG PNLYCYSDVEKLNAAKALPQ

PQNVTSLLGC TH

PARK-7 DJ1 (IPI Acc. No. IPI00298547)
(SEQ ID NO: 5)
MASKRALVILAKGAEEMET IPVDVMRRAG IKVTVAGLAGKDPVQCSRD

VVICPDASLED AKKEGPYDVVVLPGGNLGAQNLSESAAVKEILKEQENR

KGLIAAICAGPTALLAHEIGFGSKVTTHPLAKDKMMNGGHYTYSENRVEK

DGLILTSRGPGTSFEFALAIVEALNGKEVAAQVKAPLVLKD

Cofilin-1 (IPI Acc. No. IPI00012011)
(SEQ ID NO: 6)
MASGVAVSDG VIKVFNDMKV RKSSTPEEVK KRKKAVLFCL

SEDKKNIILEEGKEILVGDV GQTVDDPYAT FVKMLPDKDC

RYALYDATYE TKESKKEDLV FIFWAPESAP LKSKMIYASS

KDAIKKKLTG IKHELQANCY EEVKDRCTLA EKLGGSAVIS LEGKPL 14-3-3 epsilon (IPI Acc. No. IPI00000816)
(SEQ ID NO: 7)
MDDREDLVYQ AKLAEQAERY DEMVESMKKV AGMDVELTVE

ERNLLSYAYK NVIGARRASW RIISSIEQKEENKGGEDKLK MIREY

RQMVE TELKLICCDI LDYLDKHLIP AANTGESKVF YYKMKGDYHR

YLAEFATGND RKEAAENSLV AYKAASDIAM TELPPTHPIR

LGLALNFSVFYYEILNSPDR ACRLAKAAFD DAIAELDTLS

EESYKDSTLI MQLLRDNLTLWTSDMQGDGE EQNKEALQDY EDENQ 14-3-3-gamma (SwissProt. Acc. No. P61981; IPI Acc. No. IPI00220642)
(SEQ ID NO: 8)
MVDREQLVQKARLAEQAERYDDMAAAMKNVTELNEPLSNEERNLLSVAYK

NVVGARRSSWRVISSIEQKTSADGNEKKIEMVRAYREKIEKELEAVCQDV

LSLLDNYLIKNCSETQYESKVFYLKMKGDYYRYLAEVATGEKRATVVESS

EKAYSEAHEISKEHMQPTHPIRLGLALNYSVFYYEIQNAPEQACHLAKTA

FDDAIAELDTLNEDSYKDSTLIMQLLRDNLTLWTSDQQDDDGGEGNN

Phosphoserine Phosphatase, (IPI Acc. No. IPI00019178; UNIPROT Acc. No. Q5EY1)
(SEQ ID NO: 9)
MYSHSELRKL FYSADAVCFD VDSTVIREEG IDELAKICGV

EDAVSEMTRRAMGGAVPFKA ALTERLALIQ PSREQVQRLI

AEQPPHLTPG IRELYSRLQERNVQVFLISG GFRSIVEHVA

SKLNIPATNV FANRLKSYFN GEYAGFDETQPTAESGGKGE

VIKLLKEKFH FKKIIMIGDG ATDMEACPPA DAFIGFGGNV

IRQQVKDNAK WYITDFVELL GELEE

Superoxide dismutase (IPI Acc. No. IPI00218733)
(SEQ ID NO: 10)
MATKAVCVLKGDGPVQGIINFEQKESNGPVKVWGSIKGLTEGLHGFHVHE

FGDNTAGCTSAGPHFNPLSRKHGGPKDEERHVGDLGNVTADKDGVADVSI

EDSVISLSGDHCIIGRTLVVHEKADDLGKGGNEESTKTGNAGSRLACGVI

GIAQ

Profilin-2 (IPI Acc. No. IPI00219468)
(SEQ ID NO: 11)
MAGWQSYVDNLMCDGCCQEAAIVGYCDAKYVWAATAGGVFQSITPIEIDM

IVGKDREGFFTNGLTLGAKKCSVIRDSLYVDGDCTMDIRTKSQGGEPTYN

VAVGRAGRVLVFVMGKEGVHGGGLNKKAYSMAKYLRDSGF

Beta-2 microglobulin (IPI Acc. No. IPI00004656)
(SEQ ID NO: 12)
MSRSVALAVLALLSLSGLEAIQRTPKIQVYSRHPAENGKSNFLNCYVSGF

HPSDIEVDLLKNGERIEKVEHSDLSFSKDWSFYLLYYTEFTPTEKDEYAC

RVNHVTLSQPKIVKWDRDM

Cytochrome C (IPI Acc. No. IPI100465315)
(SEQ ID NO: 13)
MGDVEKGKKIFIMKCSQCHTVEKGGKHKTGPNLHGLFGRKTGQAPGYSYT

AANKNKGIIWGEDTLMEYLENPKKYIPGTKMIFVGIKKKEERADLIAYLK

KATNE

Cystatin B (IPI Acc. No. IPI00021828)
(SEQ ID NO: 14)
MMCGAPSATQ PATAETQHIA DQVRSQLEEK ENKKFPVFKA

VSFKSQVVAGTNYFIKVHVGDEDFVHLRVF QSLPHENKPL

TLSNYQTNKA KHDELTYF

Macrophage migration inhibitory factor (MIF) (IPI Acc. No. IPI00293276)
(SEQ ID NO: 15)
MPMFIVNTNVPRASVPDGFLSELTQQLAQATGKPPQYIAVHVVPDQLMAF

GGSSEPCALCSLHSIGKIGGAQNRSYSKLLCGLLAERLRISPDRVYINYY

DMNAANVGWNNSTFA

FK506 binding protein (IPI Acc. No IPI00873810)
(SEQ ID NO: 16)
MGVQVETISPGDGRTFPKRGQTCVVHYTGMLEDGKKFDSSRDRNKPFKFM

LGKQEVIRGWEEGVAQMSVGQRAKLTISPDYAYGATGHPGIIPPHATLVF

DVELLKLE

Thioredoxin (IPI Acc. No. IPI00216298)
(SEQ ID NO: 17)
MVKQIESKTA FQEALDAAGD KLVVVDFSAT WCGPCKMIKP

FFHSLSEKYSNVIFLEYDVD DCQDVASECE VKCMPTFQFF

KKGQKVGEFSGANKEKELAT INELV

Galectin 3 (IPI Acc. No. IPI00465431)
(SEQ ID NO: 18)
MADNFSLHDA LSGSGNPNPQ GWPGAWGNQP AGAGGYPGAS

YPGAYPGQAPPGAYPGQAPP GAYPGAPGAY PGAPAPGVYP

GPPSGPGAYP SSGQPSATGAYPATGPYGAP AGPLIVPYNL

PLPGGVVPRM LITILGTVKP NANRIALDFQRGNDVAFHFN

PRFNENNRRV IVCNTKLDNN WGREERQSVF PFESGKPFKI

QVLVEPDHFK VAVNDAHLLQ YNHRVKKLNE ISKLGISGDI

DLTSASYTMI

Transferrin (TRFE_HU Serotransferrin precursor)
(Acc. No. P02787)
(SEQ ID NO: 19)
MRLAVGALLV CAVLGLCLAV PDKTVRWCAV SEHEATKCQS

FRDHMKSVIPSDGPSVACVK KASYLDCIRA IAANEADAVT

LDAGLVYDAY LAPNNLKPVVAEFYGSKEDP QTFYYAVAVV

KKDSGFQMNQ LRGKKSCHTG LGRSAGWNIPIGLLYCDLPE

PRKPLEKAVA NFFSGSCAPC ADGTDFPQLC QLCPGCGCST

LNQYFGYSGA FKCLKDGAGD VAFVKHSTIF ENLANKADRD

QYELLCLDNTRKPVDEYKDC HLAQVPSHTV VARSMGGKED

LIWELLNQAQ EHFGKDKSKEFQLFSSPHGK DLLFKDSAHG

FLKVPPRMDA KMYLGYEYVT AIRNLREGTCPEAPTDECKPVKWCALSH

HE RLKCDEWSVN SVGKIECVSA ETTEDCIAKIMNGEADAMSL

DGGFVYIAGK CGLVPVLAEN YNKSDNCEDT PEAGYFAVAV

VKKSASDLTW DNLKGKKSCH TAVGRTAGWN IPMGLLYNKI

NHCRFDEFFSEGCAPGSKKD SSLCKLCMGS GLNLCEPNNK

EGYYGYTGAF RCLVEKGDVAFVKHQTVPQN TGGKNPDPWA

KNLNEKDYEL LCLDGTRKPV EEYANCHLARAPNHAVVTRK

DKEACVHKIL RQQQHLFGSN VTDCSGNFCL FRSETKDLLF

RDDTVCLAKLHDRNTYEKYL GEEYVKAVGN LRKCSTSSLL

EACTFRRP

EF-1-gamma (EF1G-HU Elongation factor 1-gamma)
(Acc. No. P26641)
(SEQ ID NO: 20)
MAAGTLYTYP ENWRAFKALI AAQYSGAQVR VLSAPPHFHF

GQTNRTPEFLRKFPAGKVPA FEGDDGFCVF ESNAIAYYVS

NEELRGSTPE AAAQVVQWVSFADSDIVPPA STWVFPTLGI

MHITNKQATEN AKEEVRRILG LLDAYLKTRTFLVGERVTLA

DITVVCTLLW LYKQVLEPSF RQAFPNTNRW FLTCINQPQF

RAVLGEVKLC EKMAQFDAKK FAETQPKKDT PRKEKGSREE

KQKPQAERKEEKKAAAPAPE EEMDECEQAL AAEPKAKDPF

AHLPKSTFVL DEFKRKYSNEDTLSYALPYF WEHFDKDGWS

LWYSEYRFPE ELTQTFMSCN LITGMFQRLDKLRKNAFASV

ILFGTNNSSS ISGVWVFRGQ ELAFPLSPDW QVDYESYTWR

KLDPGSEETQ TLVREYFSWE GAFQHVGKAF NQGKIFK

Galectin-3 binding protein (LG3BP_HU galectin 3
binding protein precursor) (Acc. No. Q08380
(SEQ ID NO: 21)
MTPPRLFWVW LLVAGTQGVN DGDMRLADGG ATNQGRVEIF

YRGQWGTVCD NLWDLTDASV VCRALGFENA TQALGRAAFG

QGSGPIMLDEVQCTGTEASL ADCKSLGWLK SNCRHERDAG

VVCTNETRST HTLDLSRELSEALGQIFDSQ RGCDLSISVN

VQGEDALGFC GHTVILTANL EAQALWKEPGSNVTMSVDAE

CVPMVRDLLR YFYSRRIDIT LSSVKCFHKL ASAYGARQLQ

GYCASLFAIL LPQDPSFQMP LDLYAYAVAT GDALLEKLCL

QFLAWNFEALTQAEAWPSVP TDLLQLLLPR SDLAVPSELA

LLKAVDTWSW GERASHEEVEGLVEKIRFPM MLPEELFELQ

FNLSLYWSHE ALFQKKTLQA LEFHTVPFQLLARYKGLNLT

EDTYKPRIYT SPTWSAFVTD SSWSARKSQL VYQSRRGPLV

KYSSDYFQAP SDYRYYPYQS FQTPQHPSFL FQDKRVSWSL

VYLPTIQSCWNYGFSCSSDE LPVLGLTKSG GSDRTIAYEN

KALMLCEGLF VADVTDFEGW KAAIPSALDT NSSKSTSSFP

CPAGHFNGFR TVIRPFYLTN SSGVD

As used herein, a chemorepellant has "substantial identity" to another protein when the chemorepellant has an amino acid sequence that has at least about 60 percent sequence identity, at least about 70 percent sequence identity, at least about 80 percent sequence identity, at least about 85 percent sequence identity, at least about 85 to 95 percent sequence identity, at least about 90 to about 95 percent sequence identity, at least about 98 percent sequence identity, or at least about 99 percent sequence identity to the amino acid sequence of the other protein. The terms "sequence identity" or "identity" in reference to a sequence refers to sequence identity between two amino acid sequences or between two nucleotide sequences. Identity can be determined by comparing a position in each sequence which may be aligned for purposes of comparison. The terms "sequence homology" or "homology" in reference to a sequence refers to sequence homology between two amino acid sequences or two nucleotide sequences. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

A "chemoattractant" is an agent or stimulus that induces, elicits or triggers positive chemotaxis (movement towards an agent or stimulus) by a migratory cell.

As used herein the terms "induce," "elicit," and "trigger," when referring to the activity of a chemorepellant or chemoattractant with respect to negative or positive chemotaxis, carry the same meaning.

The activity of the chemorepellant released from a cancer cell is inhibited when the ability of the chemorepellant to induce negative chemotaxis of the immune cell is suppressed or decreased. According to the current invention, the activity of the chemorepellant released from the cancer cell can be inhibited by any means that suppresses negative chemotaxis of the immune cell or that induces positive chemotaxis of the immune cell toward the cancer cell. For example, the activity of the chemorepellant can be inhibited by administering an agent that inhibits the activity of the chemorepellants. Such agents, include, but are not limited to, small molecules, proteins, antibodies, and antisense nucleic acids.

In one embodiment, the activity of the chemorepellant released from a cancer cell is inhibited when the release of the chemorepellant is suppressed or decreased. In another embodiment, the activity of the chemorepellant released from a cancer cell is inhibited by administering an agent that binds to the chemorepellant and inhibits its activity. In some embodiments, the activity of the chemorepellant is inhibited by administering an antibody that binds the chemorepellant and inhibits chemorepellant activity. The term "antibody" as used herein refers to a polypeptide comprising a framework region from an immunoglobulin gene or fragments thereof that specifically binds and recognizes an antigen. The term antibody, as used herein, includes antibody fragments either produced by modification of whole antibodies, or those synthesized de novo using recombinant DNA methodologies (e.g., single chain Fv) (scFv) or those identified using phase display libraries (see, for example, McCafferty et al. (1990) Nature 348:552-554). The term antibody also encompasses both monoclonal and polyclonal antibodies. The terms polyclonal and monoclonal refer to the degree of homogeneity of an antibody preparation, and are not intended to be limited to particular methods of production. In one embodiment, the antibody does not bind other proteins or molecules other than the chemorepellant.

Antibodies can be raised against an appropriate immunogen, including a chemorepellant released from a cancer cell or a fragment thereof. Preparation of immunizing antigen, and polyclonal and monoclonal antibody production can be performed using any suitable technique. A variety of methods have been described (see e.g., Kohler et al., Nature, 256:495-497 (1975)) and Eur. J. Immunol. 6:511-519 (1976)); Milstein et al., Nature 266:550-552 (1977)); Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); and Current Protocols In Molecular Biology, Vol. 2 (Supplement 27, Summer '94), Ausubel, F. M. et al., Eds., (John Wiley & Sons: New York, N.Y.), Chapter 11, 1991); the teachings of each of which are incorporated herein by reference). Other suitable methods of producing or isolating antibodies of the requisite specificity can used, including, for example, methods which select recombinant antibody from a library, or which rely upon immunization of transgenic animals (e.g., mice) capable of producing a full repertoire of human antibodies (see e.g., Jakobovits et al., Proc. Natl. Acad. Sci. USA, 90:2551 2555 (1993)); Jakobovits et al., Nature, 362:255 258 (1993)); Lonberg et al., U.S. Pat. No. 5,545,806; and Surani et al., U.S. Pat. No. 5,545,807; the teachings of which are each incorporated herein by reference). Single-chain antibodies, and chimeric, humanized or primatized (CDR-grafted), or veneered antibodies, as well as chimeric, CDR-grafted or veneered single-chain antibodies, comprising portions derived from different species, and the like are also encompassed by the present invention and the term "antibody." The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan et al., EP 0 519 596 A1. See also, Newman et al., BioTechnology, 10:1455 1460 (1992), regarding primatized antibody, and Ladner et al., U.S. Pat. No. 4,946,778 and Bird et al., Science, 242:423 426 (1988) regarding single-chain antibodies. In addition, antigen-binding fragments of antibodies, including fragments of chimeric, humanized, primatized, veneered or single-chain antibodies, can also be produced, including, but not limited to, Fv, Fab, Fab' and F(ab')$_2$ fragments are encompassed by the invention.

In another embodiment, the activity of the chemorepellant is inhibited by administering an antisense nucleic acid. In this context, the chemorepellant antisense nucleic acid comprises at least six nucleotides that are antisense to a gene or cDNA encoding the chemorepellant released from a cancer cell or a portion thereof. The antisense nucleic acid is capable of hybridizing to a portion of an RNA encoding the chemorepellant. The antisense nucleic acid is a double-stranded or single-stranded oligonucleotide, RNA or DNA or a modification or derivative thereof, and can be directly administered to a cell or produced intracellularly by transcription of exogenous, introduced sequences. In one embodiment, the antisense nucleic acid has from about 6 to about 50 nucleotides. In other embodiment, the antisense nucleic acid has at least 10 nucleotides, at least 15 nucleotides, at least 100 nucleotides, or at least 200 nucleotides. The antisense nucleic acid can be DNA or RNA or chimeric mixtures or derivatives or modified versions thereof and can be single-stranded or double-stranded. In addition, the antisense molecules can be polymers that are nucleic acid mimics, such as PNA, morpholino oligos, and LNA. Other types of antisense molecules include short double-stranded RNAs, known as siRNAs, and short hairpin RNAs, and long dsRNA (greater than 50 base pairs).

In yet another embodiment, the activity of the chemorepellant is inhibited by administering a ribozyme molecule that is designed to catalytically cleave gene mRNA transcripts encoding the chemorepellant. Ribozymes thus prevents translation of the target mRNA and prevents expression of the gene product. Ribozymes are enzymatic RNA molecules capable of catalyzing the specific cleavage of RNA. The mechanism of ribozyme action involves sequence-specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage.

In another embodiment, the invention is a method of treating cancer in a patient suffering therefrom comprising inducing migration of an immune cell toward a cancer cell by inhibiting the activity of a chemorepellant released from a cancer cell. "Treating" or "treatment" includes preventing or delaying the onset of the symptoms, complications, or biochemical indicia of a disease, alleviating or ameliorating the symptoms or arresting or inhibiting further development of the disease, condition, or disorder. A "patient" refers to a human subject in need of treatment. In specific embodiments, the cancer is a solid tumor. In one embodiment, the solid tumor is selected from the group consisting of colon, prostate, breast, lung, skin, liver, bone, pancreas, ovary, testis, bladder, kidney, brain, head and neck cancer. As used herein, a "therapeutically effective amount" in reference to inhibition of a chemorepellant is an amount sufficient to inhibit negative migration of an immune cell and ameliorate a disease or condition of a patient or achieve a desired outcome. In reference to inducing chemotaxis, a "therapeutically effective amount" is an amount sufficient to induce negative migration of a migratory cell and ameliorate a disease or condition of a patient or achieve a desired outcome.

As used herein, "migratory cells" are those cells which are capable of movement from one place to another in response to a stimulus. Human migratory cells include those involved in the processes of cancer, immunity, angiogenesis or inflammation and also include those identified to play a role in other disease states or conditions. Migratory cells include, but are not limited to, immune cells, hematopoietic cells, neural cells, epithelial cells, mesenchymal cells, stem cells, germ cells and cells involved in angiogenesis.

Immune cells include, but are not limited to, monocytes, Natural Killer (NK) cells, dendritic cells (which could be immature or mature), subsets of dendritic cells including myeloid, plasmacytoid (also called lymphoid) or Langerhans; macrophages such as histiocytes, Kupffer's cells, alveolar macrophages or peritoneal macrophages; neutrophils, eosinophils, mast cells, basophils; B cells including plasma B cells, memory B cells, B-1 cells, B-2 cells; CD45RO (naive T), CD45RA (memory T); CD4 Helper T Cells including Th1, Th2 and Tr1/Th3; CD8 Cytotoxic T Cells, Regulatory T Cells and Gamma Delta T Cells.

Hematopoietic cells include, but are not limited to, pluripotent stem cells, multipotent progenitor cells and/or progenitor cells committed to specific hematopoietic lineages. The progenitor cells committed to specific hematopoietic lineages can be of T cell lineage, B cell lineage, dendritic cell lineage, neutrophil lineage, Langerhans cell lineage and/or lymphoid tissue-specific macrophage cell lineage. The hematopoietic cells can be derived from a tissue such as bone marrow, peripheral blood (including mobilized peripheral blood), umbilical cord blood, placental blood, fetal liver, embryonic cells (including embryonic stem cells), aortal-gonadal-mesonephros derived cells, and lymphoid soft tissue. Lymphoid soft tissue includes the thymus, spleen, liver, lymph node, skin, tonsil and Peyer's patches. In other embodiments, hematopoietic cells can be derived from in vitro cultures of any of the foregoing cells, and in particular in vitro cultures of progenitor cells.

Neural cells are cells of neural origin and include neurons and glia and/or cells of both central and peripheral nervous tissue.

Epithelial cells include cells of a tissue that covers and lines the free surfaces of the body. Such epithelial tissue includes cells of the skin and sensory organs, as well as the specialized cells lining the blood vessels, gastrointestinal tract, air passages, lungs, ducts of the kidneys and endocrine organs.

Mesenchymal cells include, but are not limited to, cells that express typical fibroblast markers such as collagen, vimentin and fibronectin.

Cells involved in angiogenesis are cells that are involved in blood vessel formation and include cells of endothelial origin and cells of mesenchymal origin.

Germ cells are cells specialized to produce haploid gametes.

In certain embodiment, the human migratory cell is an immune cell. In other embodiments, the immune cell is selected from the group consisting of lymphocytes, monocytes, neutrophils, eosinophils and mast cells. In a further embodiment, the immune cell is a neutrophil or an eosinophil.

As used herein, the terms "contact" or "contacting" means the act of touching or bringing together two entities or things in such proximity as will allow an influence of at least one on the other. The definition, while inclusive of physical contact is not so limited.

Based on their ability to induce negative chemotaxis, the chemorepellant proteins or biologically active fragments thereof as described herein are useful for inhibiting the induction of chemotaxis of migratory cells toward a chemotactic site. In one embodiment, the chemorepellant comprises a sequence that has substantial identity to the amino acid sequence of a protein selected from the proteins set forth in Tables 1 to 9, or to a biologically active fragment thereof. In some embodiment, the chemorepellant protein comprises a sequence that has substantial identity to a protein selected from the proteins set forth in Tables 10 to 11, or to a biologically active fragment thereof. In another embodiment, the protein comprises a sequence that has substantial identity to the sequence of a protein selected from the group consisting of actin, 14-3-3 zeta/delta, apolipoprotein A1, hemopexin, PARK7, cofilin-1, 14-3-3 epsilon, 14-3-3-gamma, phosphoserine phosphatase, superoxide dismutase, profilin-2, beta-2 microglobulin, cytochrome c, cystatin B, macrophage migration inhibitory factor (MIF), FK506 binding protein, thioredoxin, galectin 3, human transferrin, human EF-1-gamma and human galectin 3 binding protein, or to a biologically active fragment of any of thereof. As used herein, a "chemotactic site" is a site that induces positive chemotaxis of migratory cells. Chemotactic sites include sites of inflammation, medical implants, transplants and angiogenesis.

The chemorepellants described herein are useful for inhibiting the induction of chemotaxis of migratory cells toward a site of inflammation. Inhibiting migratory cell chemotaxis toward a site of inflammation can result in a reduction or amelioration of an inflammatory response in situations such as bacterial infection, tissue injury-induced inflammation (e.g., ischemia-reperfusion injury), complement-induced inflammation, oxidative stress (e.g., hemodialysis), immune complex-induced inflammation (e.g., antibody-mediated glomerunephritis), cytokine-induced inflammation (e.g., rheumatoid arthritis), antineutrophil cytoplasmic antibodies and vasculitis (e.g, autoimmunity against neutrophil components), genetic disorders of neutrophil regulations (e.g., hereditary periodic fever syndromes), implant related inflammation, and cystic fibrosis.

In certain embodiments, the invention is a method of treating an inflammatory condition in a patient suffering therefrom comprising administering to said patient a therapeutically effective amount of a chemorepellant described herein. In certain other embodiments, the invention is a method of treating an inflammatory condition in a patient suffering therefrom comprising administering to said patient a therapeutically effective amount of a chemorepellant described herein. Inflammatory conditions include, but are not limited to, appendicitis, peptic, gastric or duodenal ulcers, peritonitis, pancreatitis, acute or ischemic colitis, diverticulitis, epiglottitis, achalasia, cholangitis, cholecystitis, hepatitis, inflammatory bowel disease (including, for example, Crohn's disease and ulcerative colitis), enteritis, Whipple's disease, asthma, chronic obstructive pulmonary disease, acute lung injury, ileus (including, for example, post-operative ileus), allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopic silicovolcanoconiosis, alvealitis, bronchiolitis, pharyngitis, pleurisy, sinusitis, influenza, respiratory syncytial virus, herpes, disseminated bacteremia, Dengue fever, candidiasis, malaria, filariasis, amebiasis, hydatid cysts, burns, dermatitis, dermatomyositis, urticaria, acne, vasulitis, angiitis, endocarditis, arteritis, atherosclerosis, thrombophlebitis, pericarditis, myocarditis, myocardial ischemia, periarteritis nodosa, rheumatic fever, Alzheimer's disease, celiac disease, congestive heart failure, adult respiratory distress syndrome, meningitis, encephalitis, multiple sclerosis, cerebral infarction, cerebral embolism, Guillan-Barre syndrome, neuritis, neuralgia, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcet's syndrome, allograft rejection, graft-versus-host disease, Type I diabetes, ankylosing spondylitis, Berger's disease, Type II diabetes, Retier's syndrome, Hodgkins disease and injection site reaction.

Injection site reaction is a term generally used to describe inflammation in and around a site of injection. Injection site reaction has been observed with the injection of numerous pharmaceutical agents including, but not limited, chemotherapeutic drugs, immunomodulator drugs, and vaccines. The present invention encompasses a method for the treatment or reduction of injection site reaction comprising administration of a chemorepellant described herein to the injection site. The chemorepellant can, for example, be administered before, during or after injection. In some embodiments, exenatide or analog thereof can be administered topically at the site of the injection.

In another embodiment, the invention is a method of inhibiting positive chemotaxis toward a medical implant. The medical implant can be contacted or coated with a chemorepellant described herein. The proteins can also be administered locally at the site of the medical implant. A medical implant is defined as a device or entity implanted into a surgically or naturally formed cavity of the body. Medical implants include, but are not limited to, stents, pacemakers, pacemaker leads, defibrillators, drug delivery devices, sensors, pumps, embolization coils, sutures, electrodes, cardiovascular implants, arterial stents, heart valves, orthopedic implants, dental implants, bone screws, plates, catheters, cannulas, plugs, fillers, constrictors, sheets, bone anchors, plates, rods, seeds, tubes, or portions thereof. In addition to the chemorepellant, the medical implant can be coated with a cell-growth potentiating agent, an anti-infective agent and/or an anti-inflammatory agent.

In yet another embodiment, the invention is a method of inhibiting positive chemotaxis toward an organ transplant or tissue graft. Organ transplants and tissue grants include, but are not limited to, renal, pancreatic, hepatic, lymphoid and cardiac grafts and organs. Lymphoid grafts include a splenic graft, a lymph node derived graft, a Peyer's patch derived graft, a thymic graft and a bone marrow derived graft. In an additional embodiment, the invention is a method of treating a patient suffering from transplant or graft rejection comprising administering an inventive chemorepellant.

As discussed above, the inventive chemorepellants can be used to inhibit chemotaxis toward a site of angiogenesis. A site of angiogenesis is a site where blood vessels are being formed. In one embodiment, the invention is a method of inducing negative chemotaxis of endothelial cells away from a site of angiogenesis. The invention also encompasses a method of inhibiting angiogenesis in a patient in need thereof comprising administering an inventive chemorepellant In a further embodiment, the invention is a method of treating cancer or a tumor comprising administering an inventive chemorepellant in an amount effective to inhibit angiogenesis. According to another aspect of the invention, a method of inhibiting endothelial cell migration to a tumor site in a subject is provided. The method involves locally administering to or contacting an area surrounding a tumor site in need of such treatment an inventive chemorepellant in an amount effective to inhibit endothelial cell migration into the tumor site in the subject.

Exemplary cancers and tumors that can be treated according to the methods of the invention include, for example, biliary tract cancer; brain cancer including glioblastomas and medulloblastomas; breast cancer; cervical cancer; choriocarcinoma; colon cancer; endometrial cancer; esophageal cancer, gastric cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer (hepatocarcinoma); lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma [teratomas, choriocarcinomas]), stromal tumors and germ cell tumors; thyroid cancer, including thyroid adenocarcinoma and medullar carcinoma; and renal cancer including adenocarcinoma and Wilms tumor.

The invention also encompasses a method of contraception in a patient in need thereof comprising administering an inventive chemorepellant in an amount effective to inhibit migration of germ cells in the subject. According to another aspect of the invention, a method of treating infertililty and premature labor is provided. The method comprises administering a compound described above in an amount effective to inhibit immune cells from migrating close to a germ cell in the subject.

The treatment methods disclosed herein involve administering, either locally or systemically, to a selected site in a subject in need of such a treatment a chemorepellant of the invention in an amount effective to induce negative chemotaxis of a human migratory cell or an inhibitor of a chemorepellant in an amount effect to suppress negative chemotaxis of an immune cell. For example, a "therapeutically effective amount" in reference to the treatment of an inflammatory condition encompasses an amount sufficient to induce negative chemotaxis of an immune cell and/or ameliorate a symptom of the inflammatory condition.

In certain embodiments, the chemorepellant can be co-administered with a second agent (e.g., another chemoattractant or with any drug or agent which is not itself a chemoattractant). Co-administered agents, compounds, chemoattractants or therapeutics need not be administered at exactly the same time. In certain embodiments, however, the chemorepellant is administered substantially simultaneously as the second agent. By "substantially simultaneously," it is meant that the chemorepellant is administered before, at the same time, and/or after the administration of the second agent. Second agents include, for example, anti-inflammatory agents, anti-cancer agents, anti-infective agents, immune therapeutics (immunosuppresants) and other therapeutic compounds. A second agent can be chosen based on the condition or disease to be treated. For example, in a method of treating cancer or a tumor, the chemorepellant can be administered with an anti-cancer agent. Similarly, in a method of treating an inflammatory condition, the chemorepellant can be administered with an anti-inflammatory agent, an anti-infective agent or an immunosuppressant.

An anti-infective agent is an agent which reduces the activity of or kills a microorganism and includes: Aztreonam; Chlorhexidine Gluconate; Imidurea; Lycetamine; Nibroxane; Pirazmonam Sodium; Propionic Acid; Pyrithione Sodium; Sanguinarium Chloride; Tigemonam Dicholine; Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin lydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacil; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz: Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet;

Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin; Difloxacin Hydrochloride; Lauryl Isoquinolinium Bromide; Moxalactam Disodium; Ornidazole; Pentisomicin; and Sarafloxacin Hydrochloride.

Exemplary anti-cancer agents include Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatini; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Podofilox; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxotere; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporlin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate Virlrosidine Sulfate; Vinzolidine Sulfate; Vorozole; Zeniplatin; Zinostatin; and Zorubicin Hydrochloride. Exemplary immunosuppressants include Azathioprine; Azathioprine Sodium; Cyclosporine; Daltroban; Gusperimus Trihydrochloride; Sirolimus; and Tacrolimus. Exemplary anti-inflammatory agents include Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; and Zomepirac Sodium.

As used herein, "treatment" and/or "treating" refer to therapeutic treatment as well as prophylactic treatment or preventative measures. The chemorepellant and/or other therapeutic (such as an antibody to the chemorepellant) can be administered in pharmaceutical compositions comprising a pharmaceutically acceptable carrier or excipient. The excipient can be chosen based on the expected route of administration of the composition in therapeutic applications. The route of administration of the composition depends on the condition to be treated. Routes of administration include, but are not limited to, parenteral, topic, oral, intramuscular, intravenous administration. The route of administration and the dosage of the composition to be administered can be determined by the skilled artisan without undue experimentation in conjunction with standard dose-response studies.

Relevant circumstances to be considered in making those determinations include the condition or conditions to be treated, the choice of composition to be administered, the age, weight, and response of the individual patient, and the severity of the patient's symptoms. In one embodiment, the chemorepellant or a composition thereof is administered locally.

The therapeutic compositions used in the inventive methods can be administered parenterally such as, for example, by intravenous, intramuscular, intrathecal, or subcutaneous injection. Parenteral administration can be accomplished by incorporating the therapeutic compositions of the present invention into a solution or suspension. Such solutions or suspensions may also include sterile diluents such as water for injection, saline solution, fixed oils, polyethylene glycols, glycerine, propylene glycol, or other synthetic solvents. Parenteral formulations may also include antibacterial agents such as, for example, benzyl alcohol or methyl parabens, antioxidants such as, for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes, or multiple dose vials made of glass or plastic.

The invention is illustrated by the following examples which are not meant to be limiting in any way.

EXEMPLIFICATION

Example 1

Identification of Modulators of Cell Migration Present in Tumor Environments Objective: To identify the agents present in tumor microenvironments that have the ability to modulate the migration of immune cell subsets.

Materials and Methods:

Cystic fluid samples: Fluids from ovarian carcinoma patients were collected during surgical procedures under a signed informed consent. Fluids were centrifuged to remove the debris. The supernatants were supplemented with cocktail of protease inhibitors and divided into aliquots and stored at −80 C till further processing. Samples were evaluated to study their effects on migration of neutrophils in transwell migration assays in Boyden chambers for their chemoattraction (CA) and chemorepulsion (CR) activities as described below.

Chromatographic separation: Cystic fluid (0.2 ml at 65 mg/ml) was loaded on a Superdex 200 10/300 GL column (GE Healthcare) and fractionated at the rate of 0.5 ml/min. Fractions (1 ml) were collected in tubes preloaded with 10 µl of 100× concentration Complete EDTA-free Protease Inhibitor Cocktail (Roche). These fractions were evaluated for CA CR activities in transwell migration assays described below.

One and two dimensional SDS-PAGE analysis: Fractions collected from S-200 chromatography with CR activity and the adjacent fractions without CR activity were further fractionated by one and two dimensional SDS-PAGE. Proteins band and/or spots differentially present in S-200 fractions with CR activity were excised manually, digested with trypsin, and subjected to either LC-MS/MS (1-D bands) or MALDI (2-D spots) analysis.

The chemorepulsive activity of the cystic fluid, fractions collected from S-200 chromatography and the proteins listed below was determined as follows:

Prior to beginning the assay, the following were prepared:

0.5% Fetal Calf Serum (FCS) in Iscove's Modified Dulbecco's Medium (IMDM) (Assay Medium) (Both from ATCC).

Migratory cells at a concentration of $2 \times 10^7$ cells/ml in Assay Medium.

Four serial (3-fold) dilutions of the ligand of interest in Assay Medium.

The assay plates are Neuroprobe ChemoTx plates, part number 206-3 (3 um pore size) for neutrophils.

31 µl of the following solutions were pipetted into each well:

For media controls and for chemorepulsion samples, Assay Medium was used.

For chemoattraction samples, appropriate dilution of ligand was used.

The membrane was carefully placed onto the plate, starting at one side and then slowly lowering the other edge onto the plate.

29 µl of the following were pipetted onto the top of each circle:

For media controls and chemoattraction samples, use Assay Medium.

For chemorepulsion samples, use the appropriate dilution of ligand.

2 µl of cells (40,000 cells) were added to each bubble of liquid from step 7.

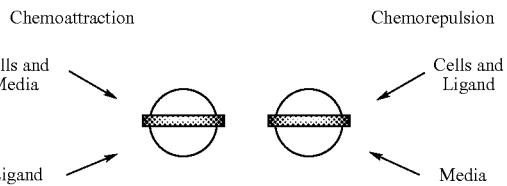

The plate was covered with the supplied lid and incubated for the desired time at 37° C. in 5% $CO_2$. Unless otherwise indicated, the incubation time was 1 hour for neutrophils and 3 hours for T cells. For monocytes and B cells, the incubation time was 2 hours. After the desired assay time, the liquid was removed from the top of the plate using a Kimwipe.

The membrane was carefully removed from the top of the plate and discarded. The plate was examined under a microscope to look for ligand crystallization, contamination and overall migration.

White read plates were preloaded with 25 ul PBS.

Using a multichannel pipettor, 5 ul of Cell Titer Glo (Promega #G7572) was added to each well.

Using a multichannel pipettor set at 30 ul, lysed cell solution was transferred to white read plates pre-loaded with PBS.

The plate was read using the BioTek Synergy4 plate reader in order to quantify the number of migrated cells.

Results:

From mass spectrometry (MS) analysis, 86 proteins in the chemorepulsion active chromatography fraction have been identified which are represented in the following table.

TABLE 1

| Proteins present in specific active fragments of S200 | |
|---|---|
| Identified Proteins | Accession Number |
| A1BG Alpha-1B-glycoprotein precursor | IPI00022895 |
| A2M Alpha-2-macroglobulin precursor | IPI00478003 |

TABLE 1-continued

Proteins present in specific active fragments of S200

| Identified Proteins | Accession Number |
|---|---|
| ACTA2 Actin, aortic smooth muscle | IPI00008603 (+9) |
| ACTB Actin, cytoplasmic 1 | IPI00021439 (+2) |
| AFM Afamin precursor | IPI00019943 |
| AHSG Alpha-2-HS-glycoprotein precursor | IPI00022431 (+1) |
| ALB Isoform 1 of Serum albumin precursor | IPI00745872 (+1) |
| Alpha 2 HS-glycoprotein | P02765; gi: 112910 |
| ANPEP Aminopeptidase N | IPI00221224 |
| APOA1 Apolipoprotein A-I precursor | IPI00021841 (+1) |
| apolipoprotein A-1 | P02647 |
| apolipoprotein A-IV | P06727 |
| C1RL Complement C1r subcomponent-like protein precursor | IPI00009793 (+2) |
| C2 Complement C2 precursor (Fragment) | IPI00303963 |
| C3 Complement C3 precursor (Fragment) | IPI00783987 |
| C4A Complement component 4A | IPI00643525 |
| C9 Complement component C9 precursor | IPI00022395 |
| carbonic anhydrase 1 | P00915 |
| CD163 Isoform 1 of Scavenger receptor cysteine-rich type 1 protein M130 precursor | IPI00104074 (+3) |
| CFB Isoform 1 of Complement factor B precursor (Fragment) | IPI00019591 |
| CP Ceruloplasmin precursor | IPI00017601 |
| EEF1A2 Elongation factor 1-alpha 2 | IPI00014424 (+3) |
| F2 Prothrombin precursor (Fragment) | IPI00019568 |
| GC Vitamin D-binding protein precursor | IPI00555812 (+1) |
| GSN Isoform 1 of Gelsolin precursor | IPI00026314 (+1) |
| H2AFV Histone H2AV | IPI00018278 (+15) |
| HABP2 Hyaluronan-binding protein 2 precursor | IPI00746623 |
| HBA2; HBA1 Hemoglobin subunit alpha | IPI00410714 (+1) |
| HBB Hemoglobin subunit beta | IPI00654755 (+1) |
| hemoglobin beta | P68871 |
| hemopexin | P02790 |
| HIST1H1D Histone H1.3 | IPI00217466 (+2) |
| HIST1H2AM; HIST1H2AG; HIST1H2AJ; HIST1H2AL; HIST1H2AK; HIST1H2AI Histone H2A type 1 | IPI00291764 (+9) |
| HIST2H3A; HIST2H3C; HIST2H3D Histone H3.2 | IPI00171611 (+7) |
| HIST2H4A; HIST1H4C; HIST1H4A; HIST1H4I; HIST1H4E; HIST1H4F; HIST1H4K; HIST1H4H; HIST4H4; HIST1H4L; HIST1H4D; HIST1H4J; HIST2H4B; HIST1H4B Histone H4 | IPI00453473 |
| HPX Hemopexin precursor | IPI00022488 |
| HRG Histidine-rich glycoprotein precursor | IPI00022371 |
| HRNR Hornerin | IPI00398625 (+2) |
| IGFALS Insulin-like growth factor-binding protein complex acid labile chain precursor | IPI00020996 |
| IGHD IGHD protein | IPI00418422 (+2) |
| IGHG1 IGHG1 protein | IPI00448925 |
| IGHG1 IGHG1 protein | IPI00815926 |
| IGHG3 IGHG3 protein | IPI00472345 |
| IGHM; IGH@ IGHM protein | IPI00472610 |
| IGHV1OR15-1 Ig heavy chain V-I region V35 precursor | IPI00009792 |
| IGHV3OR16-13; IGHA1 IGHA1 protein | IPI00061977 |
| IGHV3OR16-13; IGHA1 IGHA1 protein | IPI00430842 |
| IGHV4-31 IGHV4-31 protein | IPI00784822 |
| IGKV1-5 IGKV1-5 protein | IPI00419424 (+19) |
| IGL@ IGL@ protein | IPI00154742 |
| ITIH2 Inter-alpha-trypsin inhibitor heavy chain H2 precursor | IPI00305461 (+1) |
| ITIH4 Isoform 1 of Inter-alpha-trypsin inhibitor heavy chain H4 precursor | IPI00294193 |
| ITIH4 Isoform 2 of Inter-alpha-trypsin inhibitor heavy chain H4 precursor | IPI00218192 (+3) |
| KNG1 Isoform LMW of Kininogen-1 precursor | IPI00215894 (+1) |
| KPRP Keratinocyte proline-rich protein | IPI00514908 |
| KRT1 Keratin, type II cytoskeletal 1 | IPI00220327 (+1) |
| KRT10 Keratin, type I cytoskeletal 10 | IPI00009865 (+1) |
| KRT14 Keratin, type I cytoskeletal 14 | IPI00384444 |
| KRT16 Keratin, type I cytoskeletal 16 | IPI00217963 |
| KRT2 Keratin, type II cytoskeletal 2 epidermal | IPI00021304 (+1) |
| KRT5 Keratin, type II cytoskeletal 5 | IPI00009867 |
| KRT6A Keratin, type II cytoskeletal 6A | IPI00300725 |
| KRT9 Keratin, type I cytoskeletal 9 | IPI00019359 (+1) |
| LDHA Isoform 1 of L-lactate dehydrogenase A chain | IPI00217966 (+2) |
| LUM Lumican precursor | IPI00020986 (+1) |
| LYZ Lysozyme C precursor | IPI00019038 (+1) |
| plasma retinol-binding protein | P02753 |
| SERPINA1 Isoform 1 of Alpha-1-antitrypsin precursor | IPI00553177 |
| SERPINA3 Alpha-1-antichymotrypsin precursor | IPI00550991 (+1) |
| SERPINA7 Thyroxine-binding globulin precursor | IPI00292946 |
| SERPIND1 Serpin peptidase inhibitor, clade D (Heparin cofactor), member 1 | IPI00292950 (+1) |
| SERPINF2 SERPINF2 protein | IPI00029863 (+1) |
| SLPI Antileukoproteinase precursor | IPI00008580 |
| sp_ALBU_BOVIN | IPIsp_ALBU_BOVIN |
| sp_ANT3_HUMAN | IPIsp_ANT3_HUMAN |
| sp_TRYP_PIG | IPIsp_TRYP_PIG |
| TF Serotransferrin precursor | IPI00022463 (+2) |
| transthyretin | P02766 |
| Putative uncharacterized protein DKFZp686C15213 | IPI00426051 |
| cDNA FLJ78387 | IPI00876888 |
| Ig heavy chain V-III region CAM | IPI00382482 |
| Single-chain Fv (Fragment) | IPI00470652 |
| uncharacterized protein ENSP00000375035 | IPI00735451 |
| uncharacterized protein ENSP00000375026 | IPI00829845 |
| YWHAZ 14-3-3 protein zeta/delta | IPI00021263 (+1) |
| zinc-alpha-2-glycoprotein | P25311 |

Some of these proteins were evaluated individually and in combinations for their effects on CA and CR activity. Of these proteins, actin, 14-3-3 zeta/delta, apolipoprotein A1 and hemopexin showed the greatest CA and/or CR activities. FIGS. 1 through 6 represent the effect of whole cyst fluid, Superdex 200 fractions, Actin and 14-3-3 individually, the same two proteins assayed in combination, Apolipoprotein A1, and hemopexin on migration of human neutrophils in CA and CR modes.

Legends for the Figures:

FIG. 1: Effect of Cystic fluid on migration of human neutrophils. Human neutrophils were tested at different concentrations of cyst fluid: neat (undiluted), and at 1:3, 1:10 and 1:30 diluted in media. Both chemo attraction (CA) and chemorepulsion were measured using a Boyden chamber transwell migration assay. Cystic fluid has efficiently repelled human neutrophils as studied by transwell migration assays at all concentrations tested.

Figure 2:
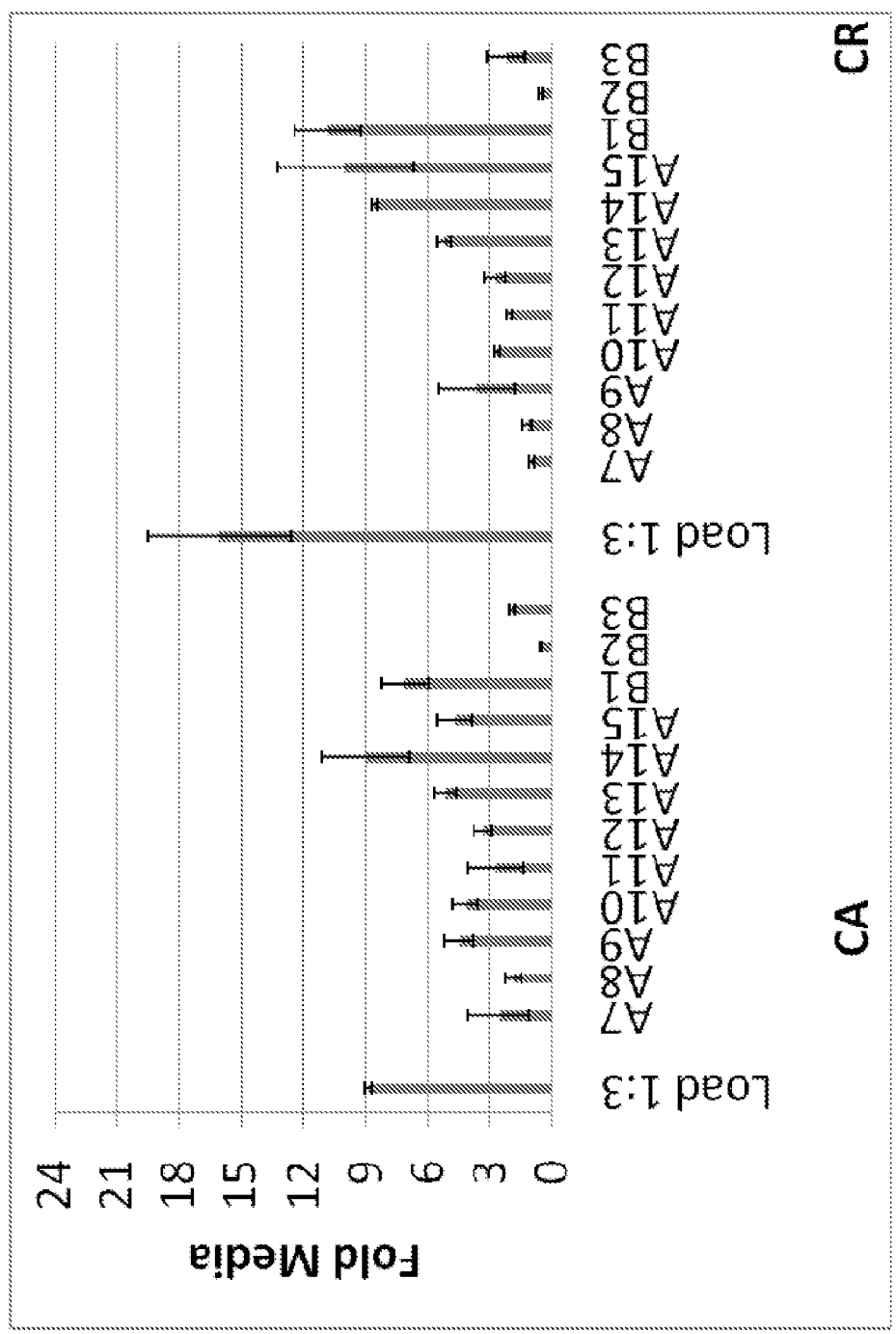
FIG. 2 is a bar graph showing fold induction (over media) of chemorepulsion (right) and chemoattraction (left) of neutrophils treated with S-200 chromatography fractions of cystic fluids.

FIG. 2: Evaluation of S-200 chromatography fractionation of cystic fluids on human neutrophils in transwell migration assay. Fractions were evaluated for chemoattraction (CA) and chemorepulsion of human neutrophils using a Boyden chamber transwell migration assay. Fractions A15 and B1 have the highest neutrophil repulsive activities as compared to other fractions.

Figure 3:
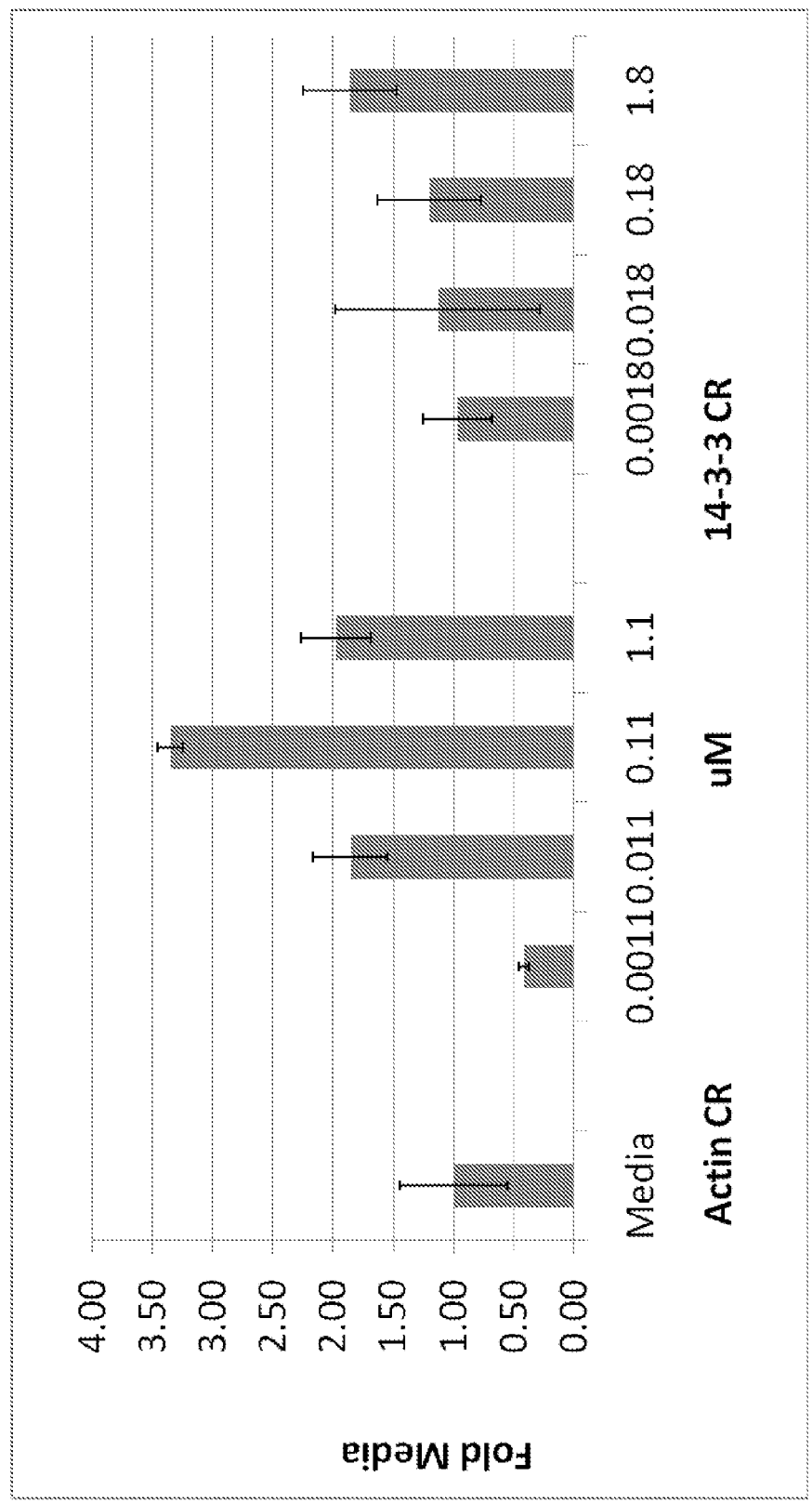
FIG. 3 is a bar graph showing fold induction (over media) of chemorepulsion of neutrophils treated with 0.0011, 0.011, 0.11 and 1.1 uM actin (left) and 0.0018, 0.018, 0.18 and 1.8 uM 14-3-3 (right).

FIG. 3: Effect of human actin and 14-3-3 on migration of human neutrophils. Actin and 14-3-3 were evaluated at different concentrations for their abilities to induce chemorepulsion (CR) of human neutrophils using a Boyden chamber transwell migration assay. Human neutrophils were effectively repelled by actin in transwell migration assays.

Figure 4:
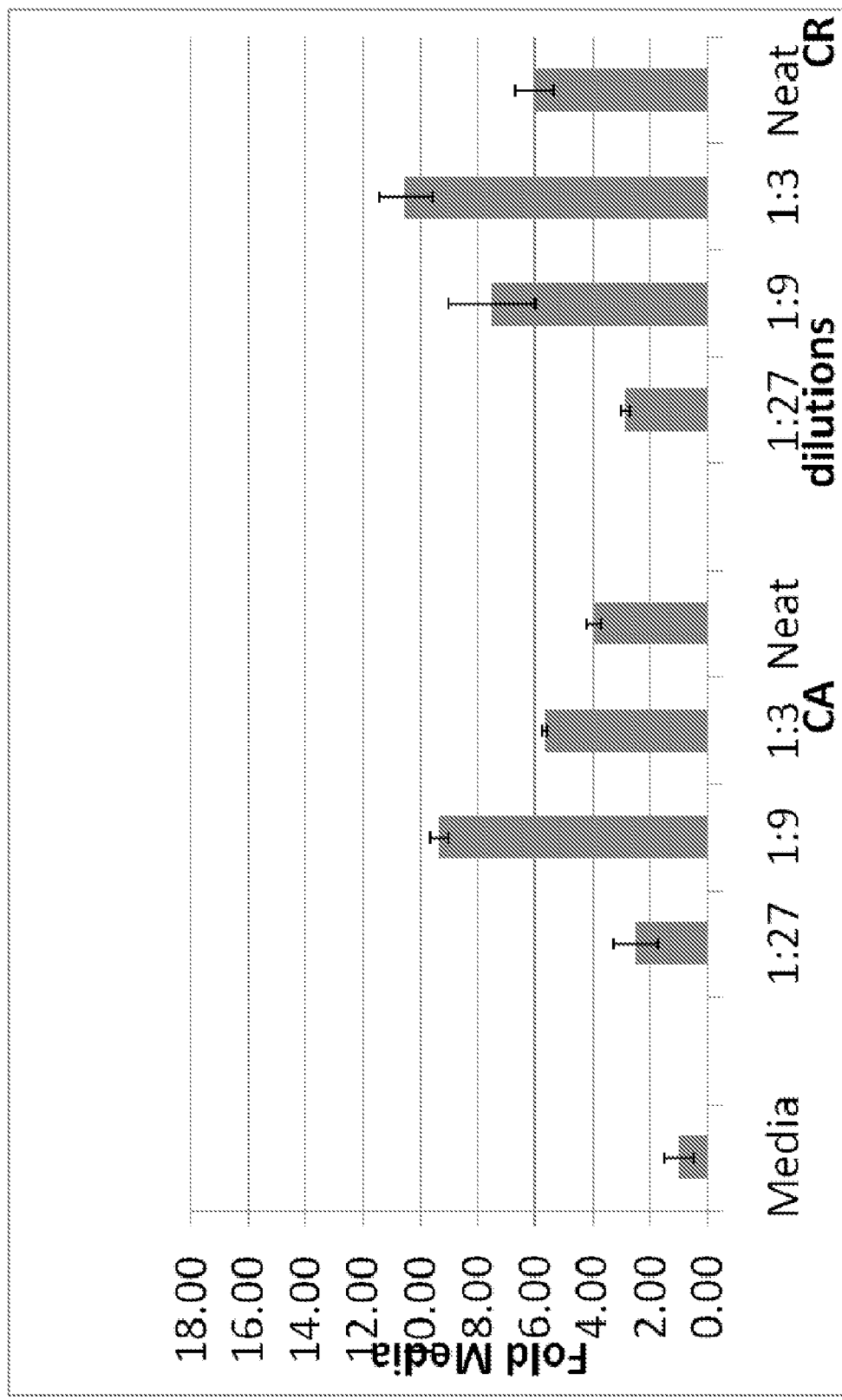
FIG. 4 is a bar graph showing fold induction (over media) of chemorepulsion (right) and chemoattraction (left) of neutrophils treated with a 1:1 combination of actin and 14-3-3 at 1:27, 1:9, 1:3 and neat dilutions.

FIG. 4: Effect of 1:1 combination of Actin and 14-3-3 on migration of human neutrophils. Actin and 14-3-3 were evaluated in 1:1 combination at different concentrations for their ability to induce chemoattraction (CA) and chemorepulsion (CR) of human neutrophils using a Boyden chamber transwell migration assay. Actin and 14-3-3 in combination effectively modulated human neutrophil migrations in transwell migration assays.

Figure 5:
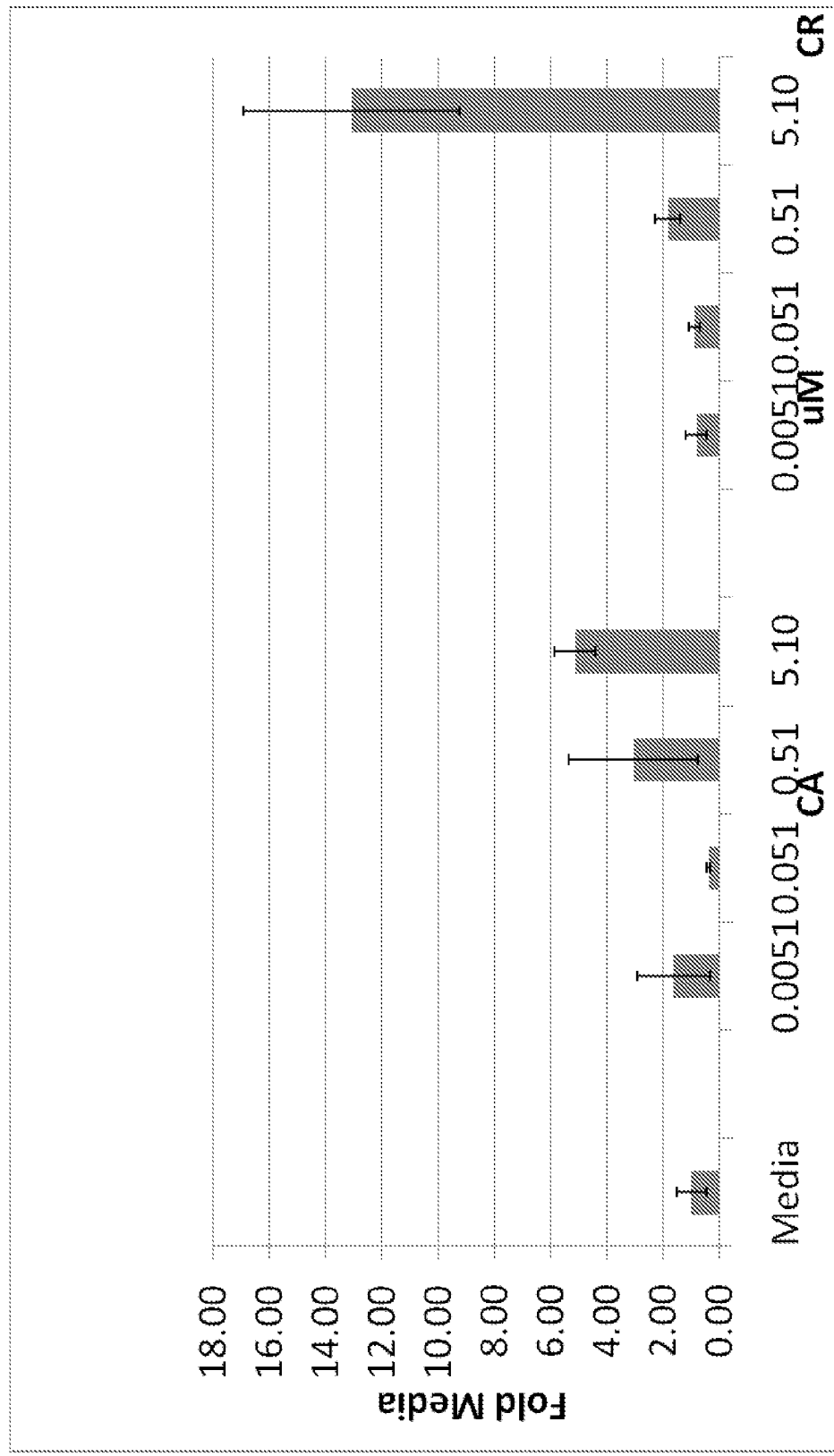
FIG. 5 is a bar graph showing fold induction (over media) of chemorepulsion (right) and chemoattraction (left) of neutrophils treated with 0.0051, 0.051, 0.51 and 5.1 uM apolipoprotein A1.

FIG. 5: Effect of apolipoprotein A1 on migration of human neutrophils. Apolipoprotein A1 was evaluated at different concentrations for its ability to induce chemoattraction (CA) and chemorepulsion (CR) of human neutrophils using a Boyden chamber transwell migration assay. Human neutrophils were effectively repelled by apolipoprotein A1 at 5.1 microM concentration.

Figure 6:
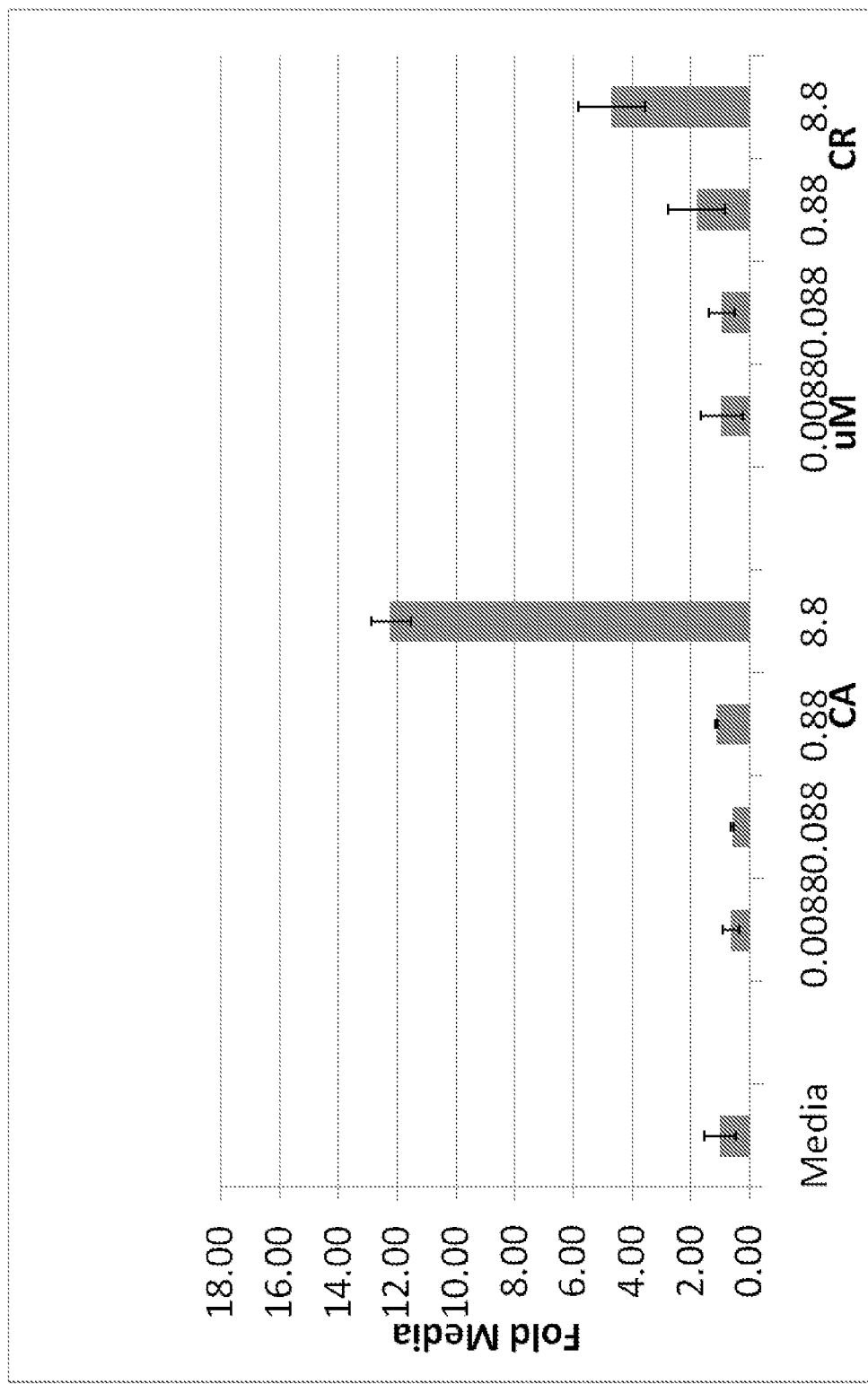
FIG. 6 is a bar graph showing fold induction (over media) of chemorepulsion (right) and chemoattraction (left) of neutrophils treated with 0.0088, 0.088, 0.88 and 8.8 uM hemopexin.
Figure 7:
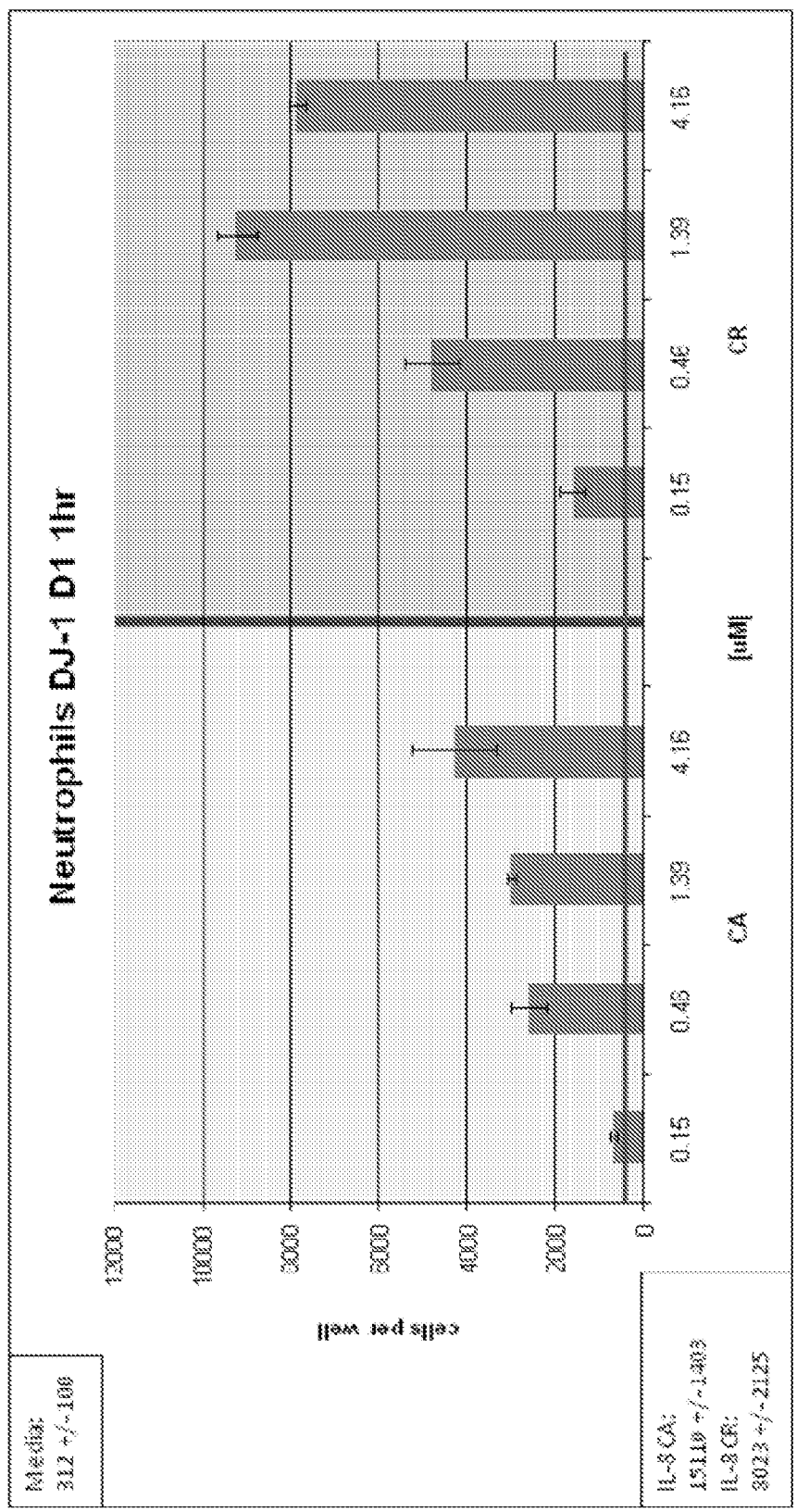
FIG. 7 is a bar graph showing induction (number of cells per well) of chemorepulsion (right) and chemoattraction (left) of neutrophils treated with 0.15, 0.46, 1.39 and 4.16 uM Park-7.
Figure 8:
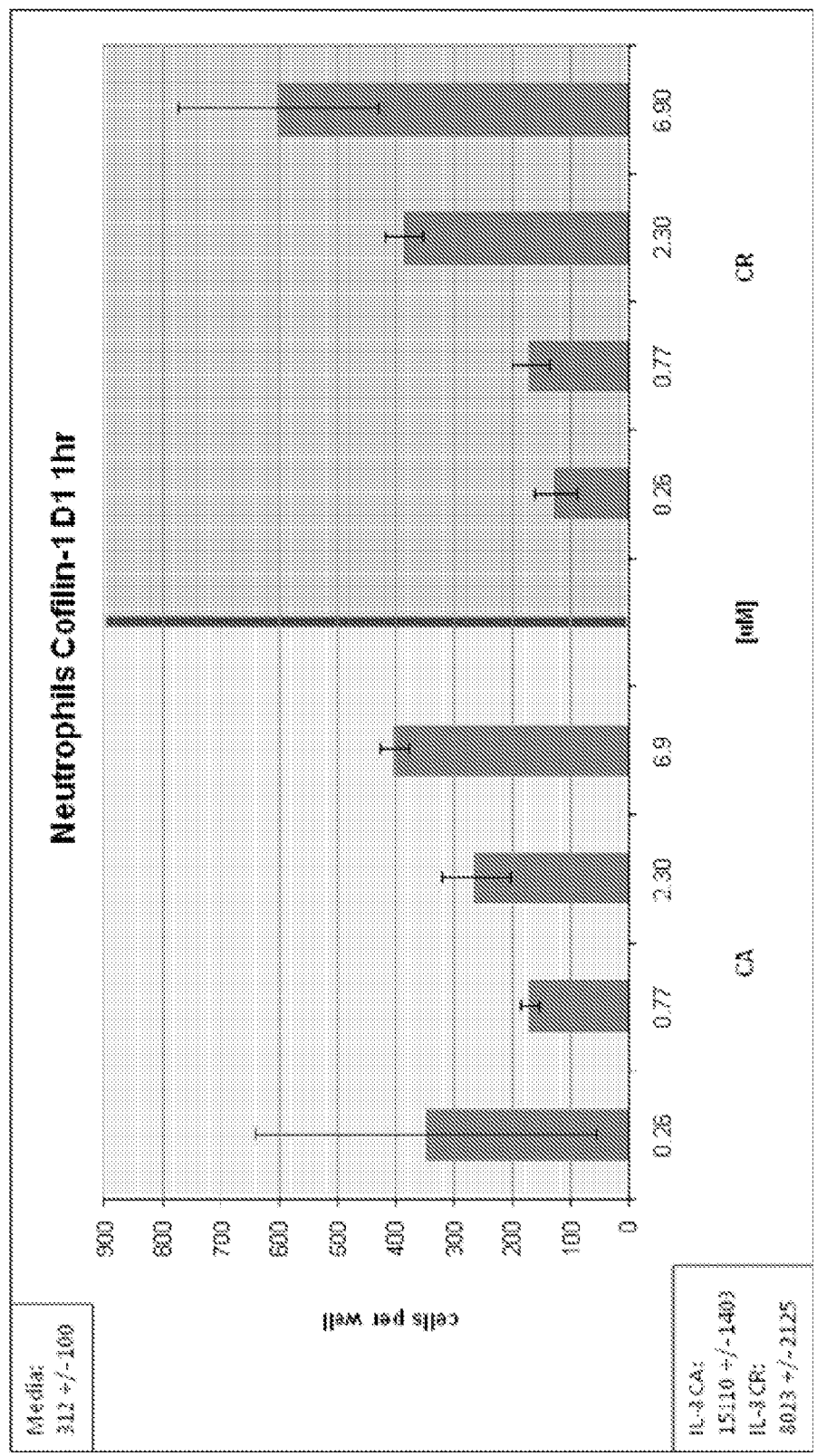
FIG. 8 is a bar graph showing induction (number of cells per well) of chemorepulsion (right) and chemoattraction (left) of neutrophils treated with 0.28, 0.77, 2.30 and 6.9 uM cofilin-1.
Figure 9:
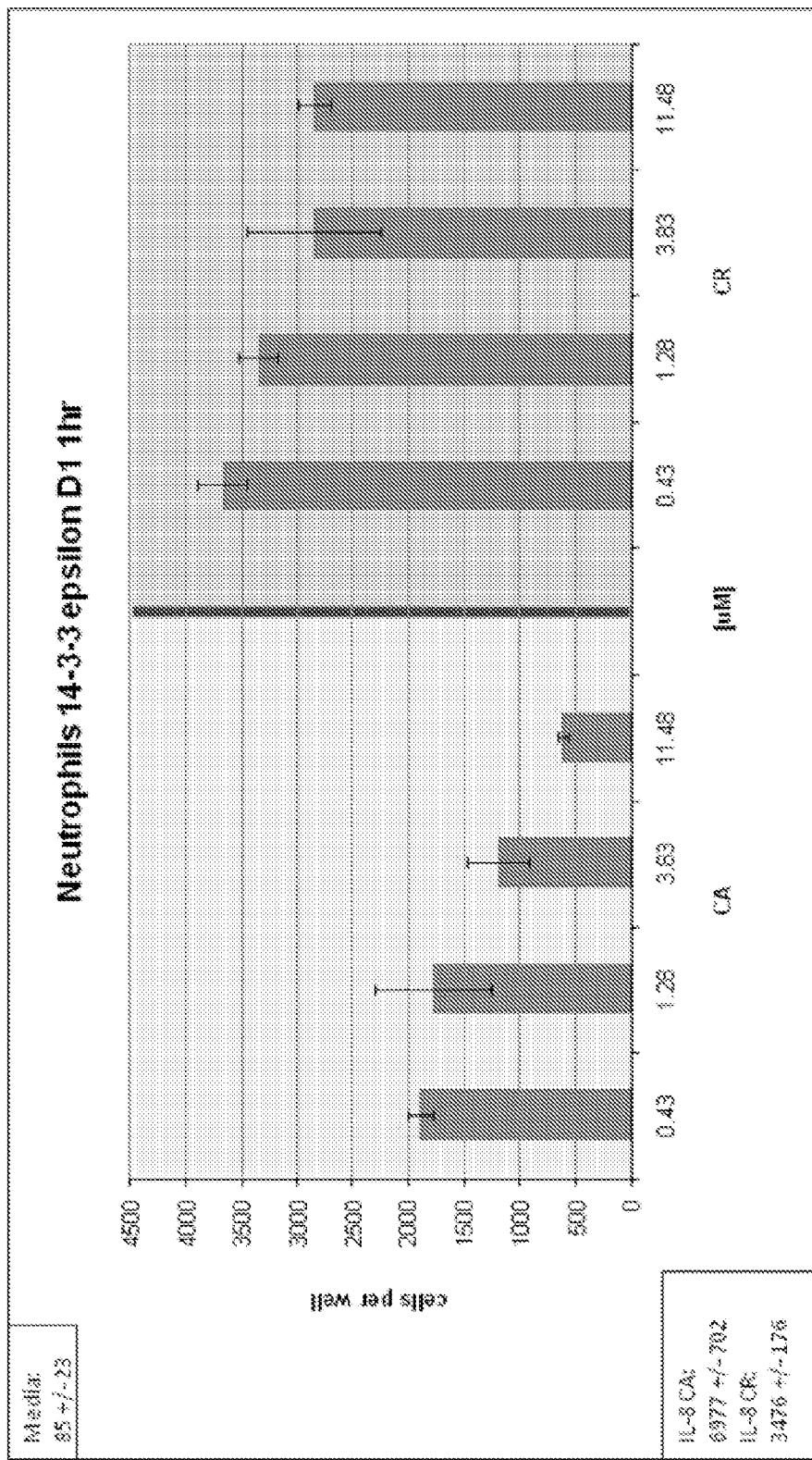
FIG. 9 is a bar graph showing induction (number of cells per well) of chemorepulsion (right) and chemoattraction (left) of neutrophils treated with 0.43, 1.28, 3.83 and 11.48 uM 14-3-3 epsilon.
Figure 10:
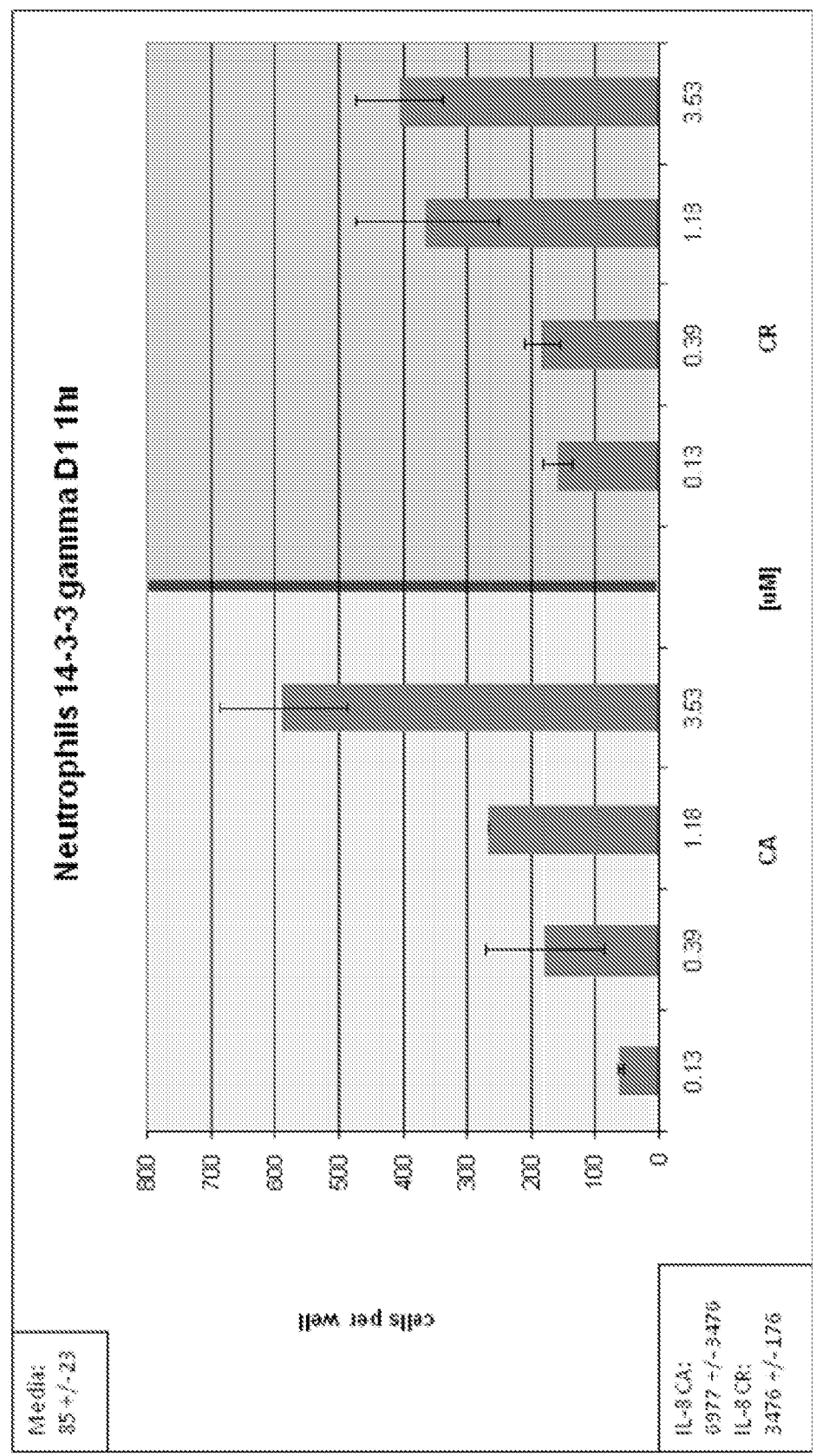
FIG. 10 is a bar graph showing induction (number of cells per well) of chemorepulsion (right) and chemoattraction (left) of neutrophils treated with 0.13, 0.39, 1.18, 3.53 uM 14-3-3 gamma.
Figure 11:
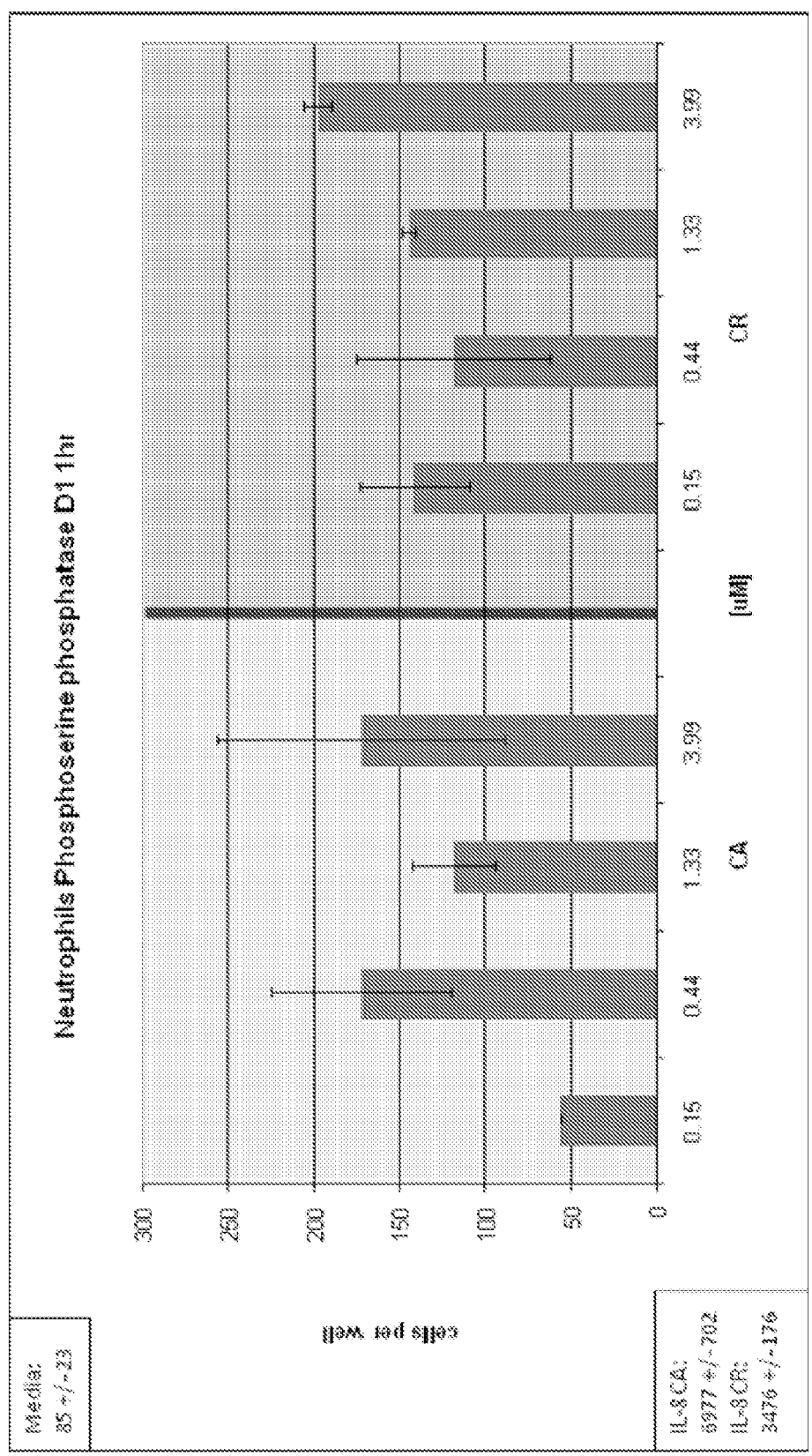
FIG. 11 is a bar graph showing induction (number of cells per well) of chemorepulsion (right) and chemoattraction (left) of neutrophils treated with 0.15, 0.44, 1.33 and 3.99 uM phosphoserine phosphatase.
Figure 12:
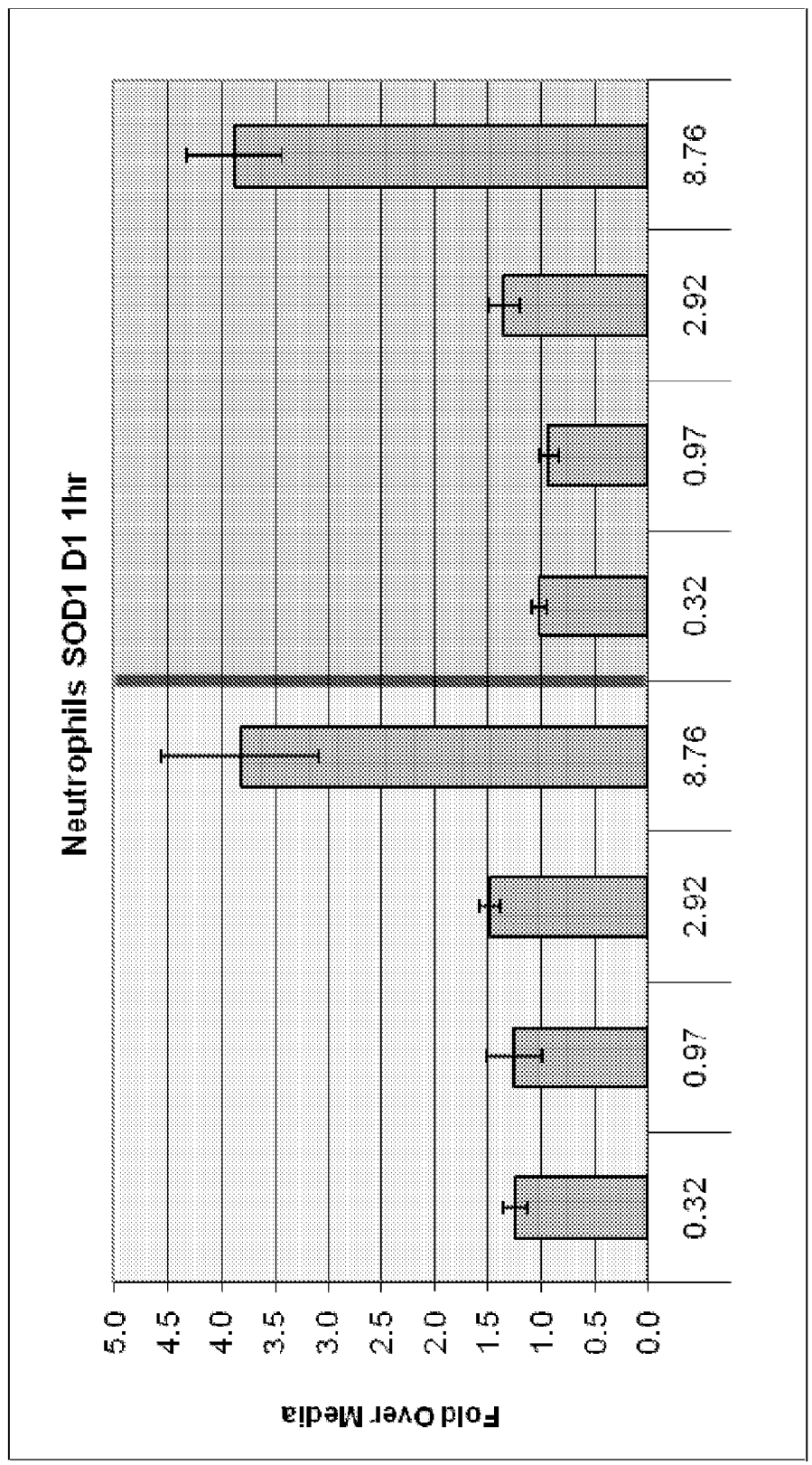
FIG. 12 is a bar graph showing fold induction (over media) of chemorepulsion (right) and chemoattraction (left) of neutrophils treated with 0.32, 0.97, 2.92 and 8.76 uM superoxide dismutase.
Figure 13:
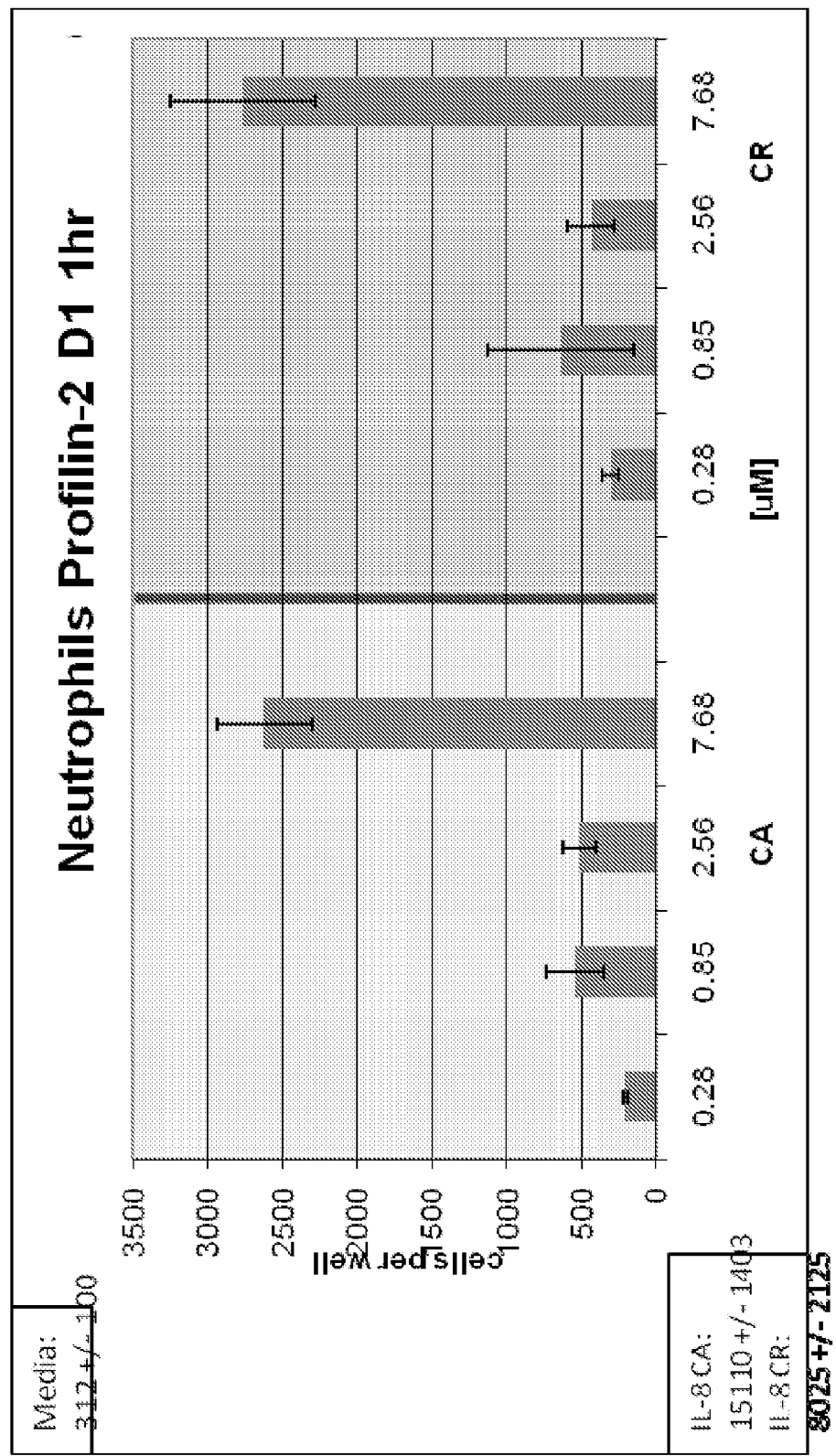
FIG. 13 is a bar graph showing induction (number of cells per well) of chemorepulsion (right) and chemoattraction (left) of neutrophils treated with 0.28, 0.85, 2.56 and 7.68 uM profilin-2.
Figure 14:
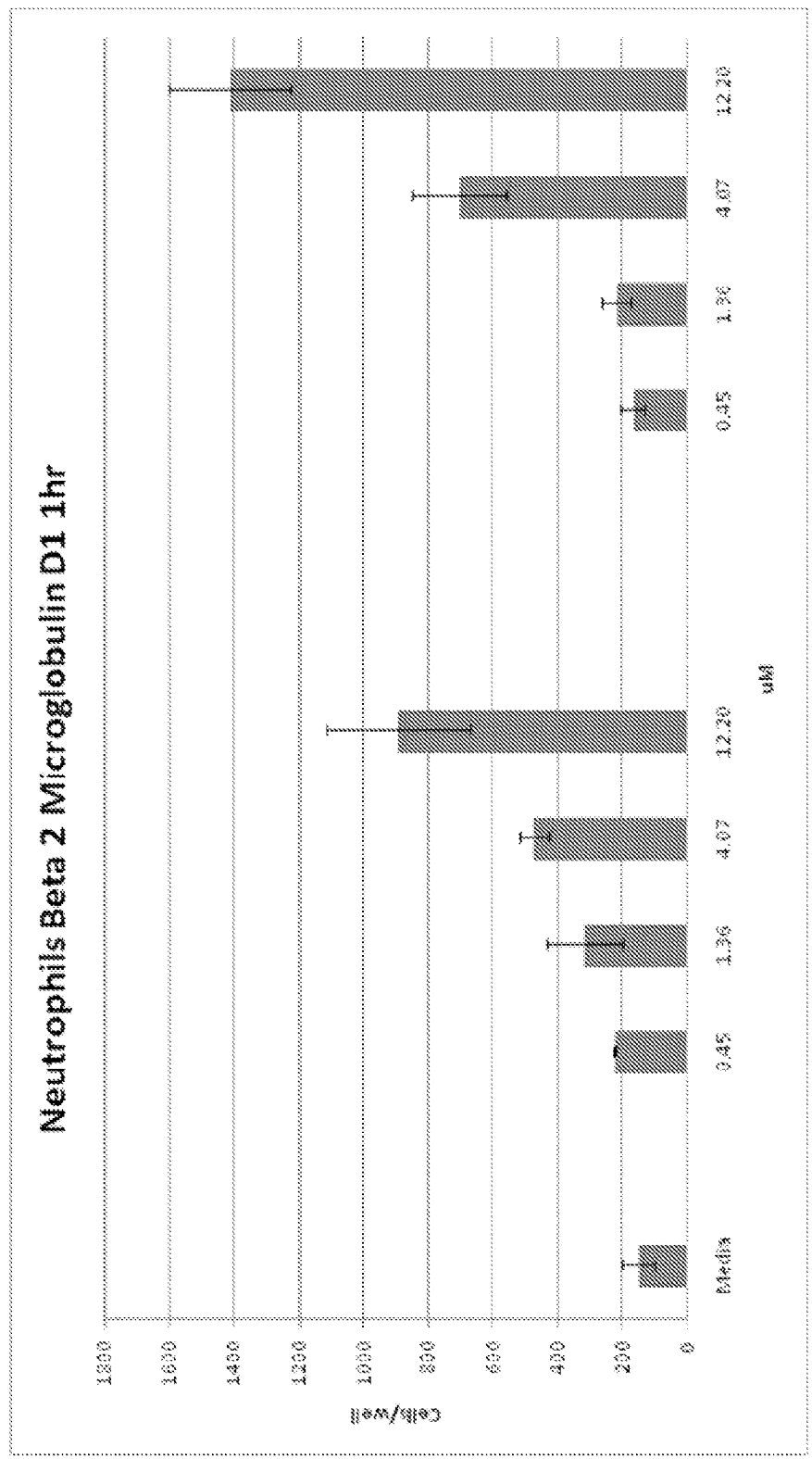
FIG. 14 is a bar graph showing induction (number of cells per well) of chemorepulsion (right) and chemoattraction (left) of neutrophils treated with 0.45, 1.36, 4.07 and 12.20 uM beta-2 microglobulin.
Figure 15:
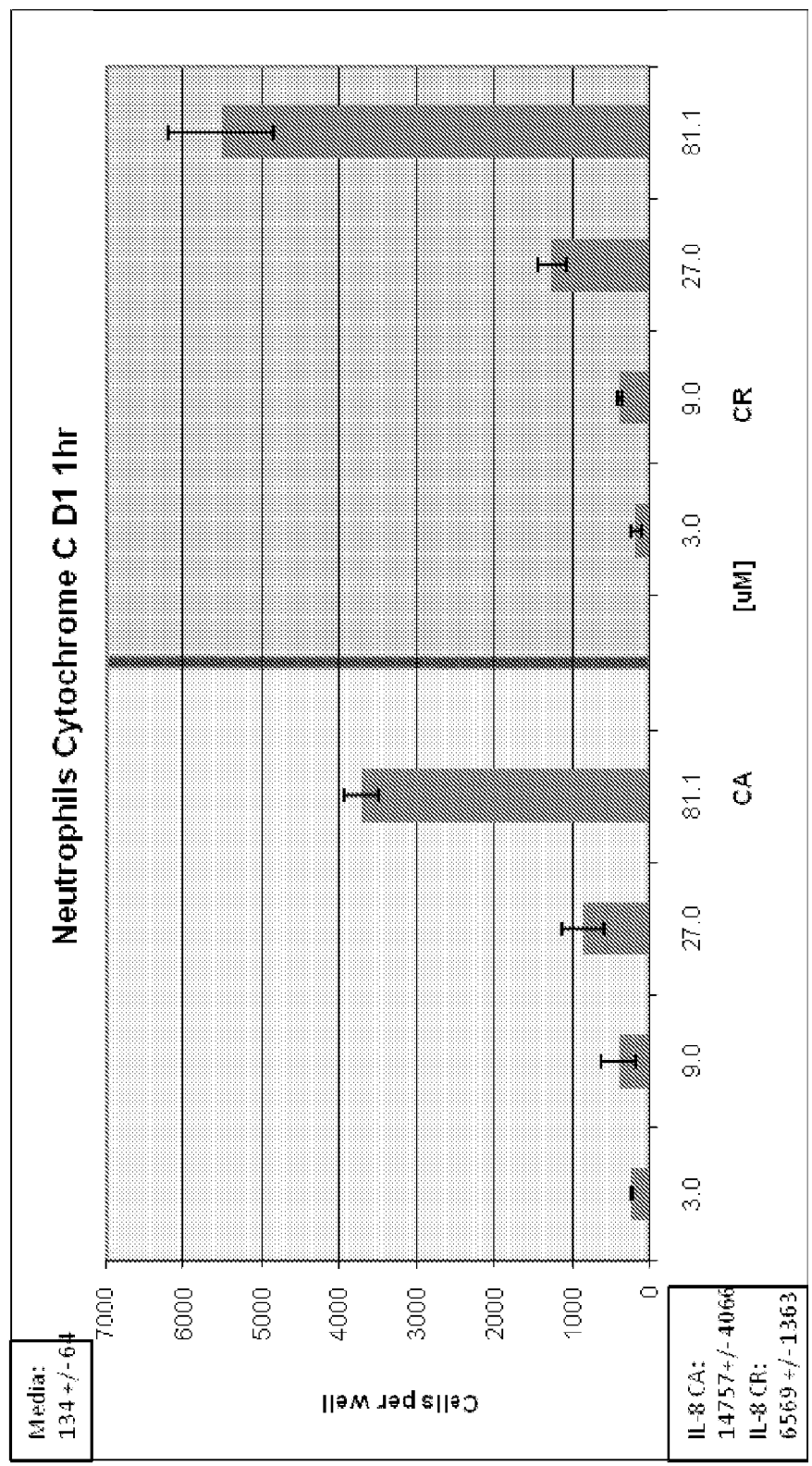
FIG. 15 is a bar graph showing induction (number of cells per well) of chemorepulsion (right) and chemoattraction (left) of neutrophils treated with 3, 9, 27 and 81.1 uM cytochrome C.
Figure 16:
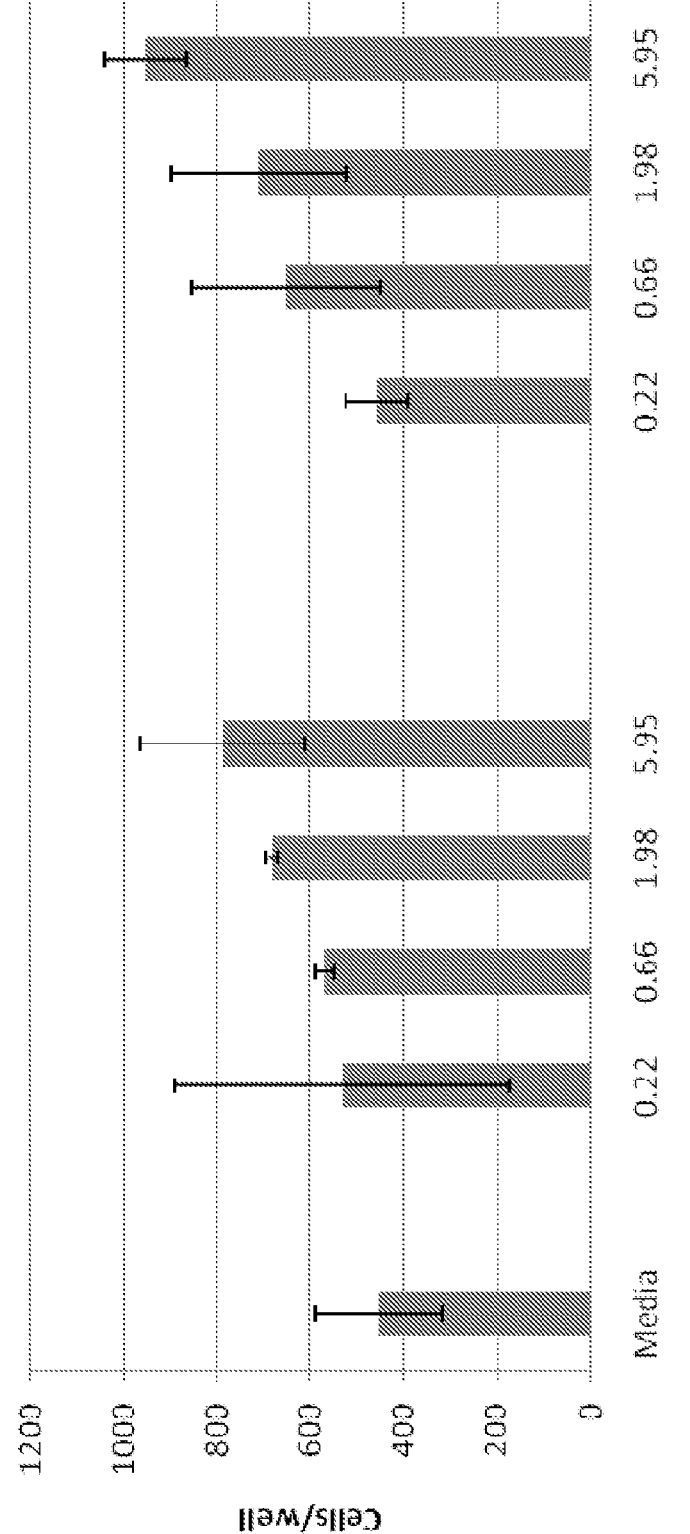
FIG. 16 is a bar graph showing induction (number of cells per well) of chemorepulsion (right) and chemoattraction (left) of neutrophils treated with 0.22, 0.66, 1.98 and 5.95 uM cystatin B.
Figure 17:
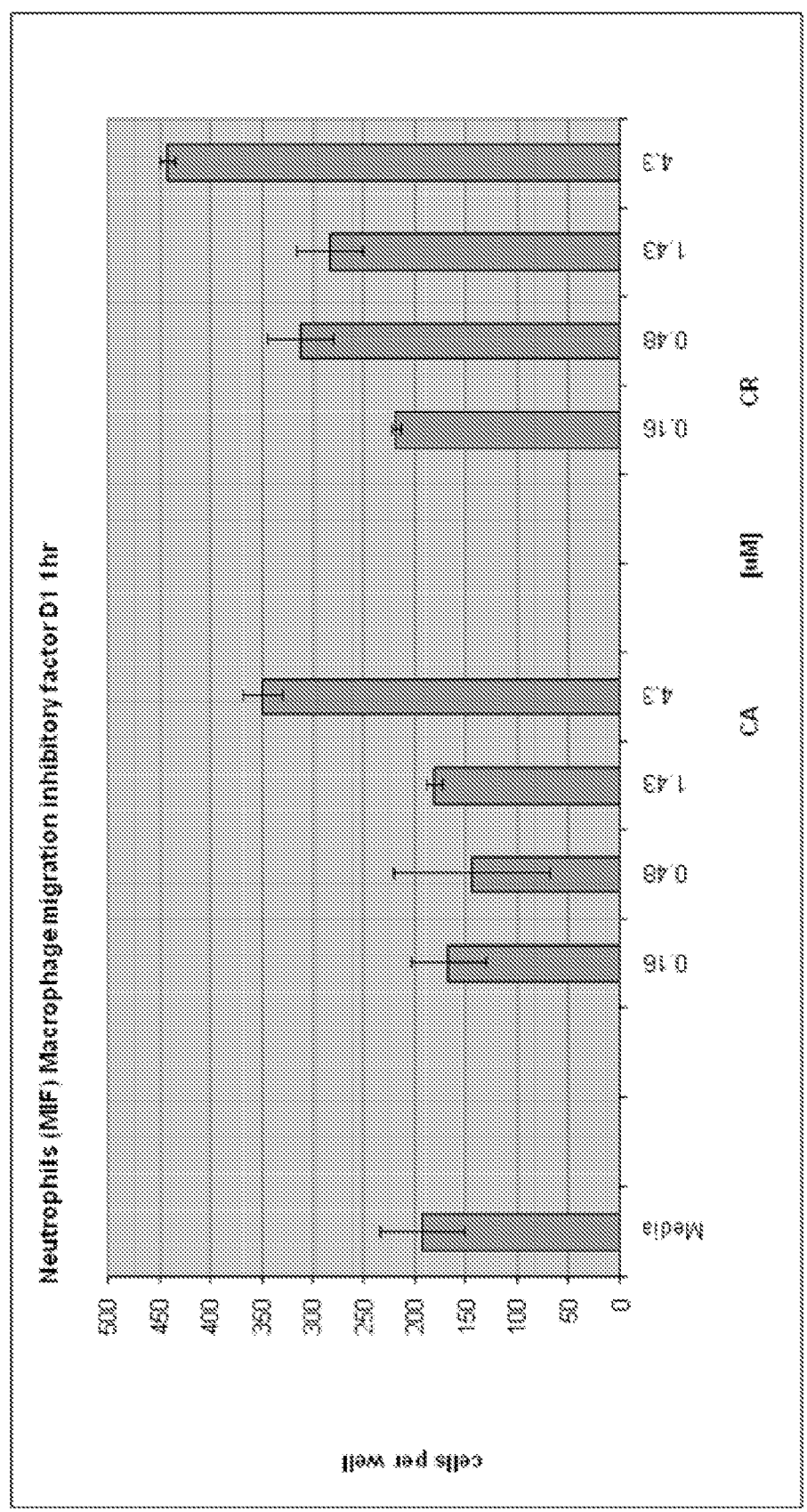
FIG. 17 is a bar graph showing induction (number of cells per well) of chemorepulsion (right) and chemoattraction (left) of neutrophils treated with 0.16, 0.48, 1.43 and 4.3 uM macrophage inhibitor factor (MIF).
Figure 18:
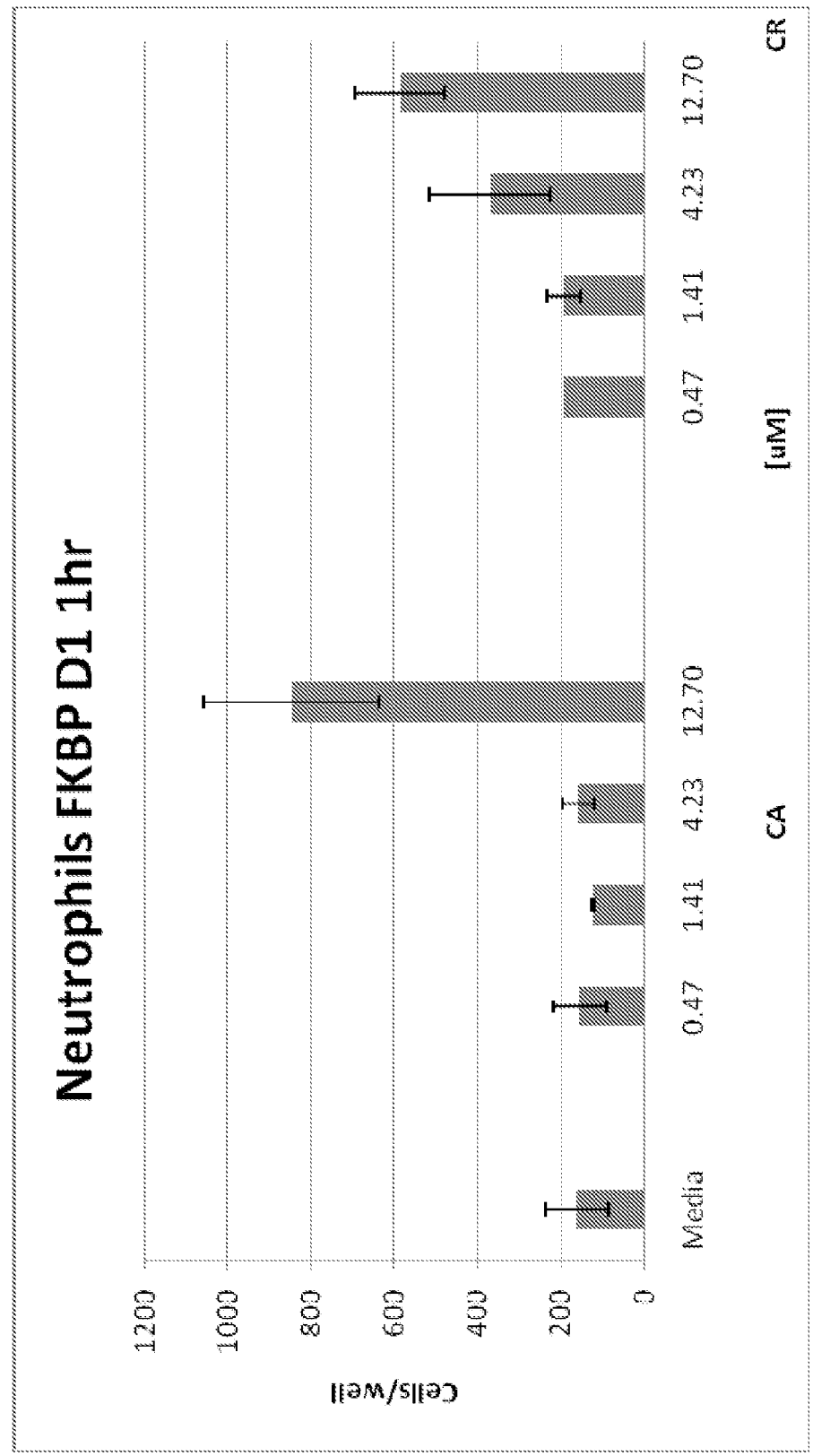
FIG. 18 is a bar graph showing induction (number of cells per well) of chemorepulsion (right) and chemoattraction (left) of neutrophils treated with 0.47, 1.41, 4.23 and 12.70 uM FKBP.
Figure 19:
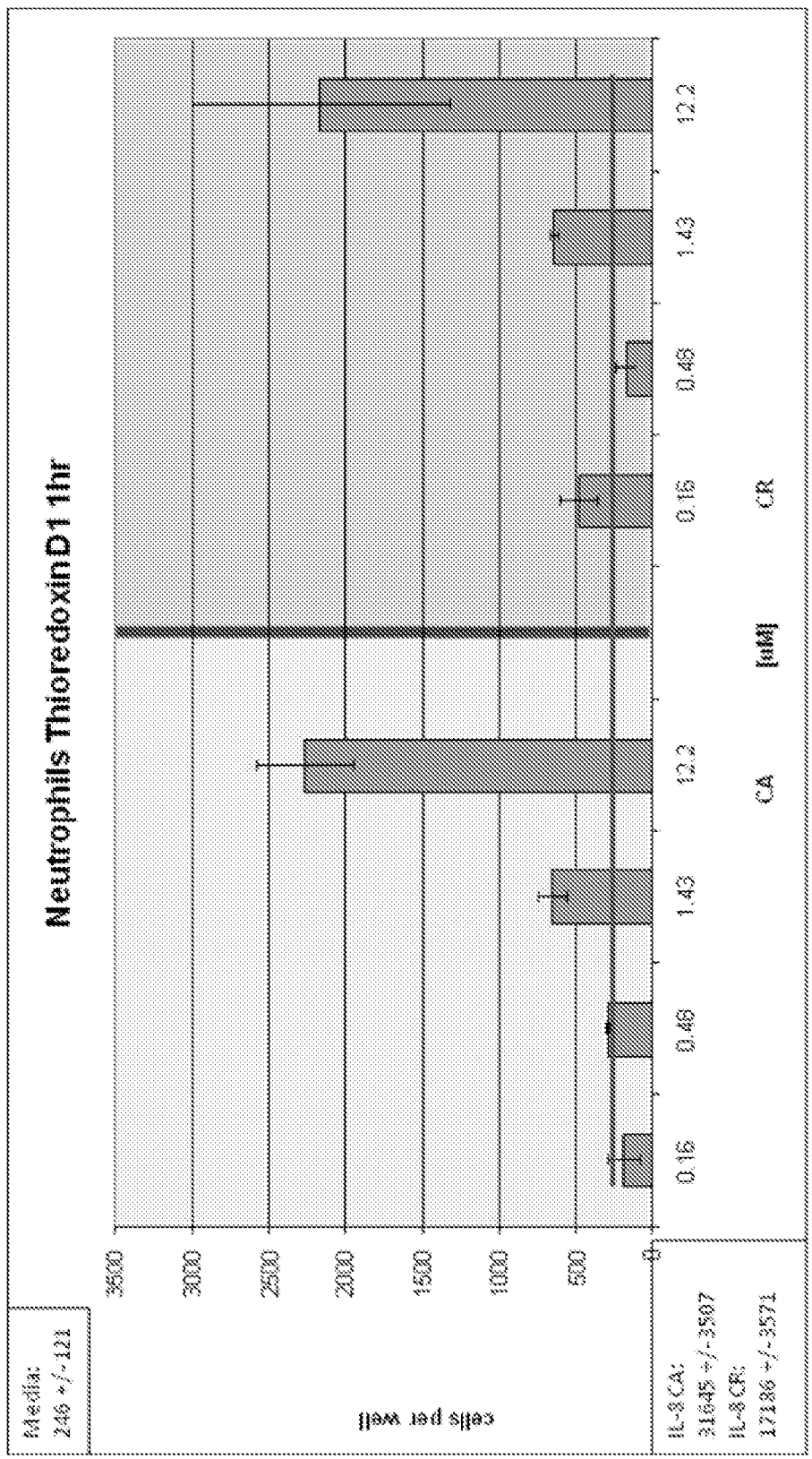
FIG. 19 is a bar graph showing induction (number of cells per well) of chemorepulsion (right) and chemoattraction (left) of neutrophils treated with 0.16, 0.48, 1.43 and 12.2 uM thioredoxin.
Figure 20:
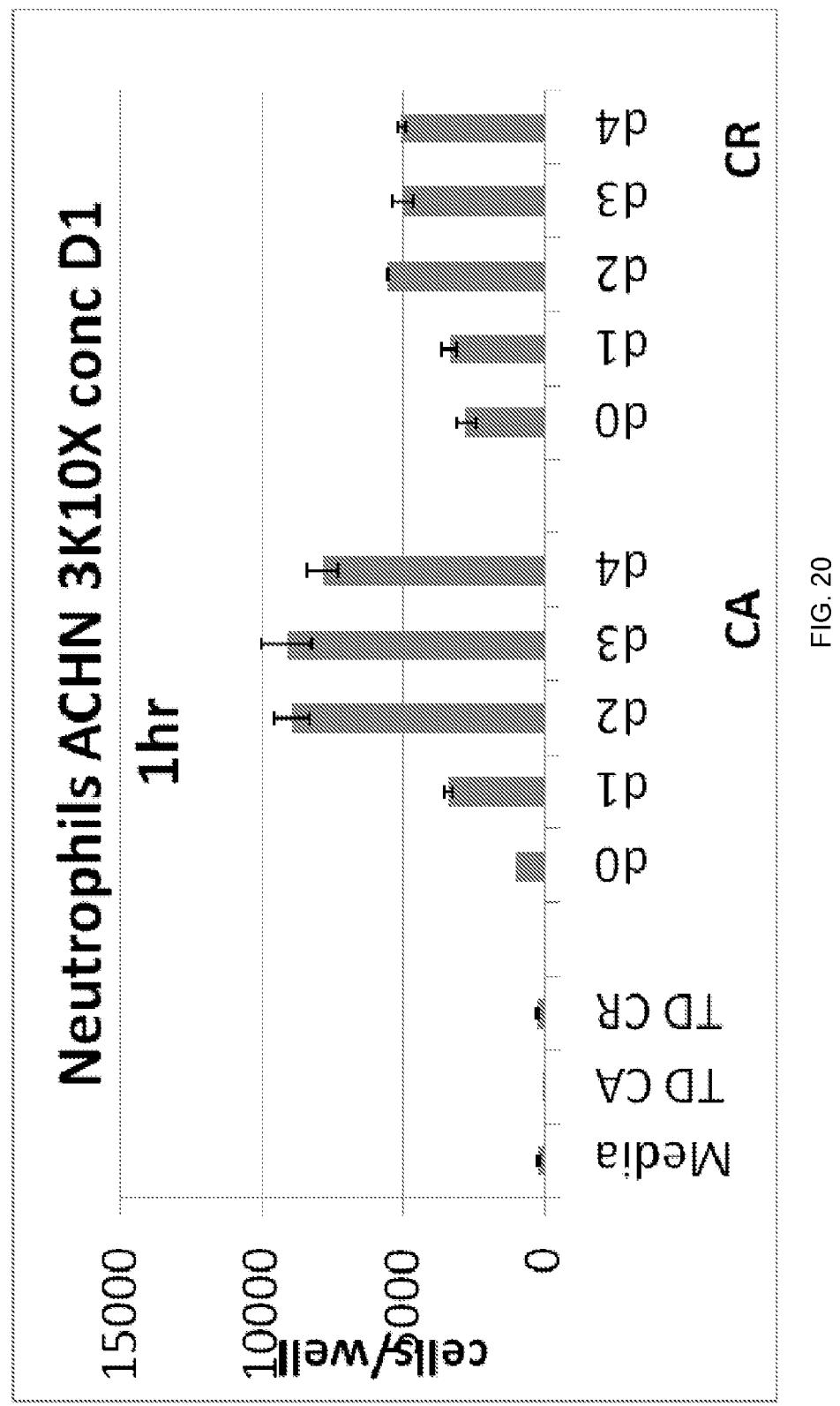
FIG. 20 is a bar graph showing induction (number of cells per well) of chemorepulsion (right) and chemoattraction (left) of neutrophils treated with ACHN supernatant fractions collected from day 0 (d0) to day 4 (d4) and Turbodoma (used as controls).
Figure 21:
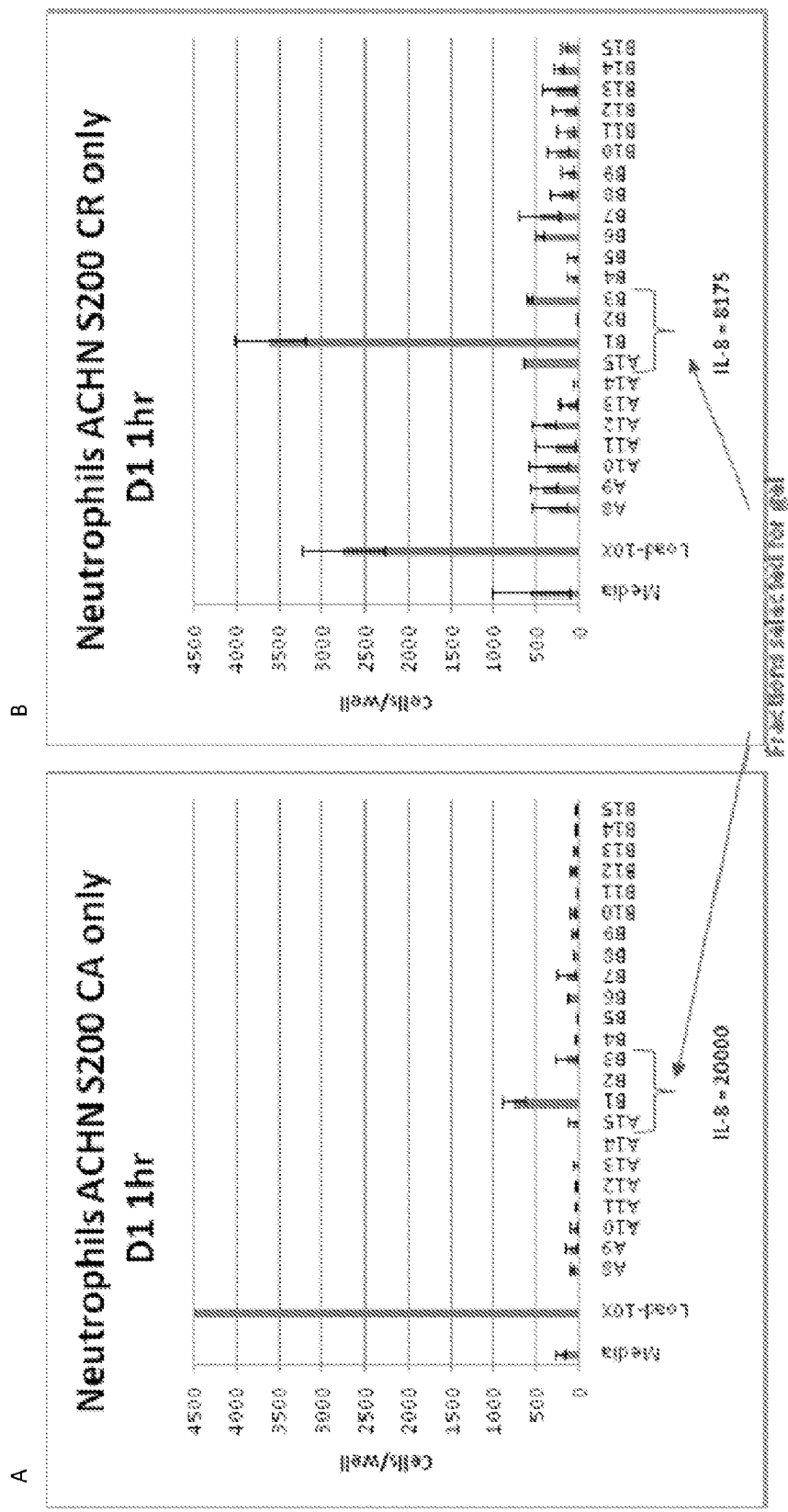
FIGS. 21A and B are bar graphs showing induction (number of cells per well) of chemorepulsion (B) and chemoattraction (A) of neutrophils treated with ACHN size exclusion fractions.
Figure 22:
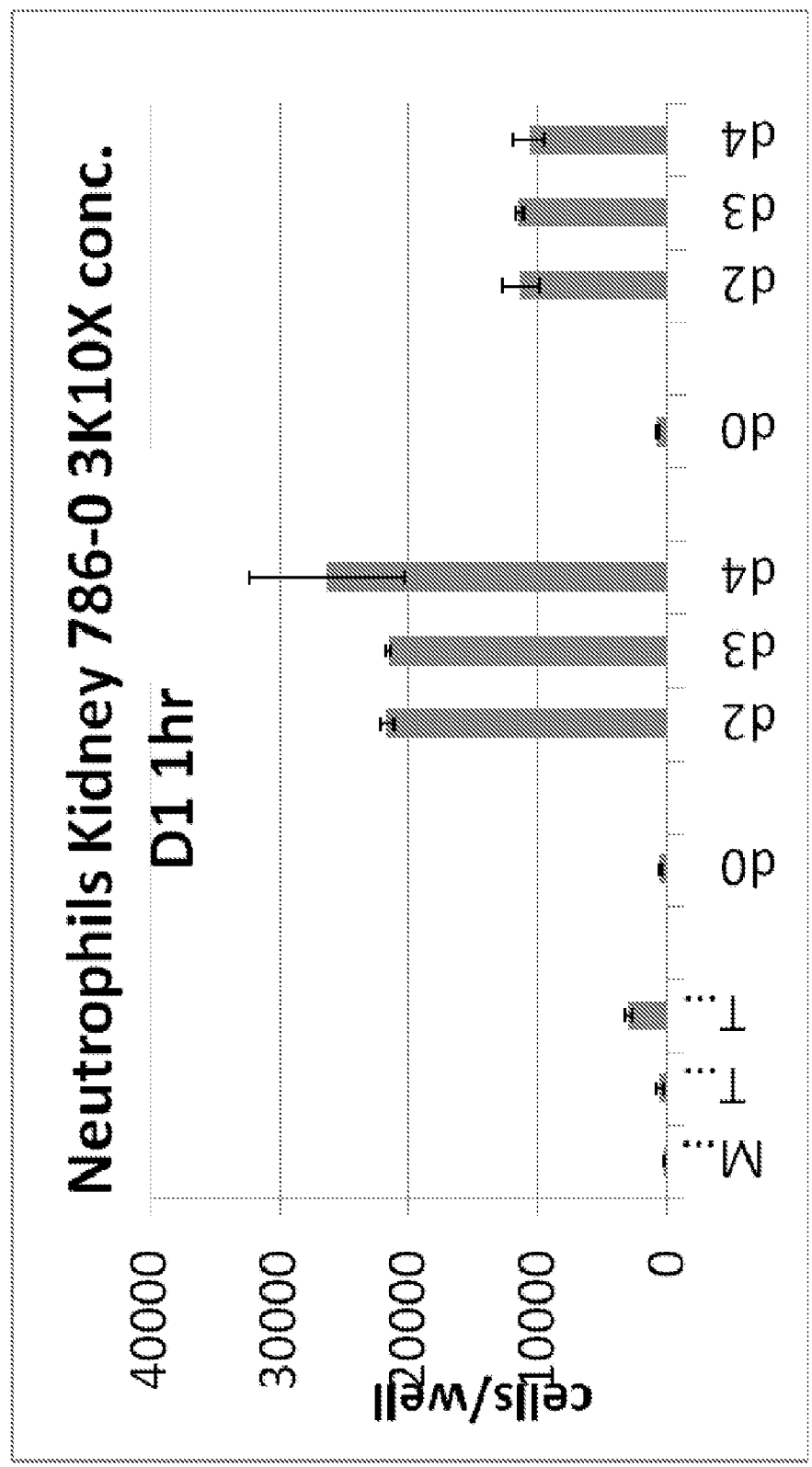
FIG. 22 is a bar graph showing induction (number of cells per well) of chemorepulsion (right) and chemoattraction (left) of neutrophils treated with 786-O supernatant fractions collected from day 0 (d0) to day 4 (d4) and Turbodoma control (TD).
Figure 23:
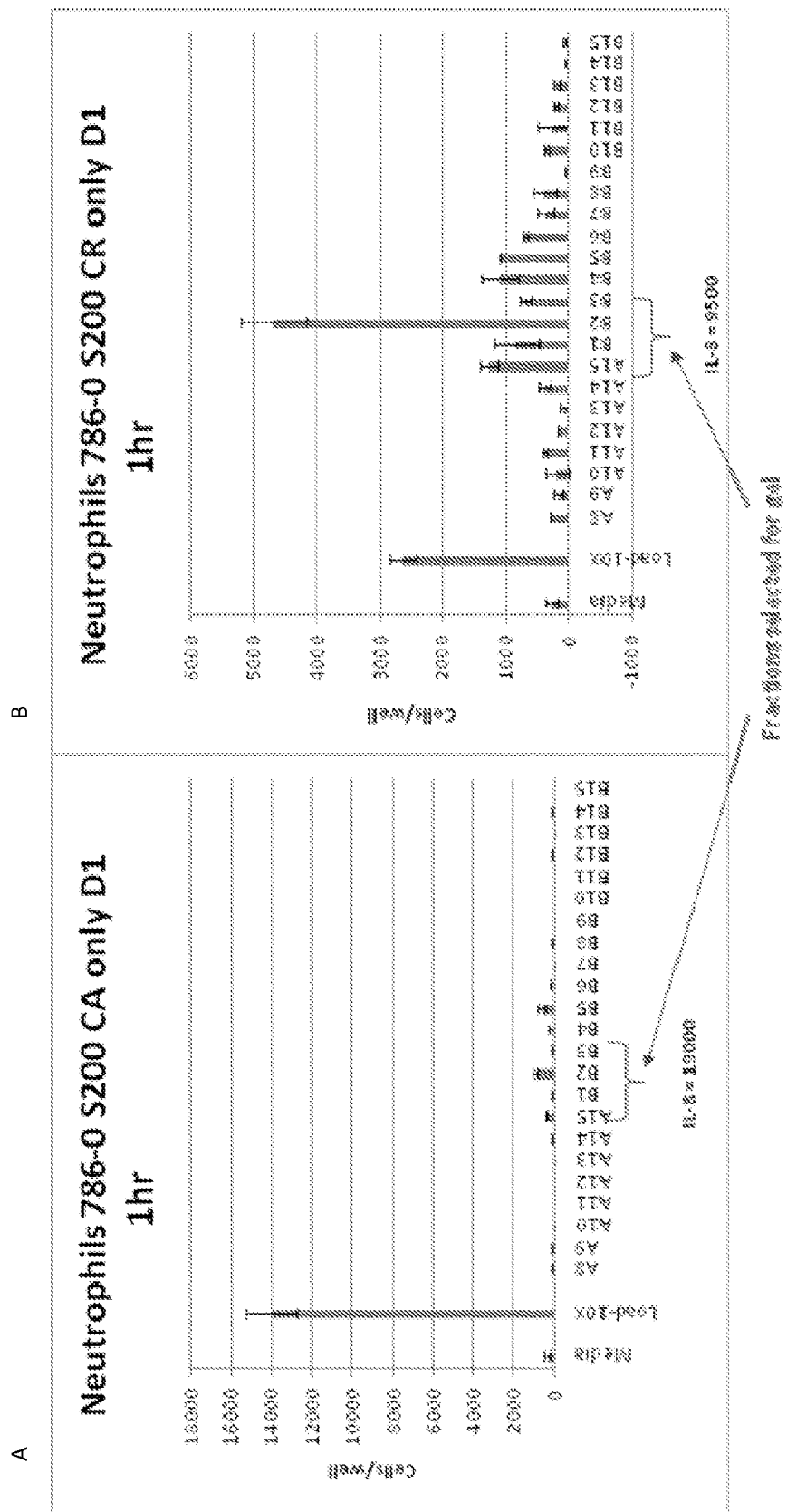
FIGS. 23A and B are bar graphs showing induction (number of cells per well) of chemorepulsion (B) and chemoattraction (A) of neutrophils treated with 786-O size exclusion fractions.
Figure 24:
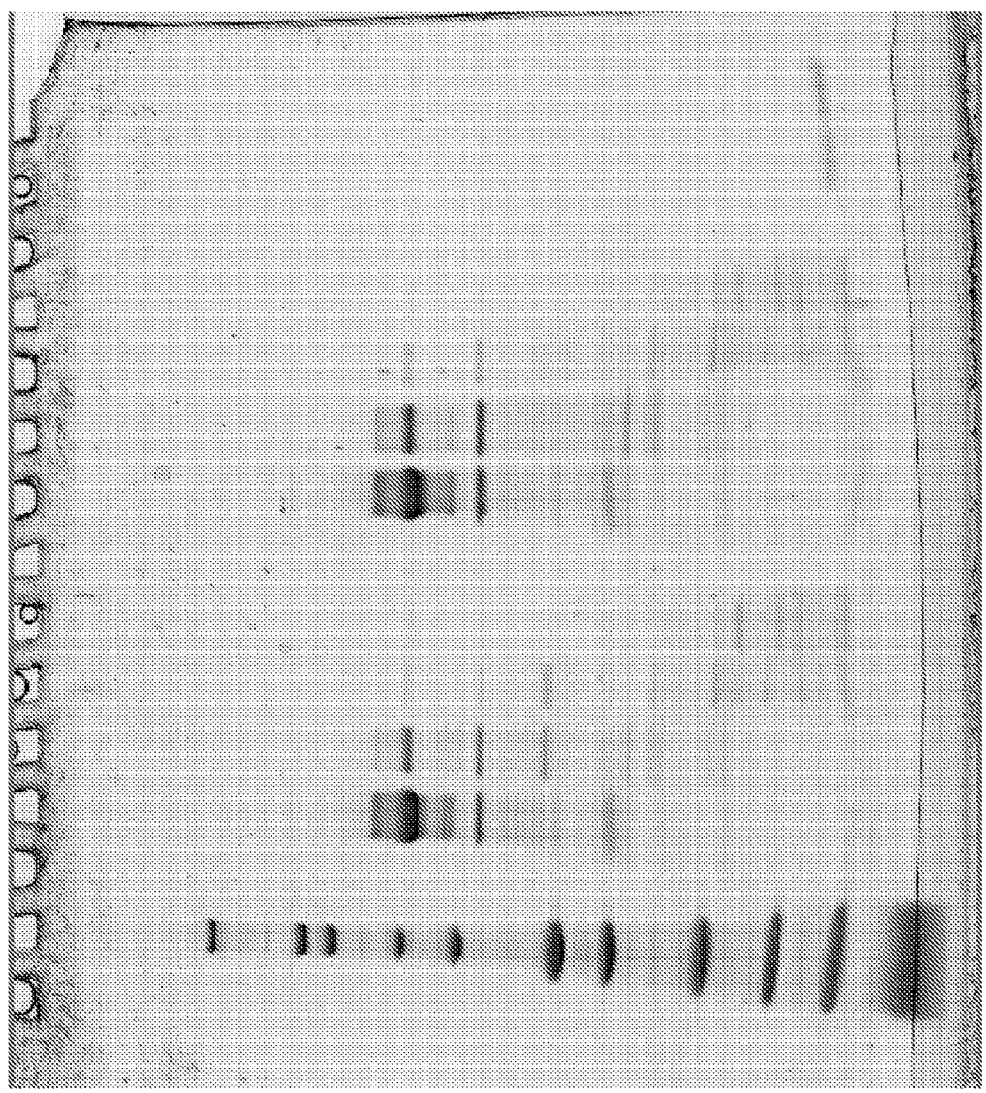
FIG. 24 is a photograph of the SDS PAGE gel of supernatant fractions from ACHN and 786-O.
Figure 25:
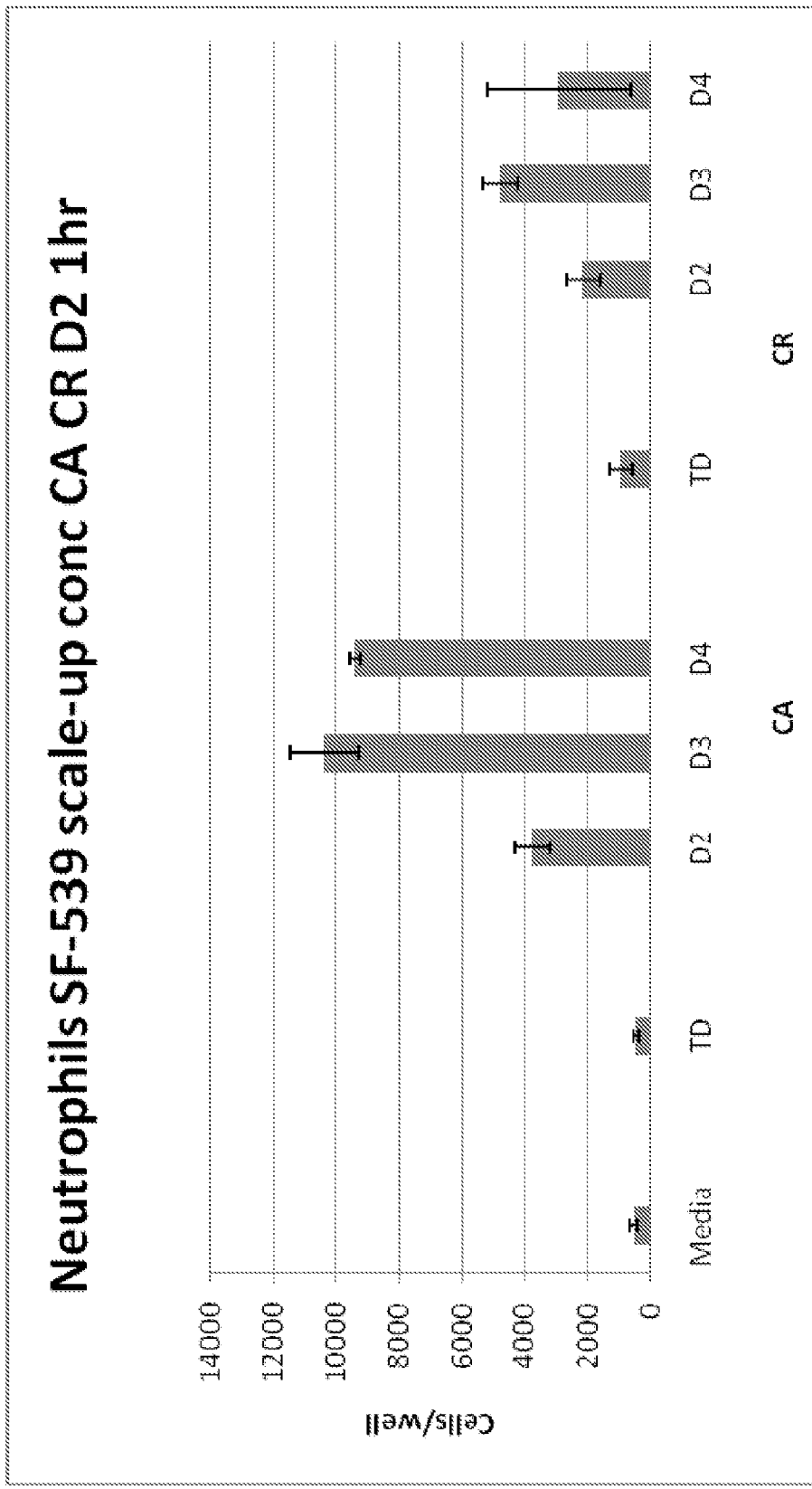
FIG. 25 is a bar graph showing induction (number of cells per well) of chemorepulsion (right) and chemoattraction (left) of neutrophils treated with SF-359 supernatant fractions collected from day 2 (d2) to day 4 (d4) and TD control.
Figure 26:
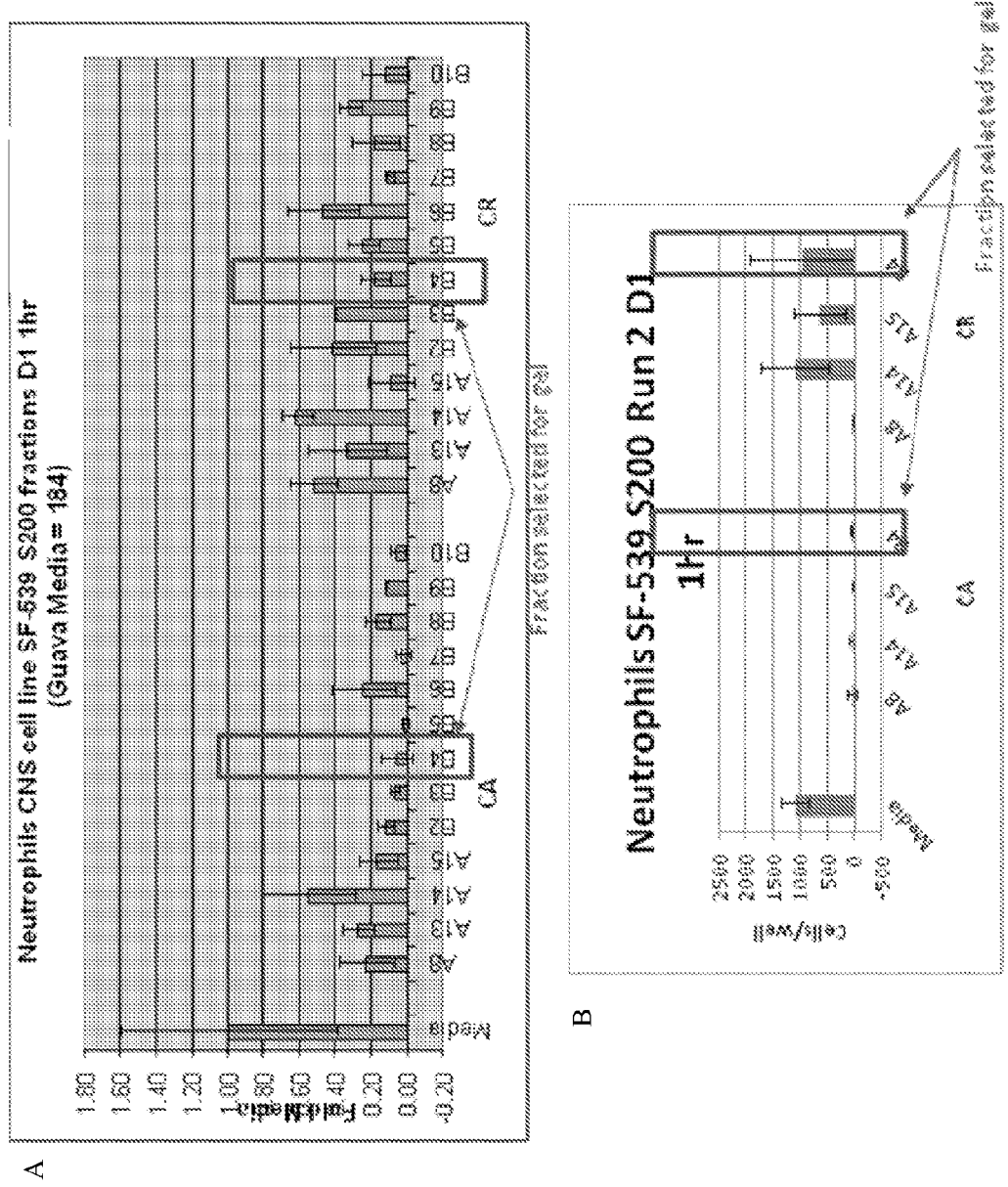
FIGS. 26A and B are bar graphs showing fold induction (over media) (A) or number of cells (B) of chemorepulsion (right) and chemoattraction (left) of neutrophils treated with SF-359 size exclusion fractions.
Figure 27:
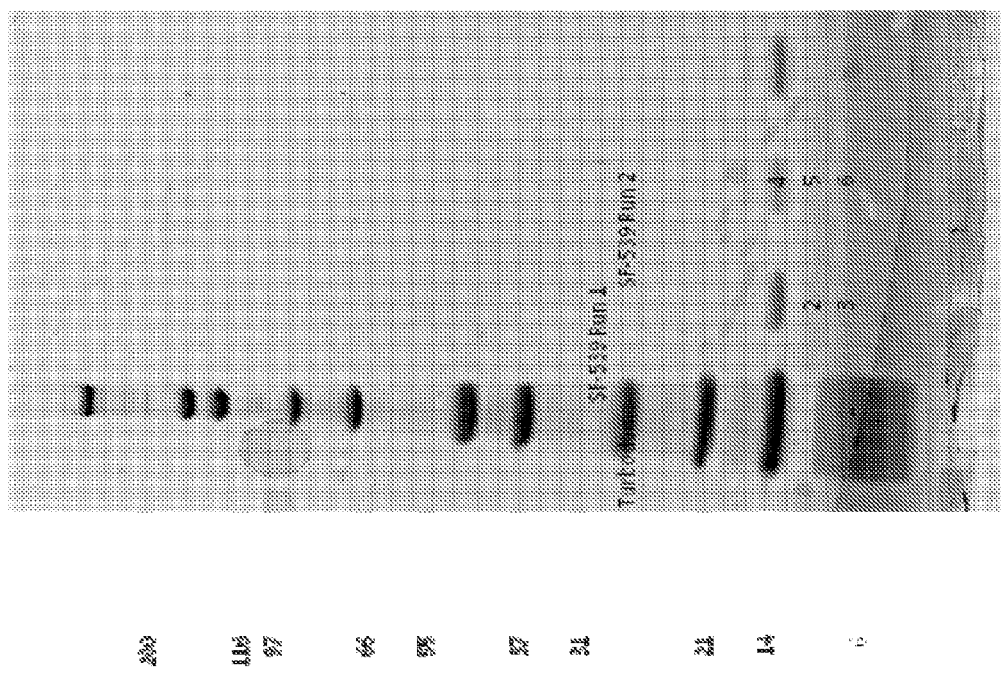
FIG. 27 is a photograph of the SDS PAGE gel of supernatant fractions from SF-359 culture.
Figure 28:
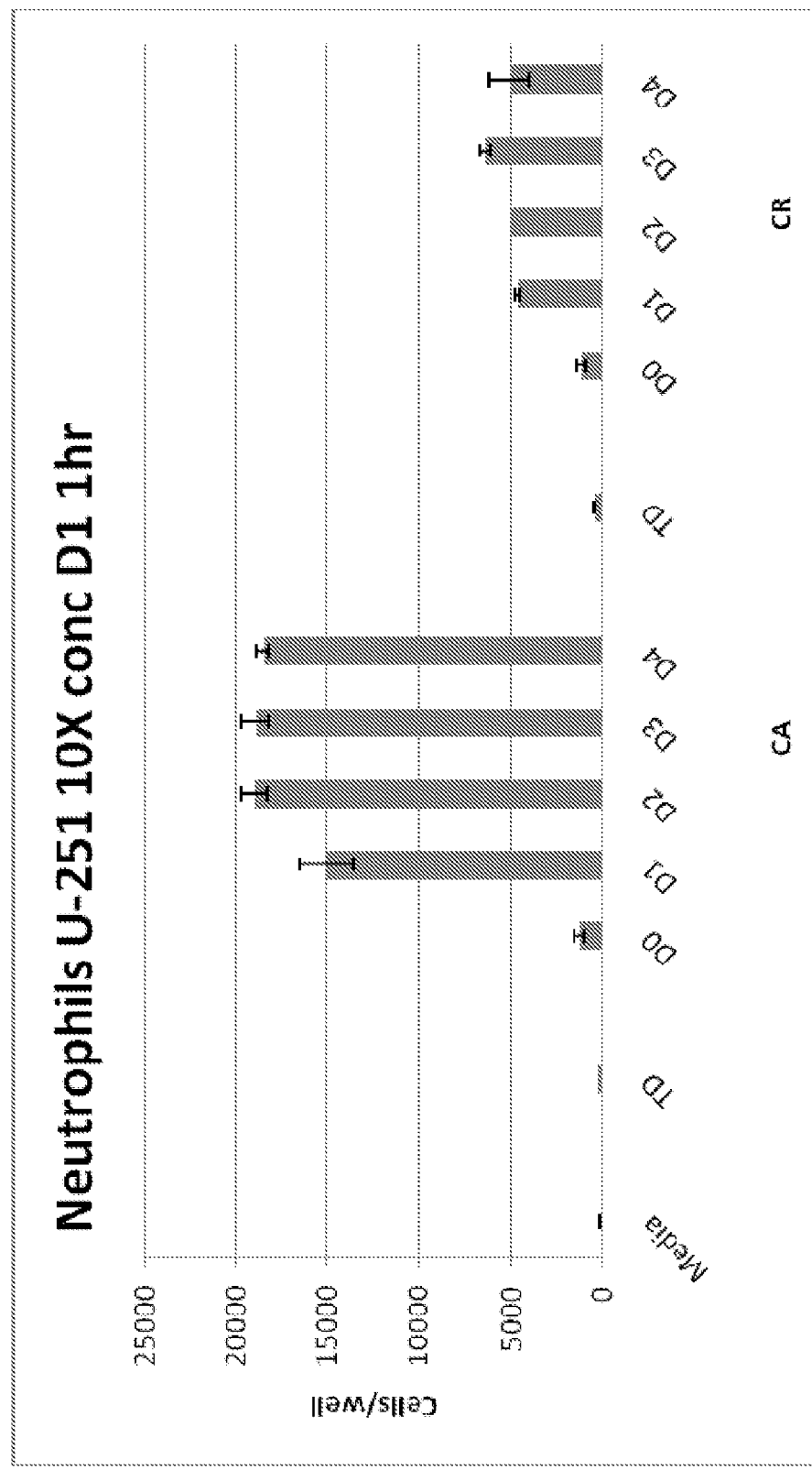
FIG. 28 is a bar graph showing induction (number of cells per well) of chemorepulsion (right) and chemoattraction (left) of neutrophils treated with U-251 supernatant fractions collected from day 0 (d0) to day 4 (d4) and TD control.
Figure 29:
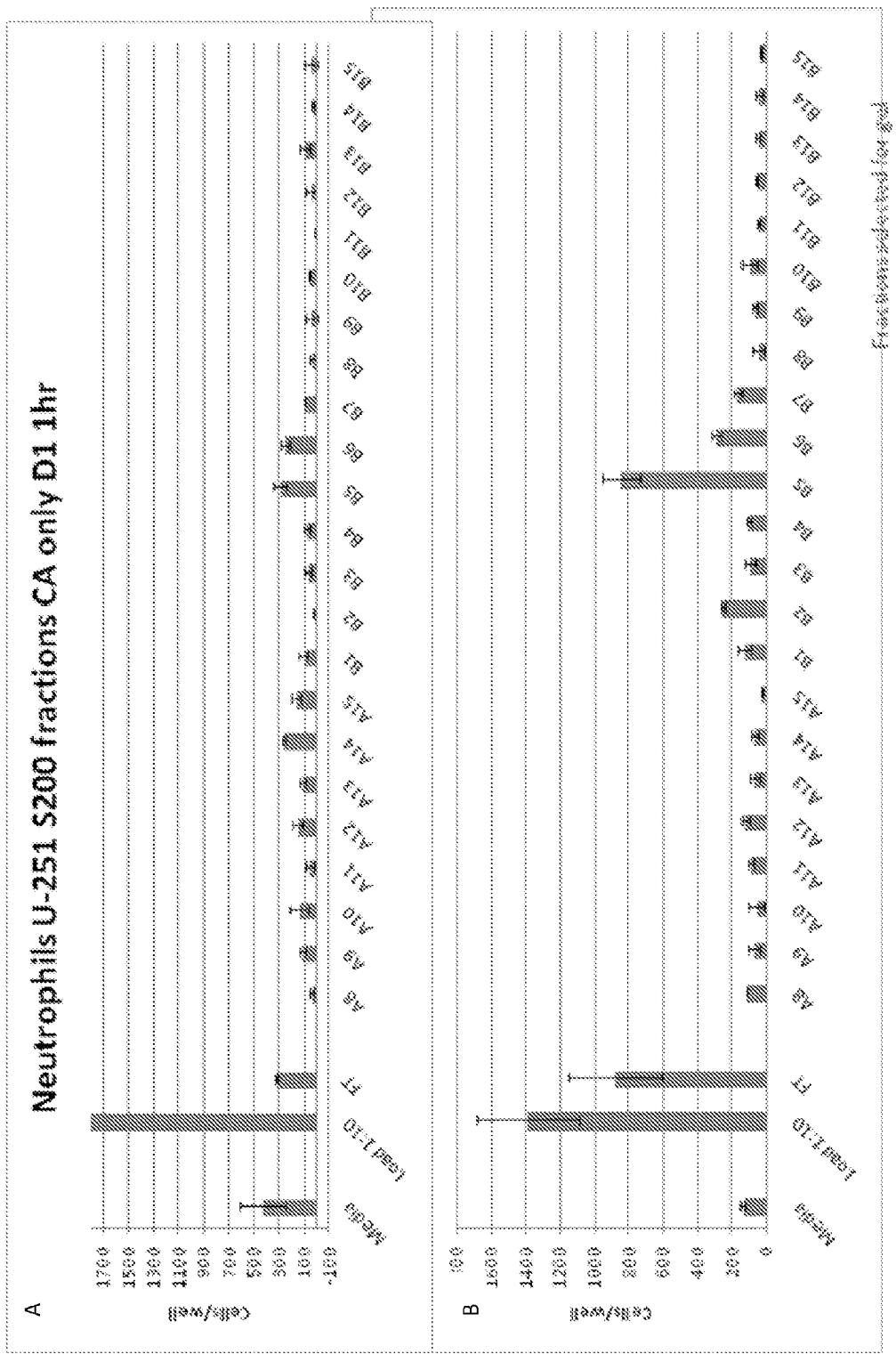
FIGS. 29A and B are bar graphs showing induction (number of cells per well) of chemoattraction (A) and chemorepulsion (B) of neutrophils treated with U-251 size exclusion fractions.
Figure 30:
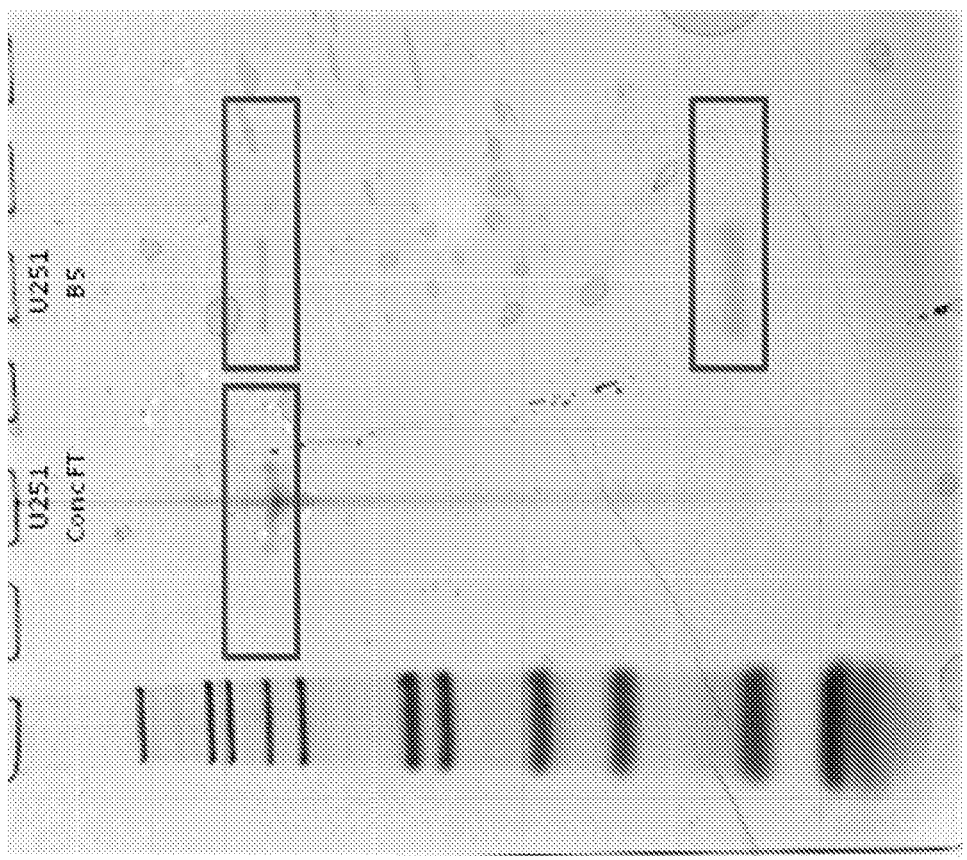
FIG. 30 is a photograph of an SDS PAGE gel of supernatant fractions from U-251 supernatant fractions.
Figure 31:
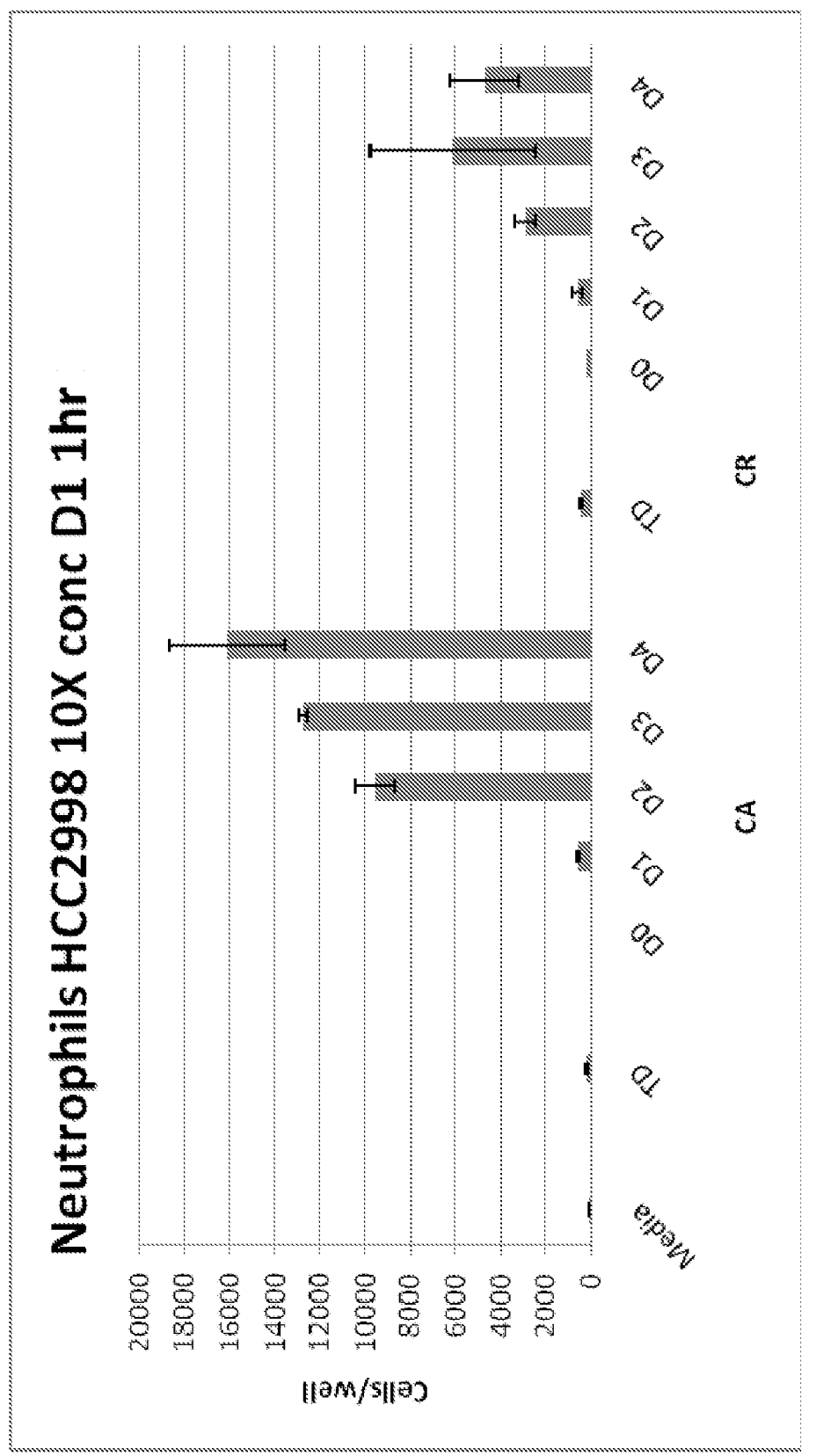
FIG. 31 is a bar graph showing induction (number of cells per well) of chemorepulsion (right) and chemoattraction (left) treated with HCC-2998 supernatants collected from day 0 (d0) to day 4 (d4) and TD control.
Figure 32:
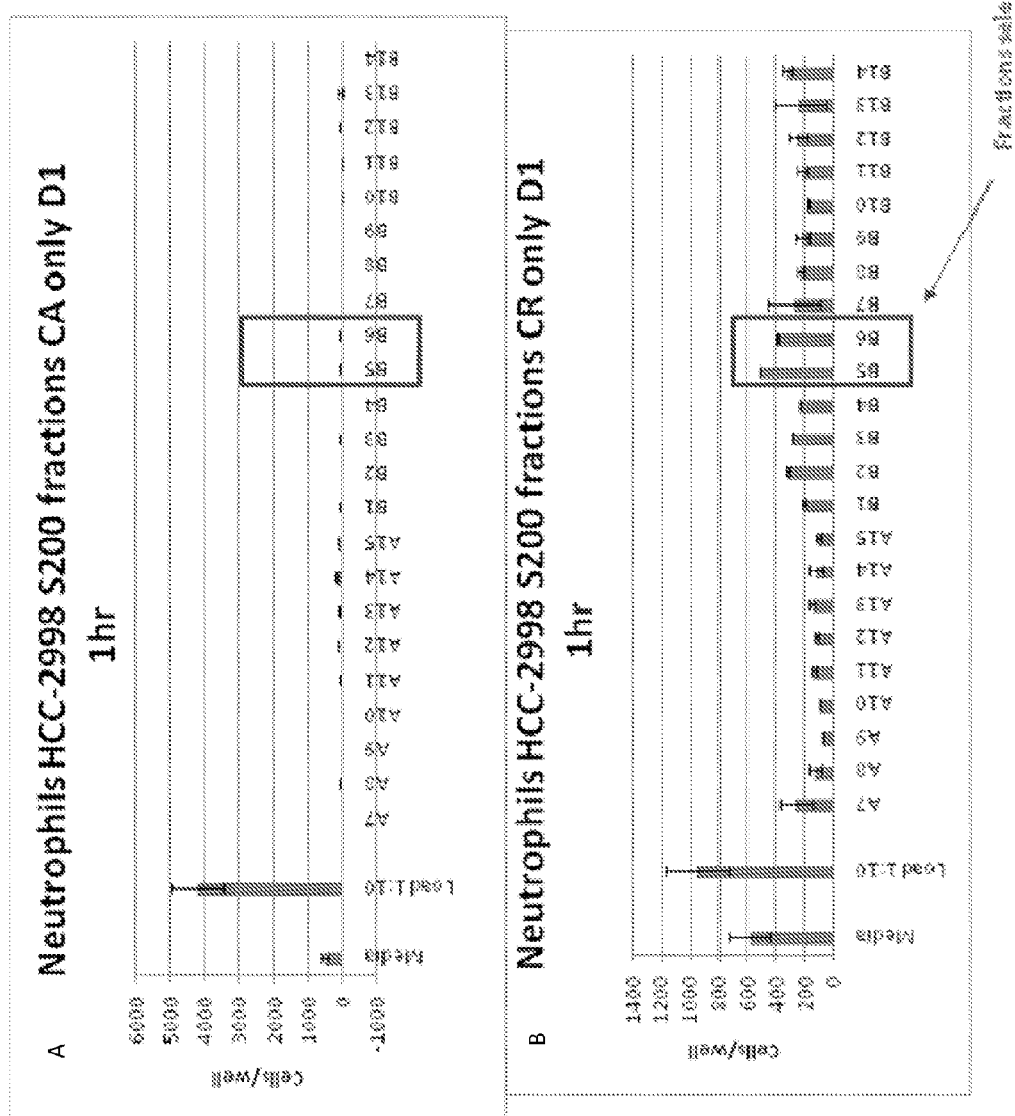
FIGS. 32A and 32B are bar graphs showing induction (number of cells per well) of chemoattraction (A) and chemorepulsion (B) of neutrophils treated with HCC-2998 size exclusion fractions.
Figure 33:
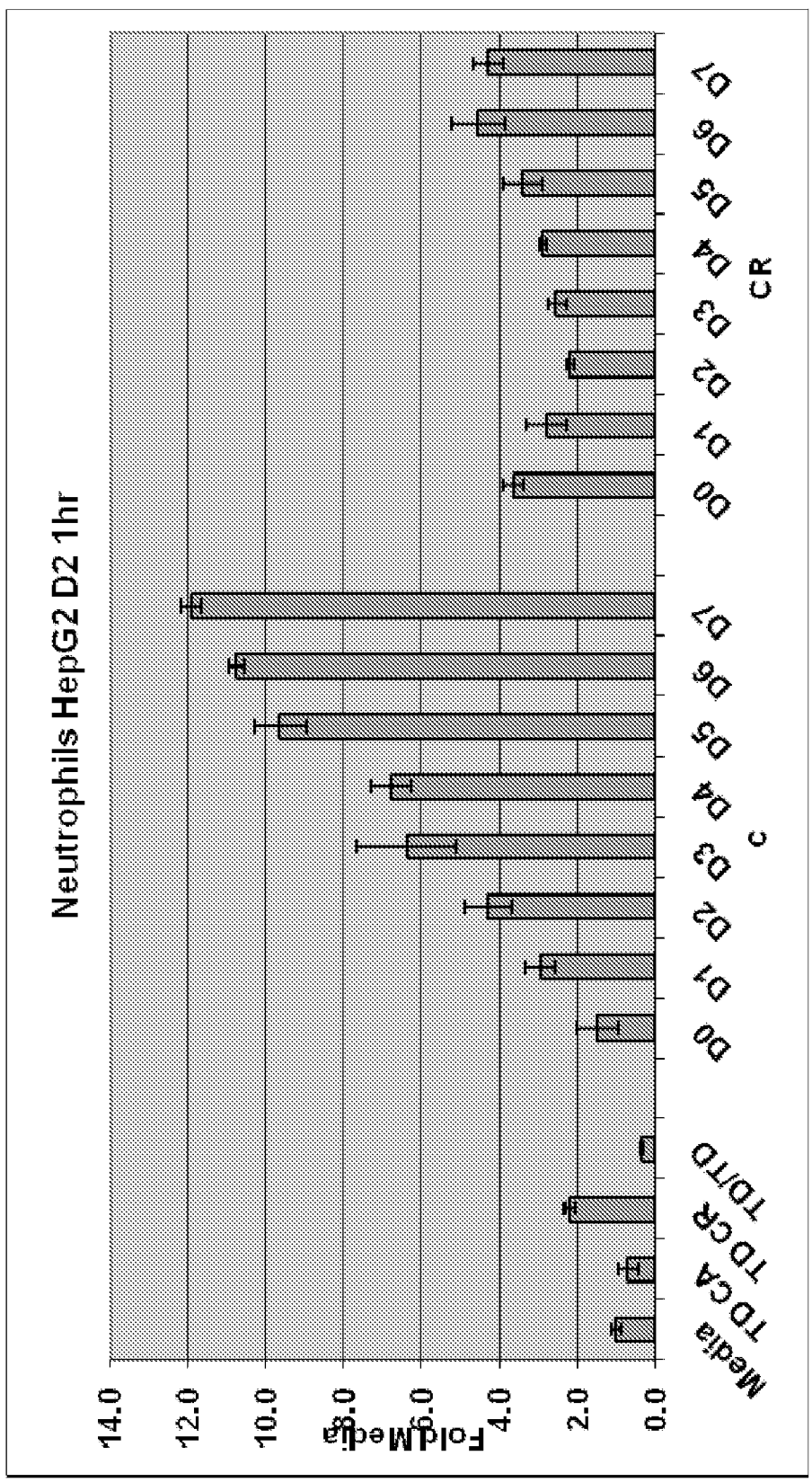
FIG. 33 is a bar graph showing fold induction (over media) of chemoattraction (left) and chemorepulsion (right) of HepG2 supernatant fractions collected from day 0 (d0) to day 7 (d7).
Figure 34:
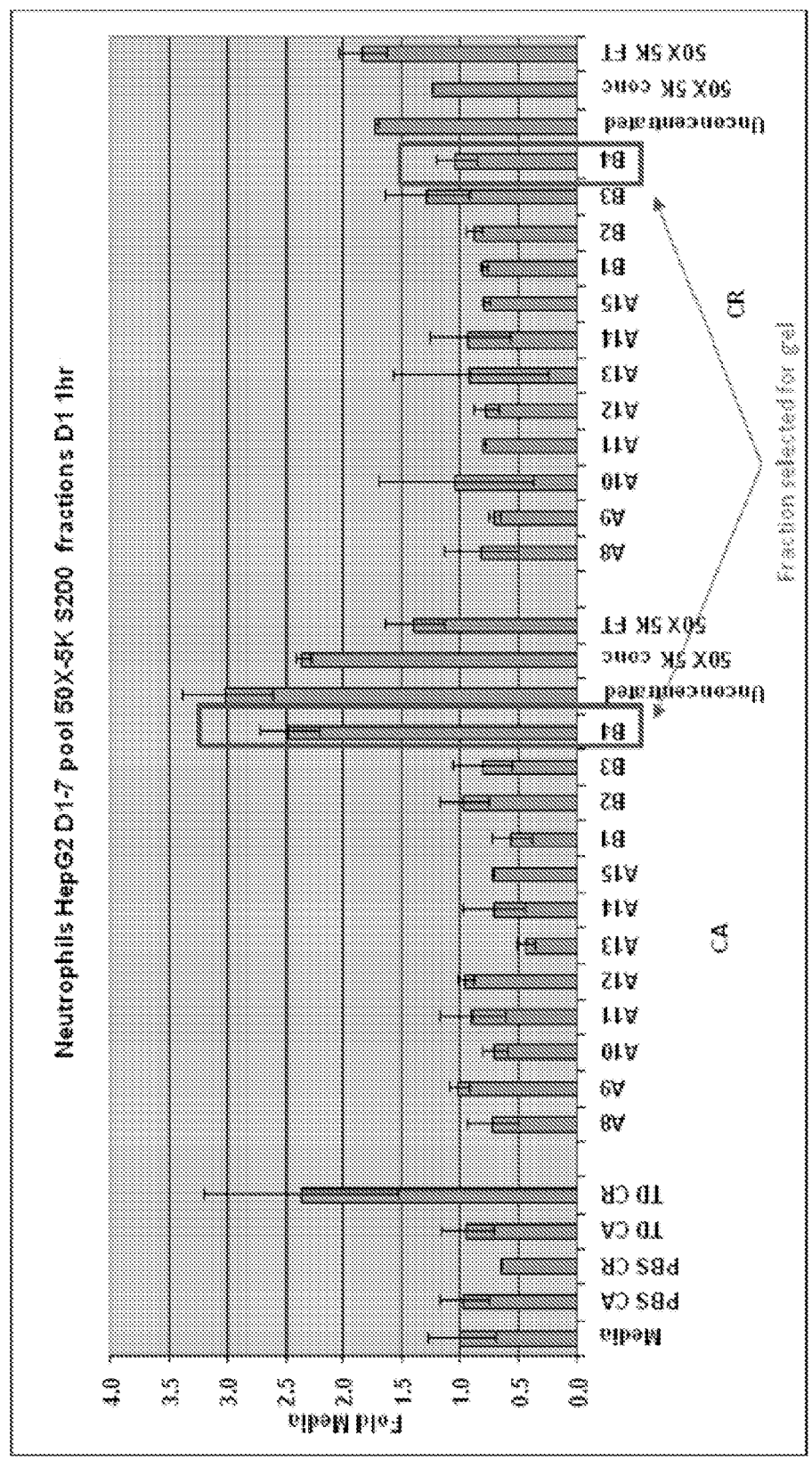
FIG. 34 is a bar graph showing fold induction (over media) of chemoattraction (left) and chemorepulsion (right) of HepG2 size exclusion fractions.
Figure 35:
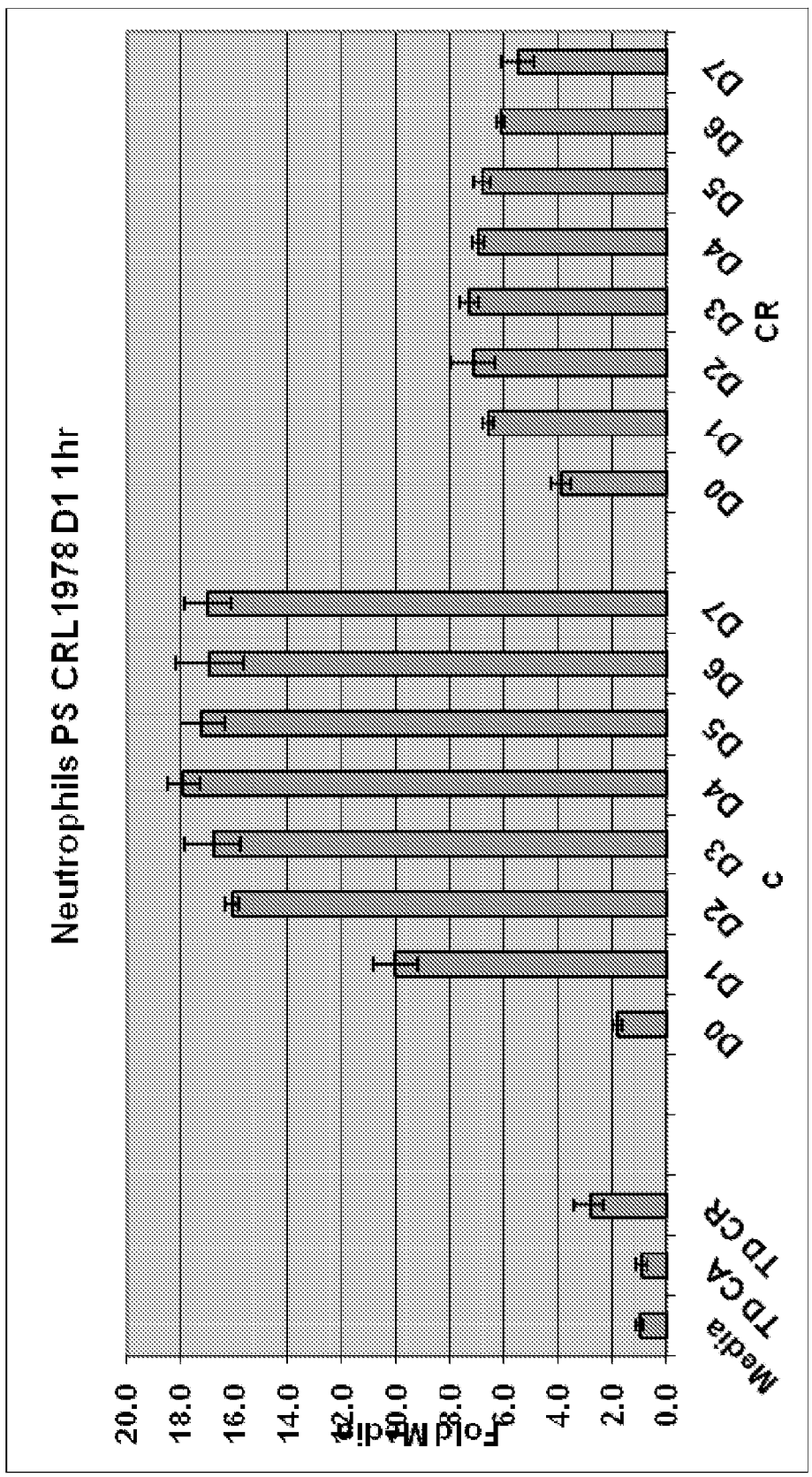
FIG. 35 is a bar graph showing fold induction (over media) of chemoattraction (left) or chemorepulsion (right) of neutrophils treated with CRL-1978 supernatants collected from day 0 (d0) to day 7 (d7) and TD control.
Figure 36:
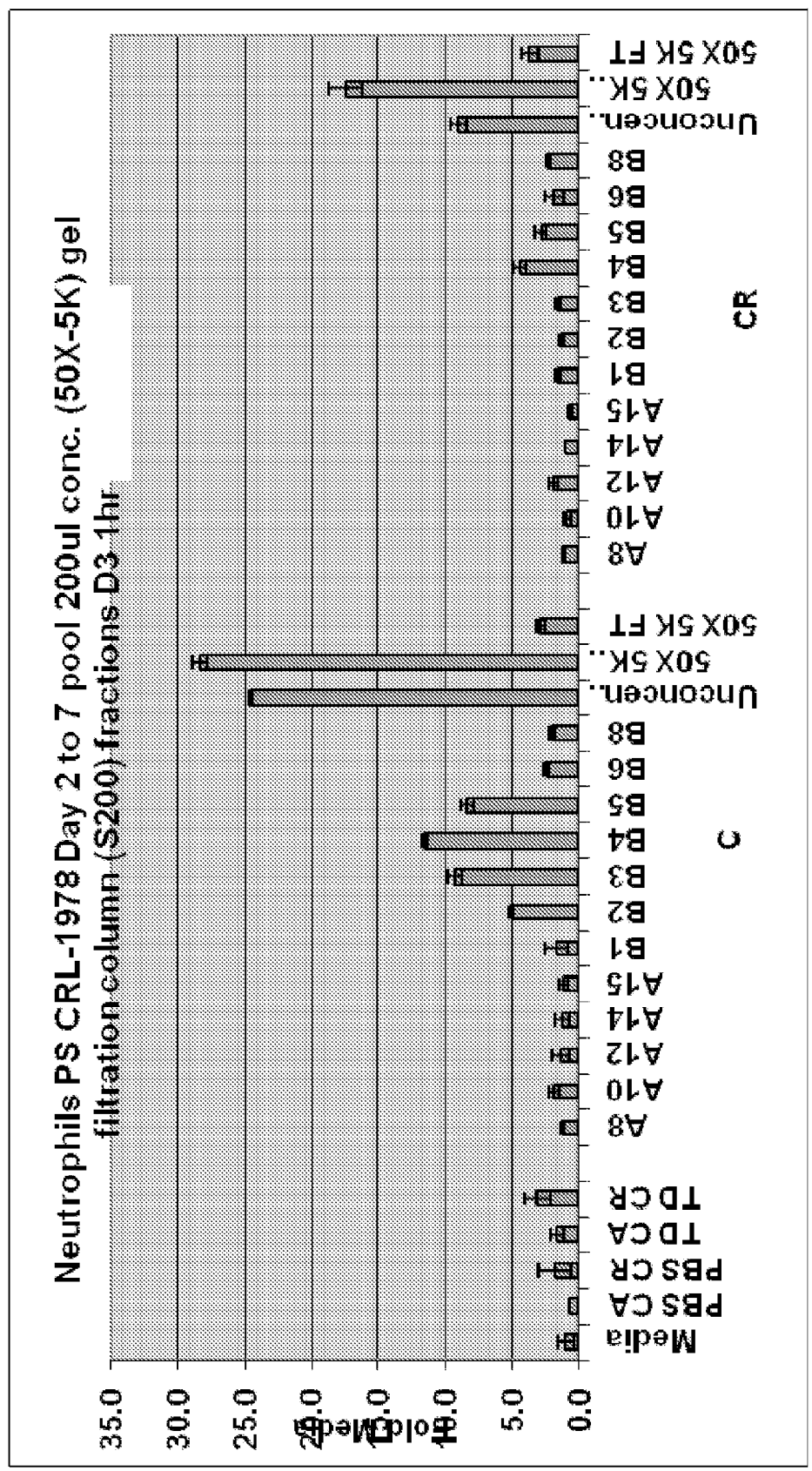
FIG. 36 is a bar graph showing fold induction (over media) of chemoattraction (left) or chemorepulsion (right) of neutrophils treated with CRL-1978 size exclusion fractions.
Figure 37:
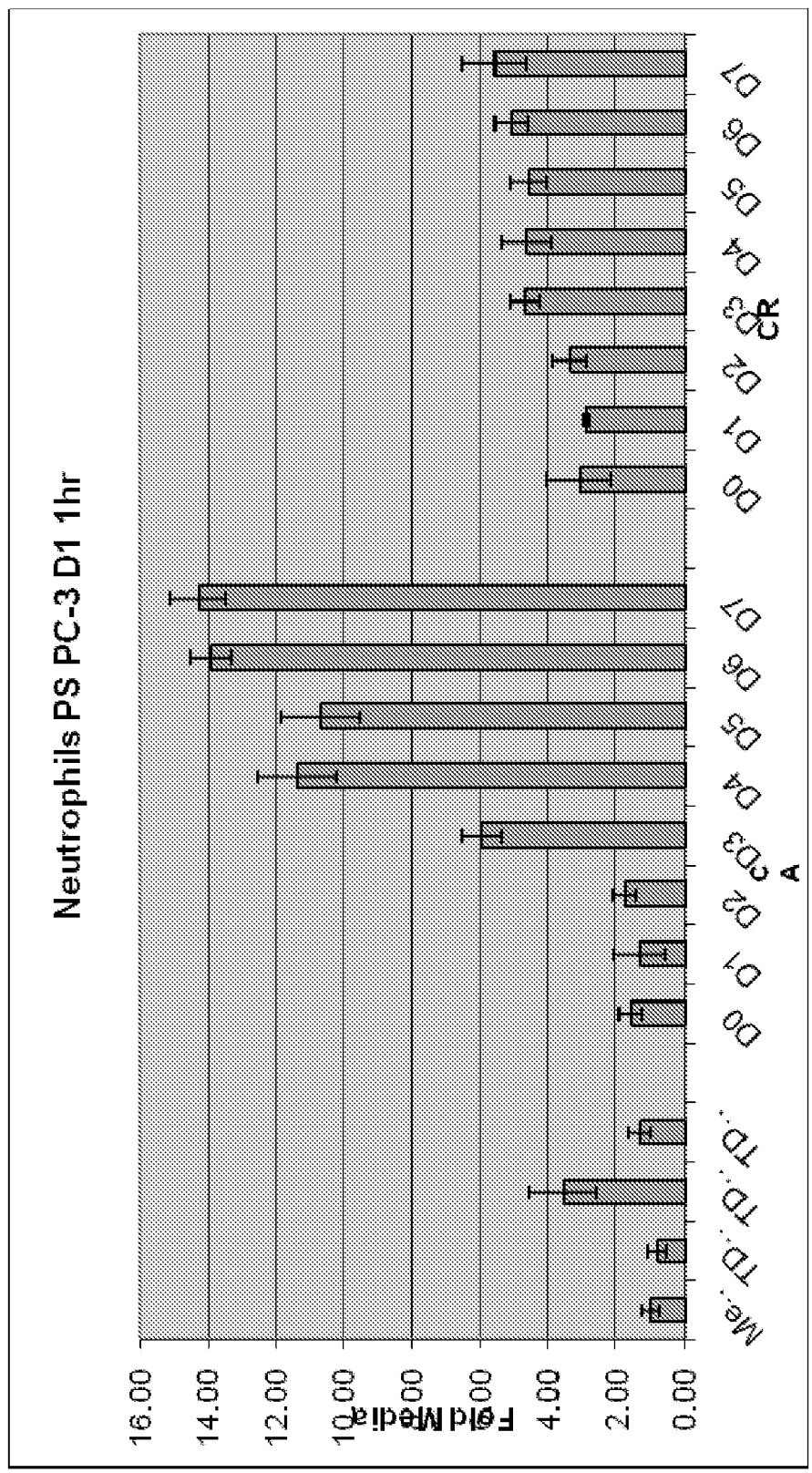
FIG. 37 is a bar graph showing fold induction (over media) of chemoattraction (left) or chemorepulsion (right) of neutrophils treated with PC3 supernatants from day 0 (d0) to day 7 (d7) and TD control.
Figure 38:
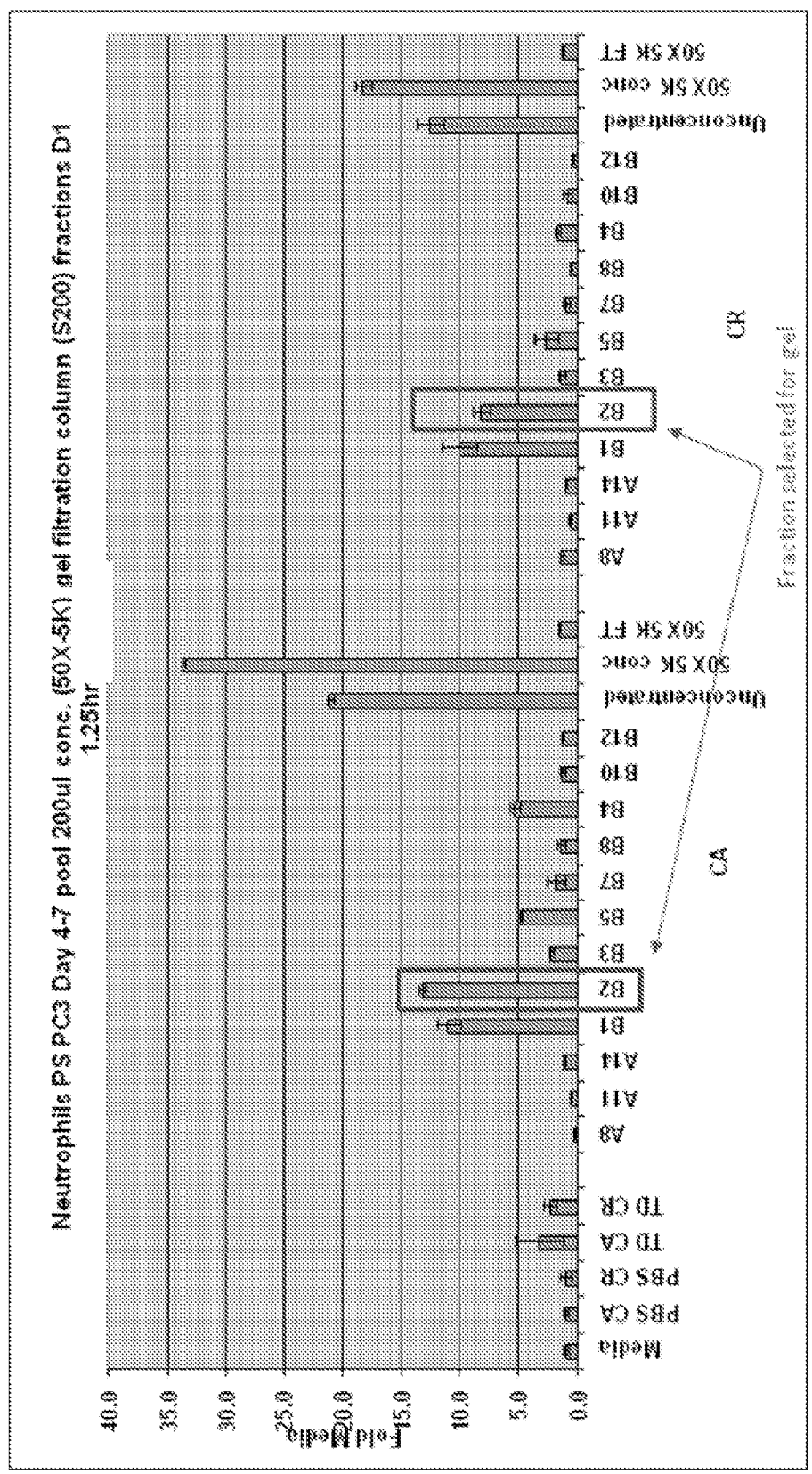
FIG. 38 is a bar graph showing fold induction (over media) of chemoattraction (left) or chemorepulsion (right) of neutrophils treated with PC3 size exclusion fractions.
Figure 39:
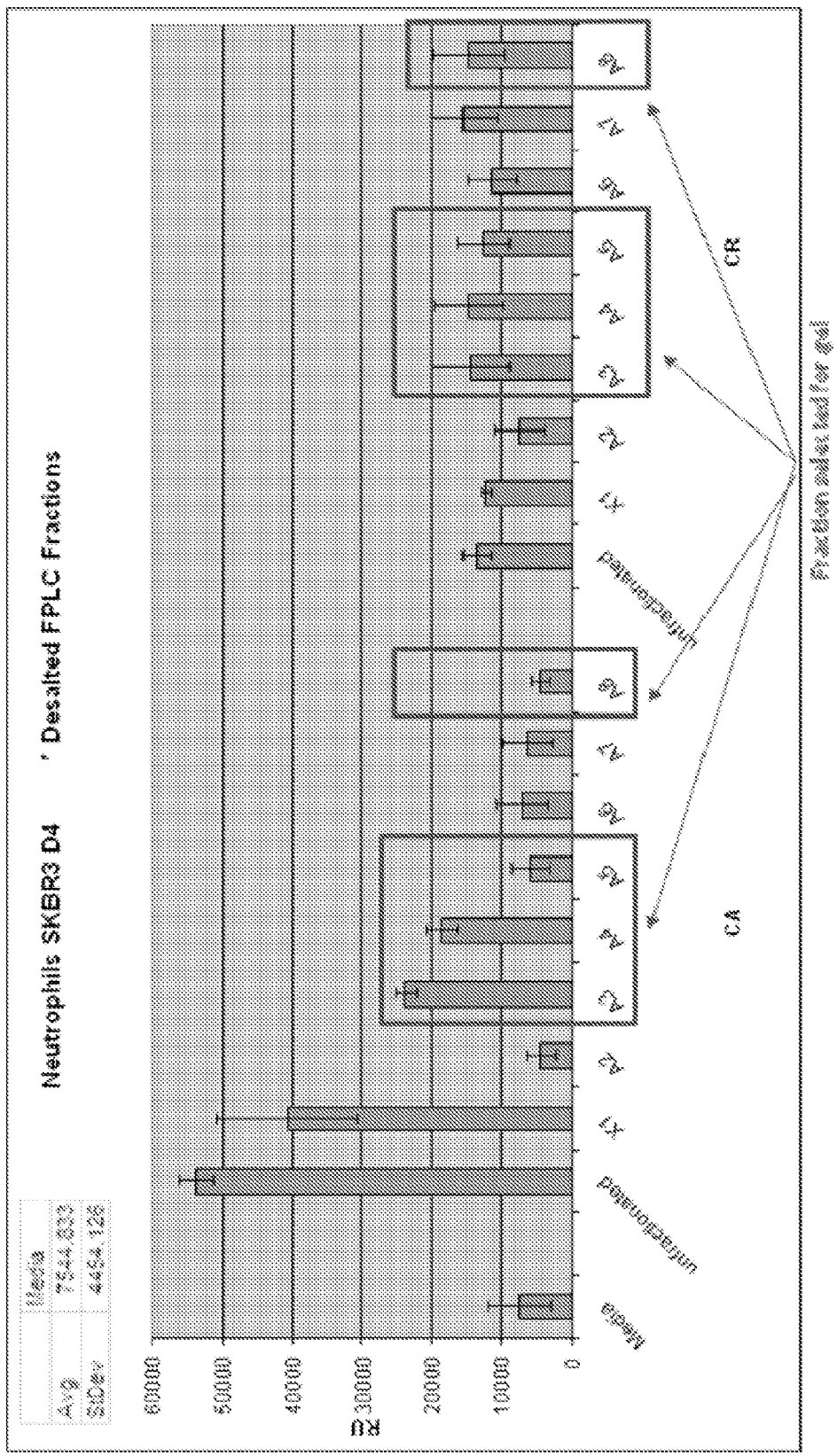
FIG. 39 is a bar graph showing RU of chemoattraction (left) and chemorepulsion (right) of neutrophils treated with SK-BR-3 anion exchange fractions (A2-A8) and media.
Figure 40:
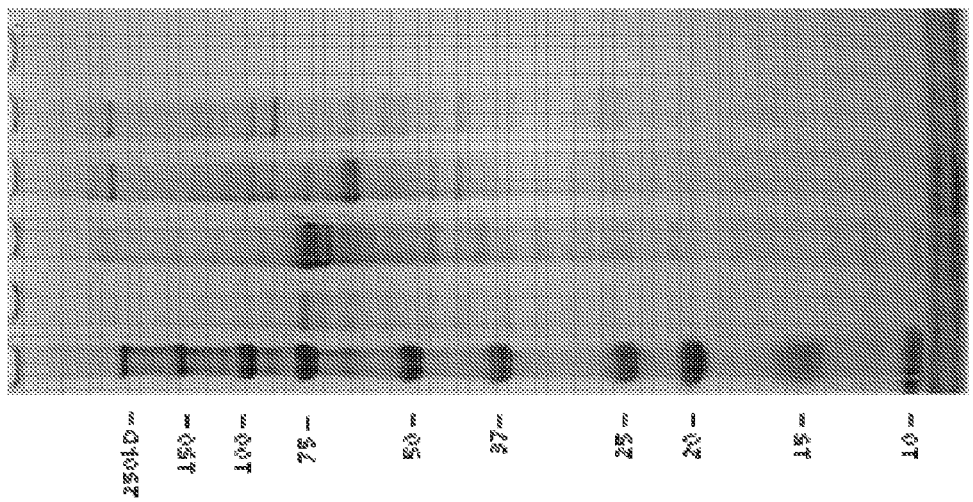
FIG. 40 is a photograph of a gel (Comassie Stain) of SK-BR-3 anion exchange fractions submitted for mass spectrometry (MS) analysis.

FIG. 6: Effect of hemopexin on migration of human neutrophils. Hemopexin was evaluated at different concentrations for its ability to induce chemoattraction (CA) and chemorepulsion (CR) of human neutrophils using a Boyden chamber transwell migration assay. Human neutrophils were effectively attracted at 8.8 microM concentration of hemopexin.

Example 2

Identification of Modulators of Cell Migration Present in Mammalian Cancer Cell Line Supernatants Objective: To identify the agents present in mammalian cancer cell lines that have the ability to modulate the migration of immune cell subsets.
Materials and Methods:
Mammalian Cancer Cell Lines:
Cancer cell lines were cultured in serum containing media until desired confluence is reached. Culture conditions were switched to serum-free media and supernatants collected everyday up to certain number of days. The supernatants were supplemented with cocktail of protease inhibitors and divided into aliquots and stored at −80 C until further processing. Depending on the volume of culture supernatant, they were either concentrated 10 times or evaluated unconcentrated to study their effects on neutrophil migration Boyden chamber transwell migration assays.
Chromatographic Separation:
Supernatants were further concentrated and loaded on a Superdex 200 10/300 GL column (GE Healthcare) and fractionated at the rate of 0.5 ml/min. Fractions (1 ml) were collected in tubes preloaded with 10 ul of 100× concentration Complete EDTA-free Protease Inhibitor Cocktail (Roche). These fractions were evaluated for chemoattraction (CA) and chemorepulsion (CR) activities in transwell migration assays described below.

Supernatants for the breast cancer cell line, SK-BR-3 were first dialyzed overnight and then loaded on a HiTrap-Q Fast Flow anion exchange column and fractionated at a rate of 1 mL/min. 3 mL fractions were desalted and evaluated for chemoattraction (CA) and chemorepulsion (CR) activities in transwell migration assays as described below.
One Dimensional SDS-PAGE Analysis:

Fractions collected from S-200 and anion exchange chromatography with CR activity and the adjacent fractions without CR activity were further fractionated by one dimensional SDS-PAGE. Proteins bands differentially present in S-200 fractions with CR activity were excised manually, digested with trypsin, and subjected to LC-MS/MS.

The chemorepulsive activity of the supernatants, fractions collected from S-200 and anion exchange chromatography and the proteins listed below were determined as follows:
Transwell Migration Assay:
1. Prior to beginning the assay, the following were prepared:
   a. 0.5% Fetal Calf Serum (FCS) in Iscove's Modified Dulbecco's Medium (IMDM) (Assay Medium) (Both from ATCC).
   b. Migratory cells at a concentration of $2\times10_7$ cells/ml in Assay Medium.
2. The assay plates are Neuroprobe ChemoTx plates, part number 206-3 (3 um pore size) for neutrophils.
3. 31 µl of the following solutions were pipetted into each well:
   a. For media controls and for chemorepulsion samples, Assay Medium was used.
   b. For chemoattraction samples, appropriate dilution of ligand was used.
4. The membrane was carefully placed onto the plate, starting at one side and then slowly lowering the other edge onto the plate.
5. 29 µl of the following were pipetted onto the top of each circle:
   a. For media controls and chemoattraction samples, Assay Medium was used.
   b. For chemorepulsion samples, the appropriate dilution of ligand was used.
6. 2 µl of cells (40,000 cells) were added to each bubble of liquid from step 7.
7. The plate was covered with the supplied lid and incubated for 1 hour at 37° C. in 5% $CO_2$.
8. The liquid was then removed from the top of the plate using a Kimwipe.
9. The plate was then examined under a microscope to look for crystallization, contamination and overall migration.
From this point assay plates were either processed by method A: CTG (Cell Titer Glo via relative luminescence units for read out) or method B: Guava (via cell count for read out).
Method A:
1. White read plates were preloaded with 25 ul PBS and 5 ul of Cell Titer Glo (Promega #G7572) was added to each well of the transmigration plate.
2. Using a multichannel pipettor set at 30 ul, lysed cell solution was transferred to white read plates pre-loaded with PBS.
3. The plate was read using the BioTek Synergy4 plate reader in order to quantify the number of migrated cells.

Method B:
- U-bottom 96 well plates were preloaded with 50 ul assay media and the contents of the Neuroprobe plates were transferred to the U-bottom plate.
- Equal volumes of Guava viacount reagent was added to each well to stain the cells. The plate was then incubated for 5 minutes in the dark at room temperature.
- 1% paraformaldehyde was added to fix the cells and they were then sealed with adhesive film and stored at 4° C. overnight.
- The Guava Easy Cyte Plus was used to read the plate and quantify the number of migrated cells.

Bands from supernatant fractions that exhibited chemorepulsive activity were sent out for MS (Liquid chromatography/Mass Spectrometry/Mass Spectrometry) analysis (outsourced). Commercially available proteins corresponding to proteins identified in Mass Spectrometry were then tested in cell migration assay.

Protein identification was performed by outside sources using nano LC/MS/MS (Liquid Chromatography/Mass Spectrometry/Mass Spectrometry) on an LTQ ("linear trap quadrupole") mass spectrometer. Protein samples were submitted in a gel or solution and were first digested robotically using trypsin to create a peptide mixture (alternate enzymes may be employed if necessary). Peptides were then injected on a custom-designed LC column set-up and eluted into the mass spectrometer where MS and MS/MS were performed. Product ion data was searched using forward and reversed database searching methods to allow assessment of false discovery rates and ensure only correct protein identifications were reported. Search results were parsed into the Scaffold™ visualization software to allow further validation of protein assignments through the ProteinProphet™ and PeptideProphet™[1] tools.

The methods used for In-gel digestion are as below:

Samples were subjected to proteolytic digestion on a ProGest workstation as follows:

The samples were reduced with DTT at 60° C., allowed to cool to room temperature, alkylated with iodoacetamide, incubated at 37° C. for 4 h in the presence trypsin and formic acid was added to stop the reaction.

The method used for Mass Spectrometry—Solution Based are below:

Samples were subjected to C18 capture using ZipTips. They were aspirated across equilibrated C18 ZipTip, washed in 0.1% formic acid, eluted in 80% acetonitrile in 0.1% formic acid, concentrated by vacuum centrifugation and resuspended in 0.1% formic acid for injection.

The methods used for LC/MS/MS (data-dependent) are as below:

Samples were analyzed by nano LC/MS/MS on a ThermoFisher LTQ XL or Orbitrap XL. 30 µl of hydrolysate were loaded on a 75 µm C12 vented column at a flow-rate of 10 µL/min and eluted at 300 nL/min and a 1 h gradient was employed.

MS/MS data were searched using a local copy of Mascot (www.matrixscience.com)

The parameters for all LC/MS/MS (Mascot) searches were as follows:

Type of search: MS/MS Ion Search
Enzyme: Trypsin
Fixed modifications: Carbamidomethyl (C)
Variable modifications: Oxidation (M, Acetyl (N-term, Pyro-glu (N-term Q)
Mass values: Monoisotopic
Protein Mass: Unrestricted
Peptide Mass Tolerance: ±10 ppm (Orbitrap); ±2.0 Da (LTQ)
Fragment Mass Tolerance: ±0.5 Da (LTQ)
Max Missed Cleavages: 1

Samples were processed in the Scaffold™ Algorithm (www.proteomesoftware.com) using .DAT files generated by MASCOT™. Parameters for LTQ data require a minimum of 3 peptides matching per protein with minimum probabilities of 95% at the protein level and 50-80% at the corresponding peptide level. QTOF/Orbitrap data require a minimum of 2 peptides with the same minimum probability thresholds due to the superior mass accuracy of that instrument.

NOTE: Detailed protocols for each of these methods can be found in the technical information section of http://www-.prsproteomics.com.

NOTE: SK-BR-3 was outsourced using LC/MS/MS performed at University of Georgia, Proteomics Resource Facility.

Results:

The chemorepulsive activity of supernatants, fractions collected from chromatography and commercially available proteins are shown in FIGS. 7-39.

Proteins identified in the chemorepulsive supernatant fractions by LC/MS/MS (mass spectrometry) are shown in the Tables below:

TABLE 2

Proteins identified by MS in Renal Cell Lines ACHN and 786-O

| Protein: | Accession # |
|---|---|
| ACBD3 Golgi resident protein GCP60 | IPI00009315 |
| ADPRHL2 Poly(ADP-ribose) glycohydrolase ARH3 | IPI00015865 |
| AK2 Isoform 1 of Adenylate kinase isoenzyme 2, mitochondrial | IPI00215901 (+1) |
| AKR1A1 Alcohol dehydrogenase | IPI00220271 |
| AKR1B1 Aldose reductase | IPI00413641 |
| AKR1B10 Aldo-keto reductase family 1 member B10 | IPI00105407 |
| AKR1C1 Aldo-keto reductase family 1 member C1 | IPI00029733 |
| AKR1C2 Aldo-keto reductase family 1 member C2 | IPI00005668 |
| AKR1C3 Aldo-keto reductase family 1 member C3 | IPI00291483 (+1) |
| ANP32B Isoform 1 of Acidic leucine-rich nuclear phosphoprotein 32 family member B | IPI00007423 (+1) |
| ANXA1 Annexin A1 | IPI00218918 |
| ANXA2 Annexin A2 | IPI00455315 |
| APEX1 DNA-(apurinic or apyrimidinic site) lyase | IPI00215911 |
| APOA1BP Isoform 1 of Apolipoprotein A-I-binding protein precursor | IPI00168479 (+1) |
| ARHGDIA Rho GDP-dissociation inhibitor 1 | IPI00003815 (+1) |
| ARMET Protein ARMET precursor | IPI00328748 |
| ASF1A Histone chaperone ASF1A | IPI00292168 |

TABLE 2-continued

Proteins identified by MS in Renal Cell Lines ACHN and 786-O

| Protein: | Accession # |
|---|---|
| BSG Isoform 2 of Basigin precursor | IPI00019906 (+1) |
| C11orf54 Isoform 3 of Ester hydrolase C11orf54 | IPI00061507 (+2) |
| C19orf33 Isoform 1 of Immortalization up-regulated protein | IPI00030767 |
| C1orf128 Isoform 1 of UPF0424 protein C1orf128 | IPI00015351 |
| C7orf24 Uncharacterized protein C7orf24 | IPI00031564 |
| CA12 Isoform 1 of Carbonic anhydrase 12 precursor | IPI00012895 (+1) |
| CA2 Carbonic anhydrase 2 | IPI00218414 (+1) |
| CAB39 Calcium-binding protein 39 | IPI00032561 |
| CALD1 Isoform 4 of Caldesmon | IPI00218696 |
| CALM2; CALM1; CALM3 Calmodulin | IPI00075248 (+2) |
| CAPG Macrophage-capping protein | IPI00027341 (+1) |
| CAPZA2 F-actin-capping protein subunit alpha-2 | IPI00026182 (+3) |
| CASP3 Caspase-3 precursor | IPI00292140 |
| CAST Isoform 2 of Calpastatin | IPI00220857 (+11) |
| CCDC25 Coiled-coil domain-containing protein 25 | IPI00396174 (+1) |
| CDH13 Cadherin-13 precursor | IPI00024046 (+2) |
| CDV3 Isoform 1 of Protein CDV3 homolog | IPI00014197 (+2) |
| CFL1 Cofilin-1 | IPI00012011 |
| CFL2 Cofilin-2 | IPI00413344 |
| CHAC2 Cation transport regulator-like protein 2 | IPI00103047 |
| CIAPIN1 Isoform 3 of Anamorsin | IPI00025333 (+1) |
| CMBL Carboxymethylenebutenolidase homolog | IPI00383046 |
| CMPK1 cDNA, FLJ93091, *Homo sapiens* UMP-CMP kinase (UMP-CMPK), mRNA | IPI00219953 |
| CNBP Isoform 1 of Cellular nucleic acid-binding protein | IPI00430812 (+6) |
| CNPY2 Isoform 1 of Protein canopy homolog 2 precursor | IPI00443909 |
| CRK v-crk sarcoma virus CT10 oncogene homolog isoform b | IPI00305469 |
| CRYZ Quinone oxidoreductase | IPI00000792 |
| CTSS Cathepsin S precursor | IPI00299150 |
| CTSZ Cathepsin Z precursor | IPI00002745 (+1) |
| CYR61 CYR61 protein | IPI00006273 (+2) |
| DDAH1 N(G),N(G)-dimethylarginine dimethylaminohydrolase 1 | IPI00220342 |
| DDX21 Isoform 1 of Nucleolar RNA helicase 2 | IPI00015953 |
| DSTN Destrin | IPI00473014 |
| DTD1 D-tyrosyl-tRNA(Tyr) deacylase 1 | IPI00152692 |
| DUT Isoform DUT-M of Deoxyuridine 5'-triphosphate nucleotidohydrolase, mitochondrial precursor | IPI00013679 (+3) |
| EEF1G Elongation factor 1-gamma | IPI00000875 (+1) |
| EIF1AY Eukaryotic translation initiation factor 1A, Y-chromosomal | IPI00023004 (+1) |
| EIF4B Eukaryotic translation initiation factor 4B | IPI00012079 (+1) |
| EIF5A Isoform 2 of Eukaryotic translation initiation factor 5A-1 | IPI00376005 (+1) |
| EIF6 Eukaryotic translation initiation factor 6 | IPI00010105 |
| ERP29 Endoplasmic reticulum protein ERp29 precursor | IPI00024911 |
| FAHD1 Isoform 2 of Fumarylacetoacetate hydrolase domain-containing protein 1 | IPI00440828 (+2) |
| FAM3C Protein FAM3C precursor | IPI00334282 |
| FER1L3 Isoform 1 of Myoferlin | IPI00021048 (+5) |
| FLNA filamin A, alpha isoform 1 | IPI00302592 (+3) |
| FLNC Isoform 1 of Filamin-C | IPI00178352 (+1) |
| GLO1 Lactoylglutathione lyase | IPI00220766 |
| GRB2 Isoform 1 of Growth factor receptor-bound protein 2 | IPI00021327 (+1) |
| GSTM3 Glutathione S-transferase Mu 3 | IPI00246975 |
| GSTP1 Glutathione S-transferase P | IPI00219757 (+1) |
| GUK1 Guanylate kinase | IPI00182293 (+3) |
| HDDC2 Isoform 2 of HD domain-containing protein 2 | IPI00386751 (+1) |
| HDGF Hepatoma-derived growth factor | IPI00020956 |
| HDHD1A Haloacid dehalogenase-like hydrolase domain containing protein | IPI00302436 |
| HDHD3 Haloacid dehalogenase-like hydrolase domain-containing protein 3 | IPI00009931 |
| HLA-B; HLA-A; HLA-C; LOC441528; XXbac-BPG181B23.1; LOC728687; MICA; LOC100133382 HLA class I histocompatibility antigen, B-42 alpha chain precursor | IPI00472676 (+2) |
| HMGA1 Isoform HMG-I of High mobility group protein HMG-I/HMG-Y | IPI00179700 |
| HMGB3 High mobility group protein B3 | IPI00217477 (+2) |
| HMGN1 Non-histone chromosomal protein HMG-14 | IPI00554761 |
| HN1 Isoform 1 of Hematological and neurological expressed 1 protein | IPI00007764 (+1) |
| HNRNPA2B1 Isoform B1 of Heterogeneous nuclear ribonucleoproteins A2/B1 | IPI00396378 |
| HPRT1 Hypoxanthine-guanine phosphoribosyltransferase | IPI00218493 |
| IAH1 Isoamyl acetate-hydrolyzing esterase 1 homolog | IPI00419194 (+1) |
| IGFBP7 Insulin-like growth factor-binding protein 7 precursor | IPI00016915 |
| IGSF8 Isoform 1 of Immunoglobulin superfamily member 8 precursor | IPI00056478 (+1) |
| IL6 Interleukin-6 precursor | IPI00007793 (+2) |
| ITIH5 inter-alpha trypsin inhibitor heavy chain precursor 5 isoform 1 | IPI00328829 (+1) |
| KIAA0174 Isoform 1 of Uncharacterized protein KIAA0174 | IPI00024660 (+2) |
| LASP1 Isoform 1 of LIM and SH3 domain protein 1 | IPI00000861 (+2) |
| LDHB L-lactate dehydrogenase B chain | IPI00219217 |
| LMAN2 Vesicular integral-membrane protein VIP36 precursor | IPI00009950 |

TABLE 2-continued

Proteins identified by MS in Renal Cell Lines ACHN and 786-O

| Protein: | Accession # |
|---|---|
| LMNA Isoform A of Lamin-A/C | IPI00021405 (+4) |
| LMNB1 Lamin-B1 | IPI00217975 |
| LMNB2 Lamin-B2 | IPI00009771 (+1) |
| LOC100130561; HMG1L10 High mobility group protein 1-like 10 | IPI00018755 (+3) |
| M6PRBP1 Isoform A of Mannose-6-phosphate receptor-binding protein 1 | IPI00106668 (+1) |
| MAP1B Microtubule-associated protein 1B | IPI00008868 |
| MAPRE1 Microtubule-associated protein RP/EB family member 1 | IPI00017596 |
| MCM3 DNA replication licensing factor MCM3 | IPI00013214 |
| MDH1 Malate dehydrogenase, cytoplasmic | IPI00291005 |
| MDH2 Malate dehydrogenase, mitochondrial precursor | IPI00291006 |
| MMP14 Matrix metalloproteinase-14 precursor | IPI00218398 (+1) |
| NENF Neudesin precursor | IPI00002525 |
| NIPSNAP3A Protein NipSnap homolog 3A | IPI00004845 (+1) |
| NME2 Nucleoside diphosphate kinase | IPI00604590 (+1) |
| NPC2 Epididymal secretory protein E1 precursor | IPI00301579 |
| NPM1 Isoform 2 of Nucleophosmin | IPI00220740 (+2) |
| NQO2 Ribosyldihydronicotinamide dehydrogenase | IPI00219129 (+3) |
| NUDT1 Isoform p26 of 7,8-dihydro-8-oxoguanine triphosphatase | IPI00004392 (+4) |
| PARK7 Protein DJ-1 | IPI00298547 |
| PDAP1 28 kDa heat- and acid-stable phosphoprotein | IPI00013297 |
| PDIA6 Isoform 2 of Protein disulfide-isomerase A6 precursor | IPI00299571 (+1) |
| PEBP1 Phosphatidylethanolamine-binding protein 1 | IPI00219446 |
| PGLS 6-phosphogluconolactonase | IPI00029997 |
| PIR Pirin | IPI00012575 |
| PNPO Pyridoxine-5'-phosphate oxidase | IPI00018272 (+1) |
| POLDIP2 Polymerase delta-interacting protein 2 | IPI00165506 |
| POLR2H DNA-directed RNA polymerases I, II, and III subunit RPABC3 | IPI00003309 |
| PPIA Peptidyl-prolyl cis-trans isomerase A | IPI00419585 (+4) |
| PPIB peptidylprolyl isomerase B precursor | IPI00646304 |
| PPIF Peptidyl-prolyl cis-trans isomerase, mitochondrial precursor | IPI00026519 |
| PPP1R14C Protein phosphatase 1 regulatory subunit 14C | IPI00290397 |
| PRDX1 Peroxiredoxin-1 | IPI00000874 (+1) |
| PRDX2 Peroxiredoxin-2 | IPI00027350 |
| PRDX3 Thioredoxin-dependent peroxide reductase, mitochondrial precursor | IPI00024919 (+1) |
| PRDX6 Peroxiredoxin-6 | IPI00220301 |
| PROCR Endothelial protein C receptor precursor | IPI00009276 |
| PSPH Phosphoserine phosphatase | IPI00019178 |
| PTGDS Prostaglandin-H2 D-isomerase precursor | IPI00013179 (+2) |
| PTGR1 NADP-dependent leukotriene B4 12-hydroxydehydrogenase | IPI00292657 |
| PTMS Parathymosin | IPI00550020 |
| QDPR Dihydropteridine reductase | IPI00014439 |
| RAB11B Ras-related protein Rab-11B | IPI00020436 (+2) |
| RAB1A Isoform 1 of Ras-related protein Rab-1A | IPI00005719 (+6) |
| RAB5C Ras-related protein Rab-5C | IPI00016339 |
| RAD23A UV excision repair protein RAD23 homolog A | IPI00008219 |
| RALA Ras-related protein Ral-A precursor | IPI00217519 (+1) |
| RBM8A Isoform 1 of RNA-binding protein 8A | IPI00001757 (+1) |
| REXO2 Isoform 1 of Oligoribonuclease, mitochondrial precursor (Fragment) | IPI00032830 (+1) |
| RNASET2 Isoform 1 of Ribonuclease T2 precursor | IPI00414896 (+1) |
| RPE Isoform 1 of Ribulose-phosphate 3-epimerase | IPI00335280 (+1) |
| RPIA Ribose-5-phosphate isomerase | IPI00026513 (+1) |
| SAMD9 Isoform 1 of Sterile alpha motif domain-containing protein 9 | IPI00217018 |
| S100A11 Protein S100-A11 | IPI00013895 |
| S100A6 Protein S100-A6 | IPI00027463 |
| SCYF1 Multisynthetase complex auxiliary component p43 | IPI00006252 (+1) |
| SERPINB6 Putative uncharacterized protein DKFZp686I04222 | IPI00413451 (+1) |
| SMAP1 Isoform 1 of Stromal membrane-associated protein 1 | IPI00102096 (+2) |
| SNX12 Isoform 1 of Sorting nexin-12 | IPI00438170 (+2) |
| SOD1 Superoxide dismutase | IPI00018733 (+1) |
| SOD2 Superoxide dismutase [Mn], mitochondrial precursor | IPI00022314 (+2) |
| sp_TRYP_PIG | IPIsp_TRYP_PIG |
| SPINT2 Kunitz-type protease inhibitor 2 precursor | IPI00011662 |
| STX7 Isoform 1 of Syntaxin-7 | IPI00289876 (+1) |
| SUB1 Activated RNA polymerase II transcriptional coactivator p15 | IPI00221222 |
| TAGLN2 Transgelin-2 | IPI00550363 |
| TALDO1 Transaldolase | IPI00744692 |
| THOC4 THO complex subunit 4 | IPI00328840 |
| TP53I3 Isoform 1 of Putative quinone oxidoreductase | IPI00384643 |
| TPI1 Isoform 1 of Triosephosphate isomerase | IPI00465028 |
| TPK1 Thiamin pyrophosphokinase 1 | IPI00072523 (+1) |
| TPT1 Translationally-controlled tumor protein | IPI00550900 |
| TRIOBP TRIO and F-actin binding protein isoform 1 | IPI00148768 (+8) |
| TWF1 Isoform 3 of Twinfilin-1 | IPI00815767 |
| TXNDC12 Thioredoxin domain-containing protein 12 precursor | IPI00026328 |
| TXNL1 Thioredoxin-like protein 1 | IPI00305692 (+1) |
| UBE2I SUMO-conjugating enzyme UBC9 | IPI00032957 (+2) |

TABLE 2-continued

Proteins identified by MS in Renal Cell Lines ACHN and 786-O

| Protein: | Accession # |
| --- | --- |
| UBE2L3 Ubiquitin-conjugating enzyme E2 L3 | IPI00021347 |
| UBE2N Ubiquitin-conjugating enzyme E2 N | IPI00003949 (+1) |
| UCHL1 Ubiquitin carboxyl-terminal hydrolase isozyme L1 | IPI00018352 |
| UCHL3 Ubiquitin carboxyl-terminal hydrolase isozyme L3 | IPI00011250 (+1) |
| Uncharacterized protein ENSP00000348237 | IPI00453476 (+1) |
| VAPA Vesicle-associated membrane protein-associated protein A | IPI00170692 (+1) |
| VEGFA vascular endothelial growth factor A isoform a precursor | IPI00012567 (+5) |
| VPS26A Vacuolar protein sorting-associated protein 26A | IPI00411426 |
| YWHAB Isoform Short of 14-3-3 protein beta/alpha | IPI00759832 |
| YWHAE 14-3-3 protein epsilon | IPI00000816 |
| YWHAG 14-3-3 protein gamma | IPI00220642 |
| YWHAQ 14-3-3 protein theta | IPI00018146 |
| YWHAZ 14-3-3 protein zeta/delta | IPI00021263 |
| KRT1 Keratin, type II cytoskeletal 1 | IPI00220327 (+1) |
| KRT10 Keratin, type I cytoskeletal 10 | IPI00009865 (+1) |
| KRT14 Keratin, type I cytoskeletal 14 | IPI00384444 |
| KRT16 Keratin, type I cytoskeletal 16 | IPI00217963 |
| KRT17 Keratin, type I cytoskeletal 17 | IPI00450768 |
| KRT2 Keratin, type II cytoskeletal 2 epidermal | IPI00021304 (+1) |
| KRT27 Keratin, type I cytoskeletal 27 | IPI00328103 |
| KRT5 Keratin, type II cytoskeletal 5 | IPI00009867 |
| KRT6A Keratin, type II cytoskeletal 6A | IPI00300725 |
| KRT73 Isoform 1 of Keratin, type II cytoskeletal 73 | IPI00174775 (+2) |
| KRT9 Keratin, type I cytoskeletal 9 | IPI00019359 (+1) |
| sp_ALBU_BOVIN | IPIsp_ALBU_BOVIN |

TABLE 3

Proteins identified by MS in glioma cell line SF-539:

| Protein: | Accession # |
| --- | --- |
| ACTA2 Actin, aortic smooth muscle | IPI00008603 (+16) |
| ACYP1 Acylphosphatase-1 | IPI00221117 (+1) |
| ACYP2 Acylphosphatase-2 | IPI00216461 (+1) |
| C19orf10 UPF0556 protein C19orf10 precursor | IPI00056357 |
| COTL1 Coactosin-like protein | IPI00017704 |
| CSTB Cystatin-B | IPI00021828 |
| CYCS Cytochrome c | IPI00465315 (+1) |
| DBI Isoform a 1 of Acyl-CoA-binding protein | IPI00010182 (+2) |
| FKBP1A FK506-binding protein 1A | IPI00873810 |
| FLG2 Filaggrin-2 | IPI00397801 |
| FN1 Isoform 1 of Fibronectin precursor | IPI00022418 (+15) |
| HNRNPH3 Isoform 1 of Heterogeneous nuclear ribonucleoprotein H3 | IPI00013877 (+3) |
| ISG15 Interferon-induced 17 kDa protein precursor | IPI00375631 |
| LGALS3 Galectin-3 | IPI00465431 |
| LYZ Lysozyme C precursor | IPI00019038 (+1) |
| MIF Macrophage migration inhibitory factor | IPI00293276 |
| MT2A Metallothionein-2 | IPI00022498 |
| NEDD8 NEDD8 precursor | IPI00020008 (+2) |
| PDIA3 Protein disulfide-isomerase A3 precursor | IPI00025252 |
| PFN1 Profilin-1 | IPI00216691 |
| RBMX Heterogeneous nuclear ribonucleoprotein G | IPI00304692 (+1) |
| RPS27A; UBC; UBB ubiquitin and ribosomal protein S27a precursor | IPI00179330 (+21) |
| S100A6 Protein S100-A6 | IPI00027463 |
| S100A7 Protein S100-A7 | IPI00219806 |
| S100A8 Protein S100-A8 | IPI00007047 |
| SH3BGRL SH3 domain-binding glutamic acidrich-like protein | IPI00025318 |
| SH3BGRL3 Putative uncharacterized protein | IPI00010402 (+2) |
| sp_B2MG_HUMAN | IPIsp_B2MG_HUMAN |
| TMSB10 Thymosin beta-10 | IPI00220827 |
| TXN Thioredoxin | IPI00216298 (+1) |
| TXNDC17 Thioredoxin domain-containing protein 17 | IPI00646689 |
| UFM1 Ubiquitin-fold modifier 1 precursor | IPI00010207 (+1) |
| KPRP Keratinocyte proline-rich protein | IPI00514908 |
| KRT1 Keratin, type II cytoskeletal 1 | IPI00220327 (+1) |
| KRT10 Keratin, type I cytoskeletal 10 | IPI00009865 |
| KRT14 Keratin, type I cytoskeletal 14 | IPI00384444 |
| KRT2 Keratin, type II cytoskeletal 2 epidermal | IPI00021304 (+1) |
| KRT5 Keratin, type II cytoskeletal 5 | IPI00009867 |
| KRT77 Keratin 77 | IPI00376379 |

TABLE 3-continued

Proteins identified by MS in glioma cell line SF-539:

| Protein: | Accession # |
| --- | --- |
| KRT9 Keratin, type I cytoskeletal 9 | IPI00019359 (+1) |
| sp_TRYP_PIG | IPIsp_TRYP_PIG |

TABLE 4

Proteins identified by MS from Glioma cell line U251 supernatants:

| Protein: | Accession # |
| --- | --- |
| A1BG Alpha-1B-glycoprotein precursor | IPI00022895 |
| A2M Alpha-2-macroglobulin precursor | IPI00478003 |
| C3 Complement C3 precursor (Fragment) | IPI00783987 |
| FGG Isoform Gamma-B of Fibrinogen gamma chain precursor | IPI00021891 (+3) |
| GLUD1 Glutamate dehydrogenase 1, mitochondrial precursor | IPI00016801 (+1) |
| HBA2; HBA1 Hemoglobin subunit alpha | IPI00410714 (+1) |
| HBB Hemoglobin subunit beta | IPI00654755 (+1) |
| HPX Hemopexin precursor | IPI00022488 |
| IGHG1 IGHG1 protein | IPI00448925 |
| IGHM IGHM protein | IPI00477090 |
| IGHV3OR16-13; IGHA1 IGHA1 protein | IPI00166866 (+1) |
| LDHB L-lactate dehydrogenase B chain | IPI00219217 |
| LOC100133739 Putative uncharacterized protein DKFZp686C15213 | IPI00426051 |
| LTF Growth-inhibiting protein 12 | IPI00298860 (+3) |
| MAGI1 Isoform 4 of Membrane-associated guanylate kinase, WW and PDZ domain-containing protein 1 | IPI00382692 |
| MPO Isoform H17 of Myeloperoxidase precursor | IPI00007244 (+2) |
| SERPINA1 Isoform 1 of Alpha-1-antitrypsin precursor | IPI00553177 (+1) |
| SERPINA3 Alpha-1-antichymotrypsin precursor | IPI00550991 (+1) |
| TF Serotransferrin precursor | IPI00022463 (+2) |
| ALB Isoform 1 of Serum albumin precursor | IPI00745872 (+1) |
| KRT1 Keratin, type II cytoskeletal 1 | IPI00220327 (+1) |
| KRT10 Keratin, type I cytoskeletal 10 | IPI00009865 (+1) |
| KRT14 Keratin, type I cytoskeletal 14 | IPI00384444 |
| KRT2 Keratin, type II cytoskeletal 2 epidermal | IPI00021304 (+1) |
| KRT5 Keratin, type II cytoskeletal 5 | IPI00009867 |
| KRT6C Keratin, type II cytoskeletal 6C | IPI00299145 |
| KRT9 Keratin, type I cytoskeletal 9 | IPI00019359 (+1) |
| sp_ALBU_BOVIN | IPIsp_ALBU_BOVIN |
| sp_TRYP_PIG | IPIsp_TRYP_PIG |

TABLE 5

Proteins identified by MS of supernatants from colon cell line HCC-2998:

| Protein: | Accession # |
| --- | --- |
| RPS27A; UBC; UBB ubiquitin and ribosomal protein S27a precursor | IPI00179330 |
| S100A6 Protein S100-A6 | IPI00027463 |
| S100A7 Protein S100-A7 | IPI00219806 |
| S100A8 Protein S100-A8 | IPI00007047 |
| S100A9 Protein S100-A9 | IPI00027462 |
| SERPINB3 Isoform 1 of Serpin B3 | IPI00022204 |
| KRT1 Keratin, type II cytoskeletal 1 | IPI00220327 |
| KRT10 Keratin, type I cytoskeletal 10 | IPI00009865 |
| KRT2 Keratin, type II cytoskeletal 2 epidermal | IPI00021304 |
| KRT9 Keratin, type I cytoskeletal 9 | IPI00019359 |
| sp_TRYP_PIG IPIsp_TRYP_PIG 24 kDa 14 | |

TABLE 6

Proteins identified by MS of supernatants from hepatic cell line HepG2:

| Protein: | Accession # |
| --- | --- |
| B2M Beta-2-microglobulin precursor | IPI00004656 |
| C19orf10 Uncharacterized protein C19orf10 precursor | IPI00056357 |
| CSTB Cystatin-B | IPI00021828 |
| CYCS Cytochrome c | IPI00465315 |
| HMGA1 Isoform HMG-I of High mobility group protein HMGI/HMG-Y | IPI00179700 |
| LGALS3 Galectin-3 | IPI00465431 |
| MIF Macrophage migration inhibitory factor | IPI00293276 |
| PFN1 Profilin-1 | IPI00216691 |
| PPIA; LOC654188; LOC653214 Peptidyl-prolyl cis-trans isomerase A | IPI00419585 |
| RNASE4 Ribonuclease 4 precursor | IPI00029699 |
| S100A6 Protein S100-A6 | IPI00027463 |
| UBC; RPS27A; UBB ubiquitin and ribosomal protein S27a precursor | IPI00179330 |
| KRT1 Keratin, type II cytoskeletal 1 | IPI00220327 |
| KRT10 Keratin, type I cytoskeletal 10 | IPI00009865 |
| KRT16 Keratin, type I cytoskeletal 16 | IPI00217963 |
| KRT2 Keratin, type II cytoskeletal 2 epidermal | IPI00021304 |
| KRT9 Keratin, type I cytoskeletal 9 | IPI00019359 |

TABLE 7

Proteins identified by MS of supernatants from ovarian cell line CRL-1978:
Proteins Identified by MS analysis of Chemorepellant Fractions of Cell Line CRL-1978

| Identified Proteins: | Accession # |
| --- | --- |
| ALB Serum albumin | IPI00022434 |
| B2M Beta-2-microgbulin precursor | IPI00004656 |
| C19orf10 Uncharacterized protein C19orf10 precursor | IPI00056357 |
| CST1 Cystatin-SN precursor | IPI00305477 |
| CST3 Cystatin-C precursor | IPI00032293 |
| CST4 Cystatin-S precursor | IPI00032294 |
| CYCS Cytochrome c | IPI00465315 |
| FAM3C Protein FAM3C precursor | IPI00021923 |
| ISG15 Interferon-induced 17 kDa protein precursor | IPI00375631 |
| KRT1 Keratin, type II cytoskeletal 1 | IPI00220327 |
| KRT10 Keratin, type I cytoskeletal 10 | IPI00009865 |
| KRT14 Keratin, type I cytoskeletal 14 | IPI00384444 |
| KRT2 Keratin, type II cytoskeletal 2 epidermal | IPI00021304 |
| KRT9 Keratin, type I cytoskeletal 9 | IPI00019359 |
| PFN1 Profilin-1 | IPI00216691 |
| PPIA; LOC654188; LOC653214 Peptidyl-prolyl cis-trans isomerase A | IPI00419585 |
| PPIB peptidylprolyl isomerase B precursor | IPI00646304 |
| S100A6 Protein S100-A6 | IPI00027463 |
| TXN Thioredoxin | IPI00216298 |
| UBC; RPS27A; UBB ubiquitin and ribosomal protein S27a precursor | IPI00179330 |

TABLE 8

Proteins identified by MS of supernatants from prostate cell line PC3 and ovarian cell line CRL-1978:
Proteins Identified by MS analysis of Chemorepellant Fractions of Cell Line PC3

| Identified Proteins: | Accession # |
|---|---|
| AGR2 AGR2 | IPI00007427 |
| ALB Serum albumin | IPI00022434 |
| ARMET ARMET protein precursor | IPI00328748 |
| C7orf24 Uncharacterized protein C7orf24 | IPI00031564 |
| COTL1 Coactosin-like protein | IPI00017704 |
| FAM3C Protein FAM3C precursor | IPI00021923 |
| HNRPA2B1 Isoform B1 of Heterogeneous nuclear ribonucleoproteins A2/B1 | IPI00396378 |
| HSPG2 Basement membrane-specific heparan sulfate proteoglycan core protein precursor | IPI00024284 |
| KRT1 Keratin, type II cytoskeletal 1 | IPI00220327 |
| KRT10 Keratin, type I cytoskeletal 10 | IPI00009865 |
| KRT14 Keratin, type I cytoskeletal 14 | IPI00384444 |
| KRT16 Keratin, type I cytoskeletal 16 | IPI00217963 |
| KRT2 Keratin, type II cytoskeletal 2 epidermal | IPI00021304 |
| KRT5 Keratin, type II cytoskeletal 5 | IPI00009867 |
| KRT6A Keratin, type II cytoskeletal 6A | IPI00300725 |
| KRT9 Keratin, type I cytoskeletal 9 | IPI00019359 |
| LCN2 Neutrophil gelatinase-associated lipocalin precursor | IPI00299547 |
| LMNA Isoform A of Lamin-A/C | IPI00021405 |
| NME1; NME1-NME2; NME2 NME1-NME2 protein | IPI00795292 |
| NPC2 Epididymal secretory protein E1 precursor | IPI00301579 |
| PARK7 Protein DJ-1 | IPI00298547 |
| PEBP1 Phosphatidylethanolamine-binding protein 1 | IPI00219446 |
| PPIA; LOC654188; LOC653214 Peptidyl-prolyl cis-trans isomerase A | IPI00419585 |
| PPIB peptidylprolyl isomerase B precursor | IPI00646304 |
| PRDX1 Peroxiredoxin-1 | IPI00000874 |
| PRDX6 Peroxiredoxin-6 | IPI00220301 |
| RBP4 Plasma retinol-binding protein precursor | IPI00022420 |
| TAGLN2 Transgelin-2 | IPI00550363 |
| TFF2 Trefoil factor 2 precursor | IPI00010675 |
| TIMP2 Metalloproteinase inhibitor 2 precursor | IPI00027166 |
| TPT1 Tumor protein, translationally-controlled 1 | IPI00009943 |

TABLE 9

Proteins identified by MS of supernatants from breast cancer cell line SK-BR-3:

| Protein: | Accession # |
|---|---|
| TRFE__HU Serotransferrin precursor (Transferrin) (Siderophilin) | P02787 |
| EF1G__HU Elongation factor 1-gamma (EF-1-gamma) | P26641 |
| LG3BP__HU galectin 3 binding protein precursor (Lectin galactoside-binding soluble 3-binding protein) | Q08380 |

As shown in the figures, the following proteins were identified in chemorepulsive fractions of supernatants from cell lines and/or ovarian cystic fluid were shown to induce negative chemotaxis of neutrophils:

actin, 14-3-3 zeta/delta, apolipoprotein A1, hemopexin, PARK7, cofilin-1, 14-3-3 epsilon, 14-3-3-gamma, phosphoserine phosphatase, superoxide dismutase, profilin-1, beta-2 microglobulin, cytochrome c, cystatin B, macrophage migration inhibitory factor (MIF), FK506 binding protein, thioredoxin, galectin 3, human transferrin, human EF-1-gamma and human galectin 3 binding protein.

Profilin-1 was identified in chemorepulsive supernatant fractions. As shown in the figures, profilin-2 was shown to induce negative chemotaxis.

Example 3

Chemorepellant Proteins Identified in Multiple Chemorepellant Fractions

Table 10 shows chemorepellant proteins that were isolated from chemorepellant fractions of at least two cells or from a cell line and ovarian cystic fluid (as indicated by an "X") and were shown to induce chemorepulsion of neutrophils in their purified form (as described in Examples 1 and 2). For example, Actin was identified in the chemorepulsive fractions isolated from the supernatant of SF-539 cells and from ovarian cystic fluid sample (described in Example 1).

TABLE 10

Proteins identified in the chemorepellant fractions of at least two cell lines

| Proteins isolated from supernatants | CRL-1978 | PC-3 | SF-539 | HepG2 | 786-O | ACHN | OCI-856 |
|---|---|---|---|---|---|---|---|
| ACTA2 (Actin, aortic smooth muscle) | | | X | | | | X |
| B2M (beta-2 microglobulin precursor) | X | | X | X | | | |
| CFL1 (Cofilin-1) | | | | | X | X | |
| CSTB (cystatin B) | | | X | X | | | |
| CYCS (cytochrome C) | X | | X | X | | | |
| LGAL3 (galectin-3) | | | X | X | | | |
| MIF (macrophage migration inhibitory factor) | | | X | X | | | |
| PARK7 Protein DJ-1 | | X | | | X | X | |
| PSPH (phosphoserine phosphatase) | | | | | X | X | |
| SOD1 (superoxide dismutase | | | | | X | X | |
| TXN (thioredoxin) | X | | X | | | | |
| YWHAE 14-3-3 epsilon | | | | | X | X | |
| YWHAZ (14-3-3 zeta/delta) | | | | | X | X | X |

Table 11 lists proteins identified in chemorepellant fractions of at least two cell lines or at least one cell line and ovarian cyst fluid.

TABLE 11A

Proteins identified in chemorepellant fractions of at least two cell lines or ovarian cystic fluid and at least one cell line

| Protein Name | CRL-1978 | PC-3 | SF-539 | HepG2 | SK-BR-3 | HCC-2998 | 786-O | ACHN | U-251 | OCI-856 (Cyst Fluid) |
|---|---|---|---|---|---|---|---|---|---|---|
| ACBD3 Golgi resident protein GCP60 | | | | | | | X | X | | |

TABLE 11A-continued

Proteins identified in chemorepellant fractions of at least two cell lines or ovarian cystic fluid and at least one cell line

| Protein Name | CRL-1978 | PC-3 | SF-539 | HepG2 | SK-BR-3 | HCC-2998 | 786-O | ACHN | U-251 | OCI-856 (Cyst Fluid) |
|---|---|---|---|---|---|---|---|---|---|---|
| APOA1BP Isoform 1 of Apolipoprotein A-I-binding protein precursor | | | | | | | X | X | | |
| ARHGDIA Rho GDP-dissociation inhibitor 1 | | | | | | | X | X | | |
| ARMET ARMET protein precursor | | X | | | | | X | X | | |
| C19orf10 Uncharacterized protein C19orf10 precursor | X | | X | X | | | | | | |
| C19orf33 Isoform 1 of Immortalization up-regulated protein | | | | | | | X | X | | |
| C1orf128 Isoform 1 of UPF0424 protein C1orf128 | | | | | | | X | X | | |
| C7orf24 Uncharacterized protein C7orf24 | | X | | | | | X | | | |
| CALD1 Isoform 4 of Caldesmon | | | | | | | X | X | | |
| CALM2; CALM1; CALM3 Calmodulin | | | | | | | X | X | | |
| CFL1 Cofilin-1 | | | | | | | X | X | | |
| CFL2 Cofilin-2 | | | | | | | X | X | | |
| CIAPIN1 Isoform 3 of Anamorsin | | | | | | | X | X | | |
| CNPY2 Isoform 1 of Protein canopy homolog 2 precursor | | | | | | | X | X | | |
| COTL1 Coactosin-like protein | | X | X | | | | | | | |
| CRK v-crk sarcoma virus CT10 oncogene homolog isoform b | | | | | | | X | X | | |
| CSTB Cystatin-B | | | X | X | | | | | | |
| CYCS Cytochrome c | X | | X | X | | | | | | |
| CYR61 CYR61 protein | | | | | | | X | X | | |
| DSTN Destrin | | | | | | | X | X | | |
| DTD1 D-tyrosyl-tRNA(Tyr) deacylase 1 | | | | | | | X | X | | |
| EEF1G Elongation factor 1-gamma | | | | | | X | X | X | | |
| EIF4B Eukaryotic translation initiation factor 4B | | | | | | | X | X | | |
| EIF6 Eukaryotic translation initiation factor 6 | | | | | | | X | X | | |
| FAHD1 Isoform 2 of Fumarylacetoacetate hydrolase domain-containing protein 1 | | | | | | | X | X | | |
| FAM3C Protein FAM3C precursor | X | X | | | | | X | | | |
| FER1L3 Isoform 1 of Myoferlin | | | | | | | X | X | | |
| GLO1 Lactoylglutathione lyase | | | | | | | X | X | | |
| GSTP1 Glutathione S-transferase P | | | | | | | X | X | | |
| HDDC2 Isoform 2 of HD domain-containing protein 2 | | | | | | | X | X | | |
| HMGA1 Isoform HMG-I of High mobility group protein HMGI/HMG-Y | | | | X | | | | X | | |

TABLE 11A-continued

Proteins identified in chemorepellant fractions of at least two cell lines or ovarian cystic fluid and at least one cell line

| Protein Name | CRL-1978 | PC-3 | SF-539 | HepG2 | SK-BR-3 | HCC-2998 | 786-O | ACHN | U-251 | OCI-856 (Cyst Fluid) |
|---|---|---|---|---|---|---|---|---|---|---|
| HMGN1 Non-histone chromosomal protein HMG-14 | | | | | | | X | X | | |
| HN1 Isoform 1 of Hematological and neurological expressed 1 protein | | | | | | | X | X | | |
| HNRNPA2B1 Isoform B1 of Heterogeneous nuclear ribonucleoproteins A2/B1 | | X | | | | | X | | | |
| HPRT1 Hypoxanthine-guanine phosphoribosyltransferase | | | | | | | X | X | | |
| ISG15 Interferon-induced 17 kDa protein precursor | X | | X | | | | | | | |
| KIAA0174 Isoform 1 of Uncharacterized protein KIAA0174 | | | | | | | X | X | | |
| LDHB L-lactate dehydrogenase B chain | | | | | | | | X | X | |
| LGALS3 Galectin-3 | | | X | X | | | | | | |
| LMNA Isoform A of Lamin-A/C | | X | | | | | X | | | |
| M6PRBP1 Isoform A of Mannose-6-phosphate receptor-binding protein 1 | | | | | | | X | X | | |
| MAPRE1 Microtubule-associated protein RP/EB family member 1 | | | | | | | X | X | | |
| NME2 Nucleoside diphosphate kinase | | | | | | | X | X | | |
| NPC2 Epididymal secretory protein E1 precursor | | X | | | | | X | X | | |
| NQO2 Ribosyldihydronicotinamide dehydrogenase | | | | | | | X | X | | |
| NUDT1 Isoform p26 of 7,8-dihydro-8-oxoguanine triphosphatase | | | | | | | X | X | | |
| PDAP1 28 kDa heat- and acid-stable phosphoprotein | | | | | | | X | X | | |
| PEBP1 Phosphatidylethanolamine-binding protein 1 | | X | | | | | X | | | |
| PFN1 Profilin-1 | X | | X | X | | | | | | |
| PPIA; LOC654188; LOC653214 Peptidyl-prolyl cis-trans isomerase A | X | X | | X | | | | X | | |
| PPIB peptidylprolyl isomerase B precursor | X | X | | | | | X | X | | |
| PPIF Peptidyl-prolyl cis-trans isomerase, mitochondrial precursor | | | | | | | X | X | | |
| PRDX1 Peroxiredoxin-1 | | X | | | | | X | X | | |
| PRDX3 Thioredoxin-dependent peroxide reductase, | | | | | | | X | X | | |

TABLE 11A-continued

Proteins identified in chemorepellant fractions of at least two cell lines or ovarian cystic fluid and at least one cell line

| Protein Name | CRL-1978 | PC-3 | SF-539 | HepG2 | SK-BR-3 | HCC-2998 | 786-O | ACHN | U-251 | OCI-856 (Cyst Fluid) |
|---|---|---|---|---|---|---|---|---|---|---|
| mitochondrial precursor | | | | | | | | | | |
| PRDX6 Peroxiredoxin-6 | | X | | | | | | X | | |
| QDPR Dihydropteridine reductase | | | | | | | X | X | | |
| RAB11B Ras-related protein Rab-11B | | | | | | | X | X | | |
| REXO2 Isoform 1 of Oligoribonuclease, mitochondrial precursor (Fragment) | | | | | | | X | X | | |
| RNASET2 Isoform 1 of Ribonuclease T2 precursor | | | | | | | X | X | | |
| RPE Isoform 1 of Ribulose-phosphate 3-epimerase | | | | | | | X | X | | |
| RPIA Ribose-5-phosphate isomerase | | | | | | | X | X | | |
| RPS27A; UBC; UBB ubiquitin and ribosomal protein S27a precursor | | | X | | | X | | | | |
| S100A11 Protein S100-A11 | | | | | | | X | X | | |
| S100A6 Protein S100-A6 | X | | X | X | | X | X | | | |
| S100A7 Protein S100-A7 | | | X | | | X | | | | |
| S100A8 Protein S100-A8 | | | X | | | X | | | | |
| SCYE1 Multisynthetase complex auxiliary component p43 | | | | | | | X | X | | |
| SNX12 Isoform 1 of Sorting nexin-12 | | | | | | | X | X | | |
| STX7 Isoform 1 of Syntaxin-7 | | | | | | | X | X | | |
| SUB1 Activated RNA polymerase II transcriptional coactivator p15 | | | | | | | X | X | | |
| TAGLN2 Transgelin-2 | | X | | | | | X | | | |
| TPI1 Isoform 1 of Triosephosphate isomerase | | | | | | | X | X | | |
| TPK1 Thiamin pyrophosphokinase 1 | | | | | | | X | X | | |
| TPT1 Translationally-controlled tumor protein | | | | | | | X | X | | |
| TRFE Human Serotransferrin precursor (Transferrin) (Siderophilin) | | | | | X | | | | X | X |
| TWF1 Isoform 3 of Twinfilin-1 | | | | | | | X | X | | |
| TXNDC12 Thioredoxin domain-containing protein 12 precursor | | | | | | | X | X | | |
| UBC; RPS27A; UBB ubiquitin and ribosomal protein S27a precursor | X | | | X | | | | | | |
| UBE2I SUMO-conjugating enzyme UBC9 | | | | | | | X | X | | |

TABLE 11A-continued

Proteins identified in chemorepellant fractions of at least two cell lines or ovarian cystic fluid and at least one cell line

| Protein Name | CRL-1978 | PC-3 | SF-539 | HepG2 | SK-BR-3 | HCC-2998 | 786-O | ACHN | U-251 | OCI-856 (Cyst Fluid) |
|---|---|---|---|---|---|---|---|---|---|---|
| UBE2L3 Ubiquitin-conjugating enzyme E2 L3 | | | | | | | X | X | | |
| UCHL1 Ubiquitin carboxyl-terminal hydrolase isozyme L1 | | | | | | | X | X | | |
| VAPA Vesicle-associated membrane protein-associated protein A | | | | | | | X | X | | |
| YWHAB Isoform Short of 14-3-3 protein beta/alpha | | | | | | | X | X | | |
| YWHAE 14-3-3 protein epsilon | | | | | | | X | X | | |
| YWHAZ 14-3-3 protein zeta/delta | | | | | | | X | X | | X |

TABLE 11B

Accession numbers for proteins listed in Table 11A

| Accession # | Protein Name |
|---|---|
| IPI00009315 | ACBD3 Golgi resident protein GCP60 |
| IPI00168479 (+1) | APOA1BP Isoform 1 of Apolipoprotein A-I-binding protein precursor |
| IPI00003815 (+1) | ARHGDIA Rho GDP-dissociation inhibitor 1 |
| IPI00328748 | ARMET ARMET protein precursor |
| IPI00056357 | C19orf10 Uncharacterized protein C19orf10 precursor |
| IPI00030767 | C19orf33 Isoform 1 of Immortalization up-regulated protein |
| IPI00015351 | C1orf128 Isoform 1 of UPF0424 protein C1orf128 |
| IPI00031564 | C7orf24 Uncharacterized protein C7orf24 |
| IPI00218696 | CALD1 Isoform 4 of Caldesmon |
| IPI00075248 (+2) | CALM2; CALM1; CALM3 Calmodulin |
| IPI00012011 | CFL1 Cofilin-1 |
| IPI00413344 | CFL2 Cofilin-2 |
| IPI00025333 (+1) | CIAPIN1 Isoform 3 of Anamorsin |
| IPI00443909 | CNPY2 Isoform 1 of Protein canopy homolog 2 precursor |
| IPI00017704 | COTL1 Coactosin-like protein |
| IPI00305469 | CRK v-crk sarcoma virus CT10 oncogene homolog isoform b |
| IPI00021828 | CSTB Cystatin-B |
| IPI00465315 | CYCS Cytochrome c |
| IPI00006273 (+2) | CYR61 CYR61 protein |
| IPI00473014 | DSTN Destrin |
| IPI00152692 | DTD1 D-tyrosyl-tRNA(Tyr) deacylase 1 |
| IPI00000875 (+1) | EEF1G Elongation factor 1-gamma |
| IPI00012079 (+1) | EIF4B Eukaryotic translation initiation factor 4B |
| IPI00010105 | EIF6 Eukaryotic translation initiation factor 6 |
| IPI00440828 (+2) | FAHD1 Isoform 2 of Fumarylacetoacetate hydrolase domain-containing protein 1 |
| IPI00021923 | FAM3C Protein FAM3C precursor |
| IPI00021048 (+5) | FER1L3 Isoform 1 of Myoferlin |
| IPI00220766 | GLO1 Lactoylglutathione lyase |
| IPI00219757 (+1) | GSTP1 Glutathione S-transferase P |
| IPI00386751 (+1) | HDDC2 Isoform 2 of HD domain-containing protein 2 |
| IPI00179700 | HMGA1 Isoform HMG-I of High mobility group protein HMGI/HMG-Y |
| IPI00554761 | HMGN1 Non-histone chromosomal protein HMG-14 |
| IPI00007764 (+1) | HN1 Isoform 1 of Hematological and neurological expressed 1 protein |
| IPI00396378 | HNRNPA2B1 Isoform B1 of Heterogeneous nuclear ribonucleoproteins A2/B1 |
| IPI00218493 | HPRT1 Hypoxanthine-guanine phosphoribosyltransferase |
| IPI00375631 | ISG15 Interferon-induced 17 kDa protein precursor |
| IPI00024660 (+2) | KIAA0174 Isoform 1 of Uncharacterized protein KIAA0174 |
| IPI00219217 | LDHB L-lactate dehydrogenase B chain |
| IPI00465431 | LGALS3 Galectin-3 |
| IPI00021405 (+4) | LMNA Isoform A of Lamin-A/C |
| IPI00106668 (+1) | M6PRBP1 Isoform A of Mannose-6-phosphate receptor-binding protein 1 |
| IPI00017596 | MAPRE1 Microtubule-associated protein RP/EB family member 1 |
| IPI00604590 (+1) | NME2 Nucleoside diphosphate kinase |
| IPI00301579 | NPC2 Epididymal secretory protein E1 precursor |
| IPI00219129 (+3) | NQO2 Ribosyldihydronicotinamide dehydrogenase |
| IPI00004392 (+4) | NUDT1 Isoform p26 of 7,8-dihydro-8-oxoguanine triphosphatase |
| IPI00013297 | PDAP1 28 kDa heat- and acid-stable phosphoprotein |
| IPI00219446 | PEBP1 Phosphatidylethanolamine-binding protein 1 |
| IPI00216691 | PFN1 Profilin-1 |
| IPI00419585 | PPIA; LOC654188; LOC653214 Peptidyl-prolyl cis-trans isomerase A |
| IPI00646304 | PPIB peptidylprolyl isomerase B precursor |
| IPI00026519 | PPIF Peptidyl-prolyl cis-trans isomerase, mitochondrial precursor |
| IPI00000874 (+1) | PRDX1 Peroxiredoxin-1 |
| IPI00024919 (+1) | PRDX3 Thioredoxin-dependent peroxide reductase, mitochondrial precursor |
| IPI00220301 | PRDX6 Peroxiredoxin-6 |
| IPI00014439 | QDPR Dihydropteridine reductase |
| IPI00020436 (+2) | RAB11B Ras-related protein Rab-11B |

TABLE 11B-continued

Accession numbers for proteins listed in Table 11A

| Accession # | Protein Name |
|---|---|
| IPI00032830 (+1) | REXO2 Isoform 1 of Oligoribonuclease, mitochondrial precursor (Fragment) |
| IPI00414896 (+1) | RNASET2 Isoform 1 of Ribonuclease T2 precursor |
| IPI00335280 (+1) | RPE Isoform 1 of Ribulose-phosphate 3-epimerase |
| IPI00026513 (+1) | RPIA Ribose-5-phosphate isomerase |
| IPI00179330 | RPS27A; UBC; UBB ubiquitin and ribosomal protein S27a precursor |
| IPI00013895 | S100A11 Protein S100-A11 |
| IPI00027463 | S100A6 Protein S100-A6 |
| IPI00219806 | S100A7 Protein S100-A7 |
| IPI00007047 | S100A8 Protein S100-A8 |
| IPI00006252 (+1) | SCYE1 Multisynthetase complex auxiliary component p43 |
| IPI00438170 (+2) | SNX12 Isoform 1 of Sorting nexin-12 |
| IPI00289876 (+1) | STX7 Isoform 1 of Syntaxin-7 |
| IPI00221222 | SUB1 Activated RNA polymerase II transcriptional coactivator p15 |
| IPI00550363 | TAGLN2 Transgelin-2 |
| IPI00465028 | TPI1 Isoform 1 of Triosephosphate isomerase |
| IPI00072523 (+1) | TPK1 Thiamin pyrophosphokinase 1 |
| IPI00550900 | TPT1 Translationally-controlled tumor protein |
| IPI00022463 (+2) | TRFE Human Serotransferrin precursor (Transferrin) (Siderophilin) |
| IPI00815767 | TWF1 Isoform 3 of Twinfilin-1 |
| IPI00026328 | TXNDC12 Thioredoxin domain-containing protein 12 precursor |
| IPI00179330 | UBC; RPS27A; UBB ubiquitin and ribosomal protein S27a precursor |
| IPI00032957 (+2) | UBE2I SUMO-conjugating enzyme UBC9 |
| IPI00021347 | UBE2L3 Ubiquitin-conjugating enzyme E2 L3 |
| IPI00018352 | UCHL1 Ubiquitin carboxyl-terminal hydrolase isozyme L1 |
| IPI00170692 (+1) | VAPA Vesicle-associated membrane protein-associated protein A |
| IPI00759832 | YWHAB Isoform Short of 14-3-3 protein beta/alpha |
| IPI00000816 | YWHAE 14-3-3 protein epsilon |
| IPI00021263 | YWHAZ 14-3-3 protein zeta/delta |

While this invention has been particularly shown and described with references to preferred embodiments thereof, it will be understood by those skilled in the art that various changes in form and details may be made therein without departing from the scope of the invention encompassed by the appended claims.

---

SEQUENCE LISTING

```
<160> NUMBER OF SEQ ID NOS: 21

<210> SEQ ID NO 1
<211> LENGTH: 375
<212> TYPE: PRT
<213> ORGANISM: Homo Sapiens

<400> SEQUENCE: 1

Met Asp Asp Asp Ile Ala Ala Leu Val Val Asp Asn Gly Ser Gly Met
1               5                   10                  15

Cys Lys Ala Gly Phe Ala Gly Asp Asp Ala Pro Arg Ala Val Phe Pro
            20                  25                  30

Ser Ile Val Gly Arg Pro Arg His Gln Gly Val Met Val Gly Met Gly
        35                  40                  45

Gln Lys Asp Ser Tyr Val Gly Asp Glu Ala Gln Ser Lys Arg Gly Ile
    50                  55                  60

Leu Thr Leu Lys Tyr Pro Ile Glu His Gly Ile Val Thr Asn Trp Asp
65                  70                  75                  80

Asp Met Glu Lys Ile Trp His His Thr Phe Tyr Asn Glu Leu Arg Val
                85                  90                  95

Ala Pro Glu Glu His Pro Val Leu Leu Thr Glu Ala Pro Leu Asn Pro
            100                 105                 110

Lys Ala Asn Arg Glu Lys Met Thr Gln Ile Met Phe Glu Thr Phe Asn
        115                 120                 125

Thr Pro Ala Met Tyr Val Ala Ile Gln Ala Val Leu Ser Leu Tyr Ala
    130                 135                 140

Ser Gly Arg Thr Thr Gly Ile Val Met Asp Ser Gly Asp Gly Val Thr
145                 150                 155                 160

His Thr Val Pro Ile Tyr Glu Gly Tyr Ala Leu Pro His Ala Ile Leu
                165                 170                 175
```

```
Arg Leu Asp Leu Ala Gly Arg Asp Leu Thr Asp Tyr Leu Met Lys Ile
            180                 185                 190

Leu Thr Glu Arg Gly Tyr Ser Phe Thr Thr Thr Ala Glu Arg Glu Ile
        195                 200                 205

Val Arg Asp Ile Lys Glu Lys Leu Cys Tyr Val Ala Leu Asp Phe Glu
    210                 215                 220

Gln Glu Met Ala Thr Ala Ala Ser Ser Ser Leu Glu Lys Ser Tyr
225                 230                 235                 240

Glu Leu Pro Asp Gly Gln Val Ile Thr Ile Gly Asn Glu Arg Phe Arg
                245                 250                 255

Cys Pro Glu Ala Leu Phe Gln Pro Ser Phe Leu Gly Met Glu Ser Cys
            260                 265                 270

Gly Ile His Glu Thr Thr Phe Asn Ser Ile Met Lys Cys Asp Val Asp
        275                 280                 285

Ile Arg Lys Asp Leu Tyr Ala Asn Thr Val Leu Ser Gly Gly Thr Thr
    290                 295                 300

Met Tyr Pro Gly Ile Ala Asp Arg Met Gln Lys Glu Ile Thr Ala Leu
305                 310                 315                 320

Ala Pro Ser Thr Met Lys Ile Lys Ile Ile Ala Pro Pro Glu Arg Lys
                325                 330                 335

Tyr Ser Val Trp Ile Gly Gly Ser Ile Leu Ala Ser Leu Ser Thr Phe
            340                 345                 350

Gln Gln Met Trp Ile Ser Lys Gln Glu Tyr Asp Glu Ser Gly Pro Ser
        355                 360                 365

Ile Val His Arg Lys Cys Phe
    370                 375

<210> SEQ ID NO 2
<211> LENGTH: 272
<212> TYPE: PRT
<213> ORGANISM: Homo Sapiens

<400> SEQUENCE: 2

Met Asp Lys Asn Glu Leu Val Gln Lys Ala Lys Leu Ala Glu Gln Ala
1               5                   10                  15

Glu Arg Tyr Asp Asp Met Ala Ala Cys Met Lys Ser Val Thr Glu Gln
            20                  25                  30

Gly Ala Glu Leu Ser Asn Glu Glu Arg Asn Leu Leu Ser Val Ala Tyr
        35                  40                  45

Lys Asn Val Val Gly Ala Arg Arg Ser Ser Trp Arg Val Val Ser Ser
50                  55                  60

Ile Glu Gln Lys Thr Glu Gly Ala Glu Lys Lys Gln Gln Met Ala Arg
65                  70                  75                  80

Glu Tyr Arg Glu Lys Ile Glu Thr Glu Leu Arg Asp Ile Cys Asn Asp
                85                  90                  95

Val Leu Ser Leu Leu Glu Lys Phe Leu Ile Pro Asn Ala Ser Gln Ala
            100                 105                 110

Glu Ser Lys Val Phe Tyr Leu Lys Met Lys Gly Asp Tyr Tyr Arg Tyr
        115                 120                 125

Leu Ala Glu Val Ala Ala Gly Asp Asp Lys Lys Gly Ile Val Asp Gln
    130                 135                 140

Ser Gln Gln Ala Tyr Gln Glu Ala Phe Glu Ile Ser Lys Lys Glu Met
145                 150                 155                 160

Gln Pro Thr His Pro Ile Arg Leu Gly Leu Ala Leu Asn Phe Ser Val
                165                 170                 175
```

```
Phe Tyr Tyr Glu Ile Leu Asn Ser Pro Glu Lys Ala Cys Ser Leu Ala
            180                 185                 190

Lys Thr Ala Phe Asp Glu Ala Ile Ala Glu Leu Asp Thr Leu Ser Glu
        195                 200                 205

Glu Ser Tyr Lys Asp Ser Thr Leu Ile Met Gln Leu Leu Arg Asp Asn
    210                 215                 220

Leu Thr Leu Trp Thr Ser Asp Thr Gln Gly Asp Glu Ala Glu Ala Gly
225                 230                 235                 240

Glu Gly Gly Glu Asn Gly Leu Leu Pro Val Leu Glu Ser Phe Lys Val
                245                 250                 255

Ser Phe Leu Ser Ala Leu Glu Glu Tyr Thr Lys Lys Leu Asn Thr Gln
            260                 265                 270

<210> SEQ ID NO 3
<211> LENGTH: 240
<212> TYPE: PRT
<213> ORGANISM: Homo Sapiens

<400> SEQUENCE: 3

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

<210> SEQ ID NO 4
<211> LENGTH: 461
<212> TYPE: PRT
<213> ORGANISM: Homo Sapiens

<400> SEQUENCE: 4

Met Ala Arg Val Leu Gly Ala Pro Val Ala Leu Gly Leu Trp Ser Leu
```

-continued

```
               1               5              10              15
Cys Trp Ser Leu Ala Ile Ala Thr Pro Leu Pro Thr Ser Ala His
                20                  25                  30

Gly Asn Val Ala Glu Gly Glu Thr Lys Pro Asp Pro Asp Val Thr Glu
                35                  40                  45

Arg Cys Ser Asp Gly Trp Ser Phe Asp Ala Thr Thr Leu Asp Asp Asn
 50                  55                  60

Gly Thr Met Leu Phe Phe Lys Gly Glu Phe Val Trp Lys Ser His Lys
 65                  70                  75                  80

Trp Asp Arg Glu Leu Ile Ser Glu Arg Trp Lys Asn Phe Pro Ser Pro
                85                  90                  95

Val Asp Ala Ala Phe Arg Gln Gly His Asn Ser Val Phe Leu Ile Lys
                100                 105                 110

Gly Asp Lys Val Trp Val Tyr Pro Pro Glu Lys Lys Glu Lys Gly Tyr
                115                 120                 125

Pro Leu Leu Gln Asp Glu Phe Pro Gly Ile Pro Ser Pro Leu Asp Ala
                130                 135                 140

Ala Val Glu Cys His Arg Gly Glu Cys Gln Ala Glu Gly Val Leu Phe
145                 150                 155                 160

Phe Gln Gly Asp Arg Glu Trp Phe Trp Asp Leu Ala Thr Gly Thr Met
                165                 170                 175

Lys Glu Arg Ser Trp Pro Ala Val Gly Asn Cys Ser Ser Ala Leu Arg
                180                 185                 190

Trp Leu Gly Arg Tyr Tyr Cys Phe Gln Gly Asn Gln Phe Leu Arg Phe
                195                 200                 205

Asp Pro Val Arg Gly Glu Val Pro Pro Arg Tyr Pro Arg Asp Val Arg
                210                 215                 220

Asp Tyr Phe Met Pro Cys Pro Gly Arg Gly His Gly His Arg Asn Gly
225                 230                 235                 240

Thr Gly His Gly Asn Ser Thr His His Gly Pro Glu Tyr Met Arg Cys
                245                 250                 255

Ser Pro His Leu Val Leu Ser Ala Leu Thr Ser Asp Asn His Gly Ala
                260                 265                 270

Thr Tyr Ala Phe Ser Gly Thr His Tyr Trp Arg Leu Asp Thr Ser Arg
                275                 280                 285

Asp Gly Trp His Ser Trp Pro Ile Ala His Gln Trp Pro Gln Gly Pro
                290                 295                 300

Ser Ala Val Asp Ala Ala Phe Ser Trp Glu Glu Lys Leu Tyr Leu Val
305                 310                 315                 320

Gln Gly Thr Gln Val Tyr Val Phe Leu Thr Lys Gly Gly Tyr Thr Leu
                325                 330                 335

Val Ser Gly Tyr Pro Lys Arg Leu Glu Lys Glu Val Gly Thr Pro His
                340                 345                 350

Gly Ile Ile Leu Asp Ser Val Asp Ala Ala Phe Ile Cys Pro Gly Ser
                355                 360                 365

Ser Arg Leu His Ile Met Ala Gly Arg Arg Leu Trp Trp Leu Asp Leu
                370                 375                 380

Lys Ser Gly Ala Gln Ala Thr Trp Thr Glu Leu Pro Trp Pro His Glu
385                 390                 395                 400

Lys Val Asp Gly Ala Leu Cys Met Glu Lys Ser Leu Gly Pro Asn Ser
                405                 410                 415

Cys Ser Ala Asn Gly Pro Gly Leu Tyr Leu Ile His Gly Pro Asn Leu
                420                 425                 430
```

```
Tyr Cys Tyr Ser Asp Val Glu Lys Leu Asn Ala Ala Lys Ala Leu Pro
        435                 440                 445

Gln Pro Gln Asn Val Thr Ser Leu Leu Gly Cys Thr His
    450                 455                 460

<210> SEQ ID NO 5
<211> LENGTH: 188
<212> TYPE: PRT
<213> ORGANISM: Homo Sapiens

<400> SEQUENCE: 5

Met Ala Ser Lys Arg Ala Leu Val Ile Leu Ala Lys Gly Ala Glu Glu
1               5                   10                  15

Met Glu Thr Ile Pro Val Asp Val Met Arg Arg Ala Gly Ile Lys Val
            20                  25                  30

Thr Val Ala Gly Leu Ala Gly Lys Asp Pro Val Gln Cys Ser Arg Asp
        35                  40                  45

Val Val Ile Cys Pro Asp Ala Ser Leu Glu Asp Ala Lys Lys Glu Gly
    50                  55                  60

Pro Tyr Asp Val Val Leu Pro Gly Gly Asn Leu Gly Ala Gln Asn
65                  70                  75                  80

Leu Ser Glu Ser Ala Ala Val Lys Glu Ile Leu Lys Glu Gln Glu Asn
                85                  90                  95

Arg Lys Gly Leu Ile Ala Ala Ile Cys Ala Gly Pro Thr Ala Leu Leu
            100                 105                 110

Ala His Glu Ile Gly Phe Gly Ser Lys Val Thr Thr His Pro Leu Ala
        115                 120                 125

Lys Asp Lys Met Met Asn Gly Gly His Tyr Thr Tyr Ser Glu Asn Arg
    130                 135                 140

Val Glu Lys Asp Gly Leu Ile Leu Thr Ser Arg Gly Pro Gly Thr Ser
145                 150                 155                 160

Phe Glu Phe Ala Leu Ala Ile Val Glu Ala Leu Asn Gly Lys Glu Val
                165                 170                 175

Ala Ala Gln Val Lys Ala Pro Leu Val Leu Lys Asp
            180                 185

<210> SEQ ID NO 6
<211> LENGTH: 166
<212> TYPE: PRT
<213> ORGANISM: Homo Sapiens

<400> SEQUENCE: 6

Met Ala Ser Gly Val Ala Val Ser Asp Gly Val Ile Lys Val Phe Asn
1               5                   10                  15

Asp Met Lys Val Arg Lys Ser Ser Thr Pro Glu Glu Val Lys Lys Arg
            20                  25                  30

Lys Lys Ala Val Leu Phe Cys Leu Ser Glu Asp Lys Lys Asn Ile Ile
        35                  40                  45

Leu Glu Glu Gly Lys Glu Ile Leu Val Gly Asp Val Gly Gln Thr Val
    50                  55                  60

Asp Asp Pro Tyr Ala Thr Phe Val Lys Met Leu Pro Asp Lys Asp Cys
65                  70                  75                  80

Arg Tyr Ala Leu Tyr Asp Ala Thr Tyr Glu Thr Lys Glu Ser Lys Lys
                85                  90                  95

Glu Asp Leu Val Phe Ile Phe Trp Ala Pro Glu Ser Ala Pro Leu Lys
            100                 105                 110

Ser Lys Met Ile Tyr Ala Ser Ser Lys Asp Ala Ile Lys Lys Lys Leu
```

```
            115                 120                 125
Thr Gly Ile Lys His Glu Leu Gln Ala Asn Cys Tyr Glu Glu Val Lys
            130                 135                 140
Asp Arg Cys Thr Leu Ala Glu Lys Leu Gly Gly Ser Ala Val Ile Ser
145                 150                 155                 160
Leu Glu Gly Lys Pro Leu
                165

<210> SEQ ID NO 7
<211> LENGTH: 255
<212> TYPE: PRT
<213> ORGANISM: Homo Sapiens

<400> SEQUENCE: 7

Met Asp Asp Arg Glu Asp Leu Val Tyr Gln Ala Lys Leu Ala Glu Gln
1               5                   10                  15

Ala Glu Arg Tyr Asp Glu Met Val Glu Ser Met Lys Lys Val Ala Gly
                20                  25                  30

Met Asp Val Glu Leu Thr Val Glu Glu Arg Asn Leu Leu Ser Val Ala
            35                  40                  45

Tyr Lys Asn Val Ile Gly Ala Arg Arg Ala Ser Trp Arg Ile Ile Ser
50                  55                  60

Ser Ile Glu Gln Lys Glu Glu Asn Lys Gly Gly Glu Asp Lys Leu Lys
65                  70                  75                  80

Met Ile Arg Glu Tyr Arg Gln Met Val Glu Thr Glu Leu Lys Leu Ile
                85                  90                  95

Cys Cys Asp Ile Leu Asp Val Leu Asp Lys His Leu Ile Pro Ala Ala
            100                 105                 110

Asn Thr Gly Glu Ser Lys Val Phe Tyr Tyr Lys Met Lys Gly Asp Tyr
        115                 120                 125

His Arg Tyr Leu Ala Glu Phe Ala Thr Gly Asn Asp Arg Lys Glu Ala
    130                 135                 140

Ala Glu Asn Ser Leu Val Ala Tyr Lys Ala Ala Ser Asp Ile Ala Met
145                 150                 155                 160

Thr Glu Leu Pro Pro Thr His Pro Ile Arg Leu Gly Leu Ala Leu Asn
                165                 170                 175

Phe Ser Val Phe Tyr Tyr Glu Ile Leu Asn Ser Pro Asp Arg Ala Cys
            180                 185                 190

Arg Leu Ala Lys Ala Ala Phe Asp Asp Ala Ile Ala Glu Leu Asp Thr
        195                 200                 205

Leu Ser Glu Glu Ser Tyr Lys Asp Ser Thr Leu Ile Met Gln Leu Leu
    210                 215                 220

Arg Asp Asn Leu Thr Leu Trp Thr Ser Asp Met Gln Gly Asp Gly Glu
225                 230                 235                 240

Glu Gln Asn Lys Glu Ala Leu Gln Asp Val Glu Asp Glu Asn Gln
                245                 250                 255

<210> SEQ ID NO 8
<211> LENGTH: 247
<212> TYPE: PRT
<213> ORGANISM: Homo Sapiens

<400> SEQUENCE: 8

Met Val Asp Arg Glu Gln Leu Val Gln Lys Ala Arg Leu Ala Glu Gln
1               5                   10                  15

Ala Glu Arg Tyr Asp Asp Met Ala Ala Ala Met Lys Asn Val Thr Glu
                20                  25                  30
```

```
Leu Asn Glu Pro Leu Ser Asn Glu Glu Arg Asn Leu Leu Ser Val Ala
            35                  40                  45

Tyr Lys Asn Val Val Gly Ala Arg Arg Ser Ser Trp Arg Val Ile Ser
 50                  55                  60

Ser Ile Glu Gln Lys Thr Ser Ala Asp Gly Asn Glu Lys Lys Ile Glu
 65                  70                  75                  80

Met Val Arg Ala Tyr Arg Glu Lys Ile Glu Lys Glu Leu Glu Ala Val
                 85                  90                  95

Cys Gln Asp Val Leu Ser Leu Leu Asp Asn Tyr Leu Ile Lys Asn Cys
                100                 105                 110

Ser Glu Thr Gln Tyr Glu Ser Lys Val Phe Tyr Leu Lys Met Lys Gly
            115                 120                 125

Asp Tyr Tyr Arg Tyr Leu Ala Glu Val Ala Thr Gly Glu Lys Arg Ala
            130                 135                 140

Thr Val Val Glu Ser Ser Glu Lys Ala Tyr Ser Glu Ala His Glu Ile
145                 150                 155                 160

Ser Lys Glu His Met Gln Pro Thr His Pro Ile Arg Leu Gly Leu Ala
                165                 170                 175

Leu Asn Tyr Ser Val Phe Tyr Tyr Glu Ile Gln Asn Ala Pro Glu Gln
                180                 185                 190

Ala Cys His Leu Ala Lys Thr Ala Phe Asp Asp Ala Ile Ala Glu Leu
            195                 200                 205

Asp Thr Leu Asn Glu Asp Ser Tyr Lys Asp Ser Thr Leu Ile Met Gln
            210                 215                 220

Leu Leu Arg Asp Asn Leu Thr Leu Trp Thr Ser Asp Gln Gln Asp Asp
225                 230                 235                 240

Asp Gly Gly Glu Gly Asn Asn
                245

<210> SEQ ID NO 9
<211> LENGTH: 225
<212> TYPE: PRT
<213> ORGANISM: Homo Sapiens

<400> SEQUENCE: 9

Met Val Ser His Ser Glu Leu Arg Lys Leu Phe Tyr Ser Ala Asp Ala
 1               5                  10                  15

Val Cys Phe Asp Val Asp Ser Thr Val Ile Arg Glu Glu Gly Ile Asp
                 20                  25                  30

Glu Leu Ala Lys Ile Cys Gly Val Glu Asp Ala Val Ser Glu Met Thr
            35                  40                  45

Arg Arg Ala Met Gly Gly Ala Val Pro Phe Lys Ala Ala Leu Thr Glu
 50                  55                  60

Arg Leu Ala Leu Ile Gln Pro Ser Arg Glu Gln Val Gln Arg Leu Ile
 65                  70                  75                  80

Ala Glu Gln Pro Pro His Leu Thr Pro Gly Ile Arg Glu Leu Val Ser
                 85                  90                  95

Arg Leu Gln Glu Arg Asn Val Gln Val Phe Leu Ile Ser Gly Gly Phe
            100                 105                 110

Arg Ser Ile Val Glu His Val Ala Ser Lys Leu Asn Ile Pro Ala Thr
            115                 120                 125

Asn Val Phe Ala Asn Arg Leu Lys Ser Tyr Phe Asn Gly Glu Tyr Ala
            130                 135                 140

Gly Phe Asp Glu Thr Gln Pro Thr Ala Glu Ser Gly Gly Lys Gly Glu
145                 150                 155                 160
```

```
Val Ile Lys Leu Leu Lys Glu Lys Phe His Phe Lys Ile Ile Met
                165                 170                 175

Ile Gly Asp Gly Ala Thr Asp Met Glu Ala Cys Pro Pro Ala Asp Ala
            180                 185                 190

Phe Ile Gly Phe Gly Gly Asn Val Ile Arg Gln Gln Val Lys Asp Asn
            195                 200                 205

Ala Lys Trp Tyr Ile Thr Asp Phe Val Glu Leu Leu Gly Glu Leu Glu
            210                 215                 220

Glu
225

<210> SEQ ID NO 10
<211> LENGTH: 154
<212> TYPE: PRT
<213> ORGANISM: Homo Sapiens

<400> SEQUENCE: 10

Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
        35                  40                  45

His Glu Phe Gly Asp Asn Thr Ala Gly Cys Thr Ser Ala Gly Pro His
    50                  55                  60

Phe Asn Pro Leu Ser Arg Lys His Gly Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln
145                 150

<210> SEQ ID NO 11
<211> LENGTH: 140
<212> TYPE: PRT
<213> ORGANISM: Homo Sapiens

<400> SEQUENCE: 11

Met Ala Gly Trp Gln Ser Tyr Val Asp Asn Leu Met Cys Asp Gly Cys
1               5                   10                  15

Cys Gln Glu Ala Ala Ile Val Gly Tyr Cys Asp Ala Lys Tyr Val Trp
            20                  25                  30

Ala Ala Thr Ala Gly Gly Val Phe Gln Ser Ile Thr Pro Ile Glu Ile
        35                  40                  45

Asp Met Ile Val Gly Lys Asp Arg Glu Gly Phe Phe Thr Asn Gly Leu
    50                  55                  60

Thr Leu Gly Ala Lys Lys Cys Ser Val Ile Arg Asp Ser Leu Tyr Val
65                  70                  75                  80

Asp Gly Asp Cys Thr Met Asp Ile Arg Thr Lys Ser Gln Gly Gly Glu
                85                  90                  95
```

```
Pro Thr Tyr Asn Val Ala Val Gly Arg Ala Gly Arg Val Leu Val Phe
                100                 105                 110

Val Met Gly Lys Glu Gly Val His Gly Gly Leu Asn Lys Lys Ala
        115                 120                 125

Tyr Ser Met Ala Lys Tyr Leu Arg Asp Ser Gly Phe
130                 135                 140
```

<210> SEQ ID NO 12
<211> LENGTH: 119
<212> TYPE: PRT
<213> ORGANISM: Homo Sapiens

<400> SEQUENCE: 12

```
Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
                20                  25                  30

His Pro Ala Glu Asn Gly Lys Ser Asn Phe Leu Asn Cys Tyr Val Ser
            35                  40                  45

Gly Phe His Pro Ser Asp Ile Glu Val Asp Leu Leu Lys Asn Gly Glu
        50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
                100                 105                 110

Val Lys Trp Asp Arg Asp Met
        115
```

<210> SEQ ID NO 13
<211> LENGTH: 105
<212> TYPE: PRT
<213> ORGANISM: Homo Sapiens

<400> SEQUENCE: 13

```
Met Gly Asp Val Glu Lys Gly Lys Lys Ile Phe Ile Met Lys Cys Ser
1               5                   10                  15

Gln Cys His Thr Val Glu Lys Gly Lys His Lys Thr Gly Pro Asn
                20                  25                  30

Leu His Gly Leu Phe Gly Arg Lys Thr Gly Gln Ala Pro Gly Tyr Ser
            35                  40                  45

Tyr Thr Ala Ala Asn Lys Asn Lys Gly Ile Ile Trp Gly Glu Asp Thr
    50                  55                  60

Leu Met Glu Tyr Leu Glu Asn Pro Lys Lys Tyr Ile Pro Gly Thr Lys
65                  70                  75                  80

Met Ile Phe Val Gly Ile Lys Lys Lys Glu Glu Arg Ala Asp Leu Ile
                85                  90                  95

Ala Tyr Leu Lys Lys Ala Thr Asn Glu
                100                 105
```

<210> SEQ ID NO 14
<211> LENGTH: 98
<212> TYPE: PRT
<213> ORGANISM: Homo Sapiens

<400> SEQUENCE: 14

```
Met Met Cys Gly Ala Pro Ser Ala Thr Gln Pro Ala Thr Ala Glu Thr
1               5                   10                  15
```

```
Gln His Ile Ala Asp Gln Val Arg Ser Gln Leu Glu Glu Lys Glu Asn
            20                  25                  30

Lys Lys Phe Pro Val Phe Lys Ala Val Ser Phe Lys Ser Gln Val Val
        35                  40                  45

Ala Gly Thr Asn Tyr Phe Ile Lys Val His Val Gly Asp Glu Asp Phe
    50                  55                  60

Val His Leu Arg Val Phe Gln Ser Leu Pro His Glu Asn Lys Pro Leu
65                  70                  75                  80

Thr Leu Ser Asn Tyr Gln Thr Asn Lys Ala Lys His Asp Glu Leu Thr
                85                  90                  95

Tyr Phe

<210> SEQ ID NO 15
<211> LENGTH: 115
<212> TYPE: PRT
<213> ORGANISM: Homo Sapiens

<400> SEQUENCE: 15

Met Pro Met Phe Ile Val Asn Thr Asn Val Pro Arg Ala Ser Val Pro
1               5                   10                  15

Asp Gly Phe Leu Ser Glu Leu Thr Gln Gln Leu Ala Gln Ala Thr Gly
            20                  25                  30

Lys Pro Pro Gln Tyr Ile Ala Val His Val Val Pro Asp Gln Leu Met
        35                  40                  45

Ala Phe Gly Gly Ser Ser Glu Pro Cys Ala Leu Cys Ser Leu His Ser
    50                  55                  60

Ile Gly Lys Ile Gly Gly Ala Gln Asn Arg Ser Tyr Ser Lys Leu Leu
65                  70                  75                  80

Cys Gly Leu Leu Ala Glu Arg Leu Arg Ile Ser Pro Asp Arg Val Tyr
                85                  90                  95

Ile Asn Tyr Tyr Asp Met Asn Ala Ala Asn Val Gly Trp Asn Asn Ser
                100                 105                 110

Thr Phe Ala
        115

<210> SEQ ID NO 16
<211> LENGTH: 108
<212> TYPE: PRT
<213> ORGANISM: Homo Sapiens

<400> SEQUENCE: 16

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Phe Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu
                100                 105
```

```
<210> SEQ ID NO 17
<211> LENGTH: 105
<212> TYPE: PRT
<213> ORGANISM: Homo Sapiens

<400> SEQUENCE: 17

Met Val Lys Gln Ile Glu Ser Lys Thr Ala Phe Gln Glu Ala Leu Asp
1               5                   10                  15

Ala Ala Gly Asp Lys Leu Val Val Asp Phe Ser Ala Thr Trp Cys
            20                  25                  30

Gly Pro Cys Lys Met Ile Lys Pro Phe Phe His Ser Leu Ser Glu Lys
        35                  40                  45

Tyr Ser Asn Val Ile Phe Leu Glu Val Asp Val Asp Asp Cys Gln Asp
    50                  55                  60

Val Ala Ser Glu Cys Glu Val Lys Cys Met Pro Thr Phe Gln Phe Phe
65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val
            100                 105

<210> SEQ ID NO 18
<211> LENGTH: 250
<212> TYPE: PRT
<213> ORGANISM: Homo Sapiens

<400> SEQUENCE: 18

Met Ala Asp Asn Phe Ser Leu His Asp Ala Leu Ser Gly Ser Gly Asn
1               5                   10                  15

Pro Asn Pro Gln Gly Trp Pro Gly Ala Trp Gly Asn Gln Pro Ala Gly
            20                  25                  30

Ala Gly Gly Tyr Pro Gly Ala Ser Tyr Pro Gly Ala Tyr Pro Gly Gln
        35                  40                  45

Ala Pro Pro Gly Ala Tyr Pro Gly Gln Ala Pro Pro Gly Ala Tyr Pro
    50                  55                  60

Gly Ala Pro Gly Ala Tyr Pro Gly Ala Pro Ala Pro Gly Val Tyr Pro
65                  70                  75                  80

Gly Pro Pro Ser Gly Pro Gly Ala Tyr Pro Ser Ser Gly Gln Pro Ser
                85                  90                  95

Ala Thr Gly Ala Tyr Pro Ala Thr Gly Pro Tyr Gly Ala Pro Ala Gly
            100                 105                 110

Pro Leu Ile Val Pro Tyr Asn Leu Pro Leu Pro Gly Gly Val Val Pro
        115                 120                 125

Arg Met Leu Ile Thr Ile Leu Gly Thr Val Lys Pro Asn Ala Asn Arg
    130                 135                 140

Ile Ala Leu Asp Phe Gln Arg Gly Asn Asp Val Ala Phe His Phe Asn
145                 150                 155                 160

Pro Arg Phe Asn Glu Asn Asn Arg Arg Val Ile Val Cys Asn Thr Lys
                165                 170                 175

Leu Asp Asn Asn Trp Gly Arg Glu Glu Arg Gln Ser Val Phe Pro Phe
            180                 185                 190

Glu Ser Gly Lys Pro Phe Lys Ile Gln Val Leu Val Glu Pro Asp His
        195                 200                 205

Phe Lys Val Ala Val Asn Asp Ala His Leu Leu Gln Tyr Asn His Arg
    210                 215                 220

Val Lys Lys Leu Asn Glu Ile Ser Lys Leu Gly Ile Ser Gly Asp Ile
225                 230                 235                 240
```

Asp Leu Thr Ser Ala Ser Tyr Thr Met Ile
            245                 250

<210> SEQ ID NO 19
<211> LENGTH: 698
<212> TYPE: PRT
<213> ORGANISM: Homo Sapiens

<400> SEQUENCE: 19

Met Arg Leu Ala Val Gly Ala Leu Leu Val Cys Ala Val Leu Gly Leu
 1               5                  10                  15

Cys Leu Ala Val Pro Asp Lys Thr Val Arg Trp Cys Ala Val Ser Glu
            20                  25                  30

His Glu Ala Thr Lys Cys Gln Ser Phe Arg Asp His Met Lys Ser Val
        35                  40                  45

Ile Pro Ser Asp Gly Pro Ser Val Ala Cys Val Lys Lys Ala Ser Tyr
    50                  55                  60

Leu Asp Cys Ile Arg Ala Ile Ala Ala Asn Glu Ala Asp Ala Val Thr
65                  70                  75                  80

Leu Asp Ala Gly Leu Val Tyr Asp Ala Tyr Leu Ala Pro Asn Asn Leu
                85                  90                  95

Lys Pro Val Val Ala Glu Phe Tyr Gly Ser Lys Glu Asp Pro Gln Thr
            100                 105                 110

Phe Tyr Tyr Ala Val Ala Val Val Lys Lys Asp Ser Gly Phe Gln Met
        115                 120                 125

Asn Gln Leu Arg Gly Lys Lys Ser Cys His Thr Gly Leu Gly Arg Ser
130                 135                 140

Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
                165                 170                 175

Cys Ala Pro Cys Ala Asp Gly Thr Asp Phe Pro Gln Leu Cys Gln Leu
            180                 185                 190

Cys Pro Gly Cys Gly Cys Ser Thr Leu Asn Gln Tyr Phe Gly Tyr Ser
        195                 200                 205

Gly Ala Phe Lys Cys Leu Lys Asp Gly Ala Gly Asp Val Ala Phe Val
    210                 215                 220

Lys His Ser Thr Ile Phe Glu Asn Leu Ala Asn Lys Ala Asp Arg Asp
225                 230                 235                 240

Gln Tyr Glu Leu Leu Cys Leu Asp Asn Thr Arg Lys Pro Val Asp Glu
                245                 250                 255

Tyr Lys Asp Cys His Leu Ala Gln Val Pro Ser His Thr Val Val Ala
            260                 265                 270

Arg Ser Met Gly Gly Lys Glu Asp Leu Ile Trp Glu Leu Leu Asn Gln
        275                 280                 285

Ala Gln Glu His Phe Gly Lys Asp Lys Ser Lys Glu Phe Gln Leu Phe
    290                 295                 300

Ser Ser Pro His Gly Lys Asp Leu Leu Phe Lys Asp Ser Ala His Gly
305                 310                 315                 320

Phe Leu Lys Val Pro Pro Arg Met Asp Ala Lys Met Tyr Leu Gly Tyr
                325                 330                 335

Glu Tyr Val Thr Ala Ile Arg Asn Leu Arg Glu Gly Thr Cys Pro Glu
            340                 345                 350

Ala Pro Thr Asp Glu Cys Lys Pro Val Lys Trp Cys Ala Leu Ser His
        355                 360                 365

His Glu Arg Leu Lys Cys Asp Glu Trp Ser Val Asn Ser Val Gly Lys
        370                 375                 380
Ile Glu Cys Val Ser Ala Glu Thr Thr Glu Asp Cys Ile Ala Lys Ile
385                 390                 395                 400
Met Asn Gly Glu Ala Asp Ala Met Ser Leu Asp Gly Gly Phe Val Tyr
            405                 410                 415
Ile Ala Gly Lys Cys Gly Leu Val Pro Val Leu Ala Glu Asn Tyr Asn
            420                 425                 430
Lys Ser Asp Asn Cys Glu Asp Thr Pro Glu Ala Gly Tyr Phe Ala Val
            435                 440                 445
Ala Val Val Lys Lys Ser Ala Ser Asp Leu Thr Trp Asp Asn Leu Lys
        450                 455                 460
Gly Lys Lys Ser Cys His Thr Ala Val Gly Arg Thr Ala Gly Trp Asn
465                 470                 475                 480
Ile Pro Met Gly Leu Leu Tyr Asn Lys Ile Asn His Cys Arg Phe Asp
            485                 490                 495
Glu Phe Phe Ser Glu Gly Cys Ala Pro Gly Ser Lys Lys Asp Ser Ser
            500                 505                 510
Leu Cys Lys Leu Cys Met Gly Ser Gly Leu Asn Leu Cys Glu Pro Asn
        515                 520                 525
Asn Lys Glu Gly Tyr Tyr Gly Tyr Thr Gly Ala Phe Arg Cys Leu Val
        530                 535                 540
Glu Lys Gly Asp Val Ala Phe Val Lys His Gln Thr Val Pro Gln Asn
545                 550                 555                 560
Thr Gly Gly Lys Asn Pro Asp Pro Trp Ala Lys Asn Leu Asn Glu Lys
            565                 570                 575
Asp Tyr Glu Leu Leu Cys Leu Asp Gly Thr Arg Lys Pro Val Glu Glu
            580                 585                 590
Tyr Ala Asn Cys His Leu Ala Arg Ala Pro Asn His Ala Val Val Thr
        595                 600                 605
Arg Lys Asp Lys Glu Ala Cys Val His Lys Ile Leu Arg Gln Gln Gln
610                 615                 620
His Leu Phe Gly Ser Asn Val Thr Asp Cys Ser Gly Asn Phe Cys Leu
625                 630                 635                 640
Phe Arg Ser Glu Thr Lys Asp Leu Leu Phe Arg Asp Asp Thr Val Cys
            645                 650                 655
Leu Ala Lys Leu His Asp Arg Asn Thr Tyr Glu Lys Tyr Leu Gly Glu
            660                 665                 670
Glu Tyr Val Lys Ala Val Gly Asn Leu Arg Lys Cys Ser Thr Ser Ser
        675                 680                 685
Leu Leu Glu Ala Cys Thr Phe Arg Arg Pro
        690                 695

<210> SEQ ID NO 20
<211> LENGTH: 437
<212> TYPE: PRT
<213> ORGANISM: Homo Sapiens

<400> SEQUENCE: 20

Met Ala Ala Gly Thr Leu Tyr Thr Tyr Pro Glu Asn Trp Arg Ala Phe
1               5                   10                  15
Lys Ala Leu Ile Ala Ala Gln Tyr Ser Gly Ala Gln Val Arg Val Leu
            20                  25                  30
Ser Ala Pro Pro His Phe His Phe Gly Gln Thr Asn Arg Thr Pro Glu
        35                  40                  45

```
Phe Leu Arg Lys Phe Pro Ala Gly Lys Val Pro Ala Phe Glu Gly Asp
 50                  55                  60
Asp Gly Phe Cys Val Phe Glu Ser Asn Ala Ile Ala Tyr Tyr Val Ser
 65                  70                  75                  80
Asn Glu Glu Leu Arg Gly Ser Thr Pro Glu Ala Ala Gln Val Val
                 85                  90                  95
Gln Trp Val Ser Phe Ala Asp Ser Asp Ile Val Pro Pro Ala Ser Thr
             100                 105                 110
Trp Val Phe Pro Thr Leu Gly Ile Met His His Asn Lys Gln Ala Thr
             115                 120                 125
Glu Asn Ala Lys Glu Glu Val Arg Arg Ile Leu Gly Leu Leu Asp Ala
 130                 135                 140
Tyr Leu Lys Thr Arg Thr Phe Leu Val Gly Arg Val Thr Leu Ala
 145                 150                 155                 160
Asp Ile Thr Val Val Cys Thr Leu Leu Trp Leu Tyr Lys Gln Val Leu
             165                 170                 175
Glu Pro Ser Phe Arg Gln Ala Phe Pro Asn Thr Asn Arg Trp Phe Leu
             180                 185                 190
Thr Cys Ile Asn Gln Pro Gln Phe Arg Ala Val Leu Gly Glu Val Lys
             195                 200                 205
Leu Cys Glu Lys Met Ala Gln Phe Asp Ala Lys Lys Phe Ala Glu Thr
 210                 215                 220
Gln Pro Lys Lys Asp Thr Pro Arg Lys Glu Lys Gly Ser Arg Glu Glu
225                 230                 235                 240
Lys Gln Lys Pro Gln Ala Glu Arg Lys Glu Glu Lys Lys Ala Ala Ala
                 245                 250                 255
Pro Ala Pro Glu Glu Glu Met Asp Glu Cys Glu Gln Ala Leu Ala Ala
             260                 265                 270
Glu Pro Lys Ala Lys Asp Pro Phe Ala His Leu Pro Lys Ser Thr Phe
             275                 280                 285
Val Leu Asp Glu Phe Lys Arg Lys Tyr Ser Asn Glu Asp Thr Leu Ser
 290                 295                 300
Val Ala Leu Pro Tyr Phe Trp Glu His Phe Asp Lys Asp Gly Trp Ser
305                 310                 315                 320
Leu Trp Tyr Ser Glu Tyr Arg Phe Pro Glu Glu Leu Thr Gln Thr Phe
                 325                 330                 335
Met Ser Cys Asn Leu Ile Thr Gly Met Phe Gln Arg Leu Asp Lys Leu
             340                 345                 350
Arg Lys Asn Ala Phe Ala Ser Val Ile Leu Phe Gly Thr Asn Asn Ser
             355                 360                 365
Ser Ser Ile Ser Gly Val Trp Val Phe Arg Gly Gln Glu Leu Ala Phe
             370                 375                 380
Pro Leu Ser Pro Asp Trp Gln Val Asp Tyr Glu Ser Tyr Thr Trp Arg
385                 390                 395                 400
Lys Leu Asp Pro Gly Ser Glu Glu Thr Gln Thr Leu Val Arg Glu Tyr
                 405                 410                 415
Phe Ser Trp Glu Gly Ala Phe Gln His Val Gly Lys Ala Phe Asn Gln
             420                 425                 430
Gly Lys Ile Phe Lys
             435

<210> SEQ ID NO 21
<211> LENGTH: 585
<212> TYPE: PRT
```

<213> ORGANISM: Homo Sapiens

<400> SEQUENCE: 21

```
Met Thr Pro Pro Arg Leu Phe Trp Val Trp Leu Leu Val Ala Gly Thr
 1               5                   10                  15
Gln Gly Val Asn Asp Gly Asp Met Arg Leu Ala Asp Gly Gly Ala Thr
            20                  25                  30
Asn Gln Gly Arg Val Glu Ile Phe Tyr Arg Gly Gln Trp Gly Thr Val
        35                  40                  45
Cys Asp Asn Leu Trp Asp Leu Thr Asp Ala Ser Val Val Cys Arg Ala
    50                  55                  60
Leu Gly Phe Glu Asn Ala Thr Gln Ala Leu Gly Arg Ala Ala Phe Gly
65                  70                  75                  80
Gln Gly Ser Gly Pro Ile Met Leu Asp Glu Val Gln Cys Thr Gly Thr
                85                  90                  95
Glu Ala Ser Leu Ala Asp Cys Lys Ser Leu Gly Trp Leu Lys Ser Asn
            100                 105                 110
Cys Arg His Glu Arg Asp Ala Gly Val Val Cys Thr Asn Glu Thr Arg
        115                 120                 125
Ser Thr His Thr Leu Asp Leu Ser Arg Glu Leu Ser Glu Ala Leu Gly
    130                 135                 140
Gln Ile Phe Asp Ser Gln Arg Gly Cys Asp Leu Ser Ile Ser Val Asn
145                 150                 155                 160
Val Gln Gly Glu Asp Ala Leu Gly Phe Cys Gly His Thr Val Ile Leu
                165                 170                 175
Thr Ala Asn Leu Glu Ala Gln Ala Leu Trp Lys Glu Pro Gly Ser Asn
            180                 185                 190
Val Thr Met Ser Val Asp Ala Glu Cys Val Pro Met Val Arg Asp Leu
        195                 200                 205
Leu Arg Tyr Phe Tyr Ser Arg Arg Ile Asp Ile Thr Leu Ser Ser Val
    210                 215                 220
Lys Cys Phe His Lys Leu Ala Ser Ala Tyr Gly Ala Arg Gln Leu Gln
225                 230                 235                 240
Gly Tyr Cys Ala Ser Leu Phe Ala Ile Leu Leu Pro Gln Asp Pro Ser
                245                 250                 255
Phe Gln Met Pro Leu Asp Leu Tyr Ala Tyr Ala Val Ala Thr Gly Asp
            260                 265                 270
Ala Leu Leu Glu Lys Leu Cys Leu Gln Phe Leu Ala Trp Asn Phe Glu
        275                 280                 285
Ala Leu Thr Gln Ala Glu Ala Trp Pro Ser Val Pro Thr Asp Leu Leu
    290                 295                 300
Gln Leu Leu Leu Pro Arg Ser Asp Leu Ala Val Pro Ser Glu Leu Ala
305                 310                 315                 320
Leu Leu Lys Ala Val Asp Thr Trp Ser Trp Gly Glu Arg Ala Ser His
                325                 330                 335
Glu Glu Val Glu Gly Leu Val Glu Lys Ile Arg Phe Pro Met Met Leu
            340                 345                 350
Pro Glu Glu Leu Phe Glu Leu Gln Phe Asn Leu Ser Leu Tyr Trp Ser
        355                 360                 365
His Glu Ala Leu Phe Gln Lys Lys Thr Leu Gln Ala Leu Glu Phe His
    370                 375                 380
Thr Val Pro Phe Gln Leu Leu Ala Arg Tyr Lys Gly Leu Asn Leu Thr
385                 390                 395                 400
Glu Asp Thr Tyr Lys Pro Arg Ile Tyr Thr Ser Pro Thr Trp Ser Ala
```

|     |     |     |     |     |     |     |     |     |     |     |     |
| --- | --- | --- | --- | --- | --- | --- | --- | --- | --- | --- | --- |
|     |     |     | 405 |     |     |     | 410 |     |     |     | 415 |
| Phe | Val | Thr | Asp<br>420 | Ser | Ser | Trp | Ser | Ala<br>425 | Arg | Lys | Ser | Gln | Leu<br>430 | Val | Tyr |
| Gln | Ser | Arg<br>435 | Arg | Gly | Pro | Leu | Val<br>440 | Lys | Tyr | Ser | Ser | Asp<br>445 | Tyr | Phe | Gln |
| Ala | Pro<br>450 | Ser | Asp | Tyr | Arg | Tyr<br>455 | Tyr | Pro | Tyr | Gln | Ser<br>460 | Phe | Gln | Thr | Pro |
| Gln<br>465 | His | Pro | Ser | Phe | Leu<br>470 | Phe | Gln | Asp | Lys | Arg<br>475 | Val | Ser | Trp | Ser | Leu<br>480 |
| Val | Tyr | Leu | Pro | Thr<br>485 | Ile | Gln | Ser | Cys | Trp<br>490 | Asn | Tyr | Gly | Phe | Ser<br>495 | Cys |
| Ser | Ser | Asp | Glu<br>500 | Leu | Pro | Val | Leu | Gly<br>505 | Leu | Thr | Lys | Ser | Gly<br>510 | Gly | Ser |
| Asp | Arg | Thr<br>515 | Ile | Ala | Tyr | Glu | Asn<br>520 | Lys | Ala | Leu | Met | Leu<br>525 | Cys | Glu | Gly |
| Leu | Phe | Val<br>530 | Ala | Asp | Val | Thr<br>535 | Asp | Phe | Glu | Gly | Trp<br>540 | Lys | Ala | Ala | Ile |
| Pro<br>545 | Ser | Ala | Leu | Asp | Thr<br>550 | Asn | Ser | Ser | Lys | Ser<br>555 | Thr | Ser | Ser | Phe | Pro<br>560 |
| Cys | Pro | Ala | Gly | His<br>565 | Phe | Asn | Gly | Phe | Arg<br>570 | Thr | Val | Ile | Arg | Pro<br>575 | Phe |
| Tyr | Leu | Thr | Asn<br>580 | Ser | Ser | Gly | Val | Asp<br>585 |

What is claimed is:

1. A method of inducing migration of an immune cell toward an ovarian cancer cell comprising inhibiting the activity of a chemorepellant release from the cancer cell, wherein the migration of the immune cell is induced in a patient suffering from ovarian cancer, and wherein the inhibition of the chemorepellant is carried out by the administration of an antibody which binds to apolipoprotein A1.

2. A method of inducing negative chemotaxis of a neutrophil in a patient in need thereof comprising administering apolipoprotein A1 to said patient in an amount effective to induce negative chemotaxis of the neutrophil, wherein the patient is suffering from an inflammatory condition, wherein the apolipoprotein A1 is administered locally, and wherein the inflammatory condition is selected from the group consisting of injection site reaction, Behcet's syndrome, synovitis, gout, fasciitis, arthritides, uveitis, burns, dermatitis, dermatomyositis, urticaria, acne, adult respiratory distress syndrome, bronchitis, emphysema, rhinitis, cystic fibrosis, pneumonitis, pneumoultramicroscopic silicovolcanoconiosis, alveolitis, bronchiolitis, pharyngitis, pleurisy, sinusitis, chronic obstructive pulmonary disease, acute lung injury, and hay fever.

* * * * *